United States Patent
Hiramine et al.

(10) Patent No.: US 11,434,472 B2
(45) Date of Patent: Sep. 6, 2022

(54) AGENT FOR REMOVING UNDIFFERENTIATED IPS CELLS

(71) Applicant: Sumitomo Pharma Co., Ltd., Osaka (JP)

(72) Inventors: Yasushi Hiramine, Kobe (JP); Masayo Fujiwara, Kobe (JP); Hitoshi Ban, Osaka (JP); Futoshi Hasegawa, Nishinomiya (JP)

(73) Assignee: Sumitomo Pharma Co., Ltd., Osaka (JP)

( * ) Notice: Subject to any disclaimer, the term of this patent is extended or adjusted under 35 U.S.C. 154(b) by 611 days.

(21) Appl. No.: 16/471,474

(22) PCT Filed: Dec. 19, 2017

(86) PCT No.: PCT/JP2017/045612
§ 371 (c)(1),
(2) Date: Jun. 19, 2019

(87) PCT Pub. No.: WO2018/117127
PCT Pub. Date: Jun. 28, 2018

(65) Prior Publication Data
US 2019/0390172 A1     Dec. 26, 2019

(30) Foreign Application Priority Data

Dec. 20, 2016 (JP) .............................. JP2016-247139

(51) Int. Cl.
| | | |
|---|---|---|
| *C12N 5/074* | (2010.01) | |
| *A61K 35/12* | (2015.01) | |
| *A61K 31/4178* | (2006.01) | |
| *A61K 31/422* | (2006.01) | |
| *A61K 31/427* | (2006.01) | |
| *A61K 31/4439* | (2006.01) | |
| *A61K 31/5365* | (2006.01) | |
| *A61K 31/4375* | (2006.01) | |
| *A61K 31/4709* | (2006.01) | |
| *A61K 31/4725* | (2006.01) | |
| *A61K 31/497* | (2006.01) | |
| *A61K 31/4174* | (2006.01) | |
| *A61K 31/4365* | (2006.01) | |

(Continued)

(52) U.S. Cl.
CPC ........ *C12N 5/0696* (2013.01); *A61K 31/4174* (2013.01); *A61K 31/4178* (2013.01); *A61K 31/422* (2013.01); *A61K 31/427* (2013.01); *A61K 31/4365* (2013.01); *A61K 31/4375* (2013.01); *A61K 31/4439* (2013.01); *A61K 31/4709* (2013.01); *A61K 31/4725* (2013.01); *A61K 31/497* (2013.01); *A61K 31/5365* (2013.01); *A61K 35/12* (2013.01); *C07D 233/88* (2013.01); *C07D 401/12* (2013.01); *C07D 403/12* (2013.01); *C07D 413/12* (2013.01); *C07D 417/12* (2013.01); *C07D 471/04* (2013.01); *C07D 498/04* (2013.01); *C12N 2501/999* (2013.01)

(58) Field of Classification Search
CPC ............ A61K 31/4164; A61K 31/4178; A61K 31/422; A61K 31/427; A61K 31/437; A61K 31/4375; A61K 31/4439; A61K 31/4709; A61K 31/4725; A61K 31/497; A61K 31/5365; A61K 35/12; A61K 35/545; A61L 27/38; A61P 43/00; C07D 233/88; C07D 401/12; C07D 403/12; C07D 413/12; C07D 417/12; C07D 471/04; C07D 498/04; C12N 2501/999; C12N 5/0693; C12N 5/0696
See application file for complete search history.

(56) References Cited

FOREIGN PATENT DOCUMENTS

| JP | 2015-525207 A | 9/2015 |
|---|---|---|
| JP | 2016-093178 A | 5/2016 |

(Continued)

OTHER PUBLICATIONS

"Inhibitors of Stearoyl-CoA Desaturase 1 as Anti-obesity Drug," Monthly Fine Chemicals, Aug. 2009, 38(8):12-24 (with English abstract).
Ben-David et al., "Selective Elimination of Human Pluripotent Stem Cells by an Oleate Synthesis Inhibitor Discovered in a High-Throughput Screen," Cell Stem Cell, 2013, 12:167-179.
Matsumoto et al., "A Cytotoxic Antibody Recognizing Lacto-N-fucopentaose I (LNFP I) on Human Induced Pluripotent Stem (hiPS) Cells," Journal of Biological Chemistry, 2015, 290(33):20071-20085.
PCT International Preliminary Report on Patentability in International Appln. No. PCT/JP2017/045612, dated Mar. 30, 2018, 6 pages (English translation).

(Continued)

*Primary Examiner* — Erich A Leeser
(74) *Attorney, Agent, or Firm* — Fish & Richardson P.C.

(57) ABSTRACT

The present invention provides a compound of formula (1) or a salt thereof wherein ring $Q^1$ is optionally-substituted $C_{6-10}$ aryl, etc.; $R^1$ and $R^2$ are independently hydrogen atom, etc.; $W^1$ is $C_{1-4}$ alkylene which may be optionally substituted with 1 to 3 fluorine atoms or $C_{3-7}$ cycloalkyl; $W^2$ is —$NR^{4a}$C(O)—, etc. wherein $R^{4a}$ is hydrogen atom or $C_{1-6}$ alkyl; ring $Q^2$ is optionally-substituted $C_{6-10}$ aryl, etc., which has an inhibitory effect on the sphere-forming ability of cancer cells and is useful an agent for removing iPS cells.

(1)

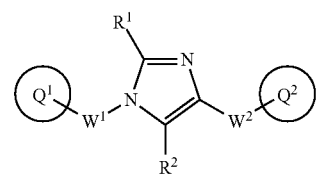

19 Claims, 4 Drawing Sheets

(51) Int. Cl.
  *C07D 233/88* (2006.01)
  *C07D 401/12* (2006.01)
  *C07D 403/12* (2006.01)
  *C07D 413/12* (2006.01)
  *C07D 417/12* (2006.01)
  *C07D 471/04* (2006.01)
  *C07D 498/04* (2006.01)

(56) References Cited

FOREIGN PATENT DOCUMENTS

| WO | 2016/027253 | A1 | | 2/2016 | |
| WO | WO 2016/027253 | | * | 2/2016 | ............ A61K 31/55 |
| WO | 2016/208591 | A1 | | 4/2018 | |
| WO | 2016/208592 | A1 | | 4/2018 | |
| WO | 2017/146128 | A1 | | 12/2018 | |

OTHER PUBLICATIONS

PCT International Search Report and Written Opinion in International Appln. PCT/JP2017/045612, dated Mar. 20, 2018, 2 pages (English translation).

Tateno et al., "Elimination of Tumorigenic Human Pluripotent Stem Cells by a Recombinant Lectin-Toxin Fusion Protein,"Stem Cell Reports, 2015, 4(5):811-20.

Yamaguchi et al., "Synthesis and SAR of novel, potent and orally bioavailable 4-aminoimidazole-based inhibitors of stearoyl-CoA desaturase 1," The 27th medicinal chemistry symposium abstract, p. 166-167.

Yamasaki et al., "Generation of Human Induced Pluripotent Stem (iPS) Cells in Serum- and Feeder-Free Defined Culture and TGF-b1 Regulation of Pluripotency," PLOS One, 2014, 9(1):e87151.

* cited by examiner

[Fig. 1]
Compound of Example 1-2
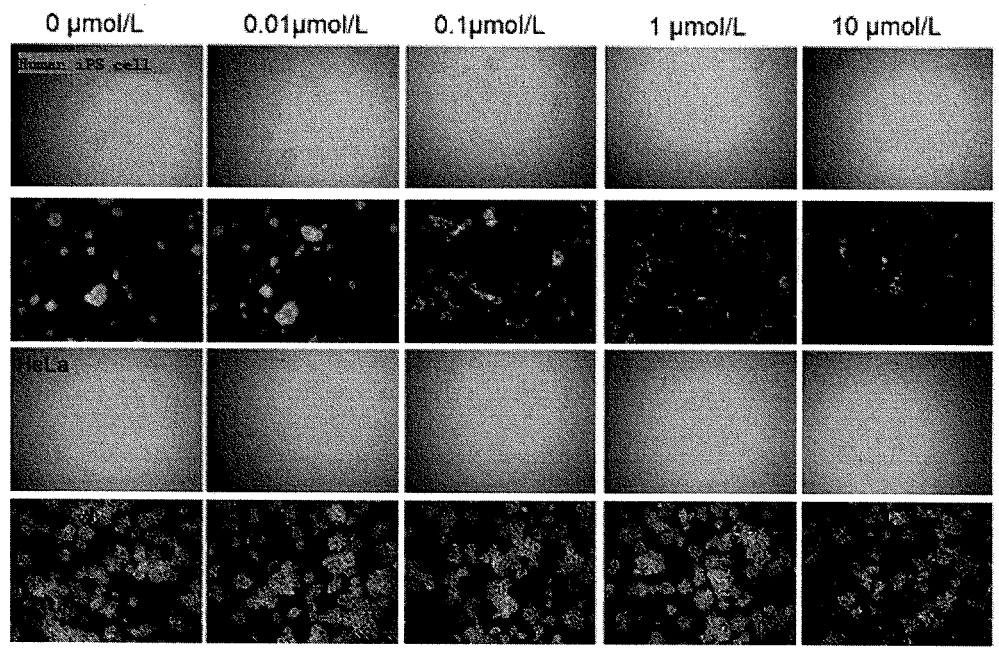
[Fig. 2]
Compound of Example 10-2
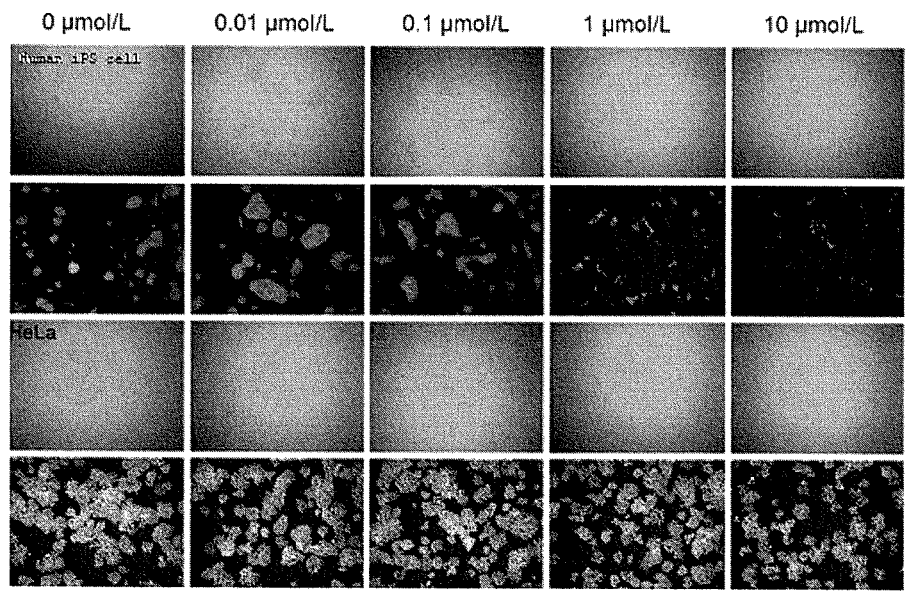

[Fig. 3]
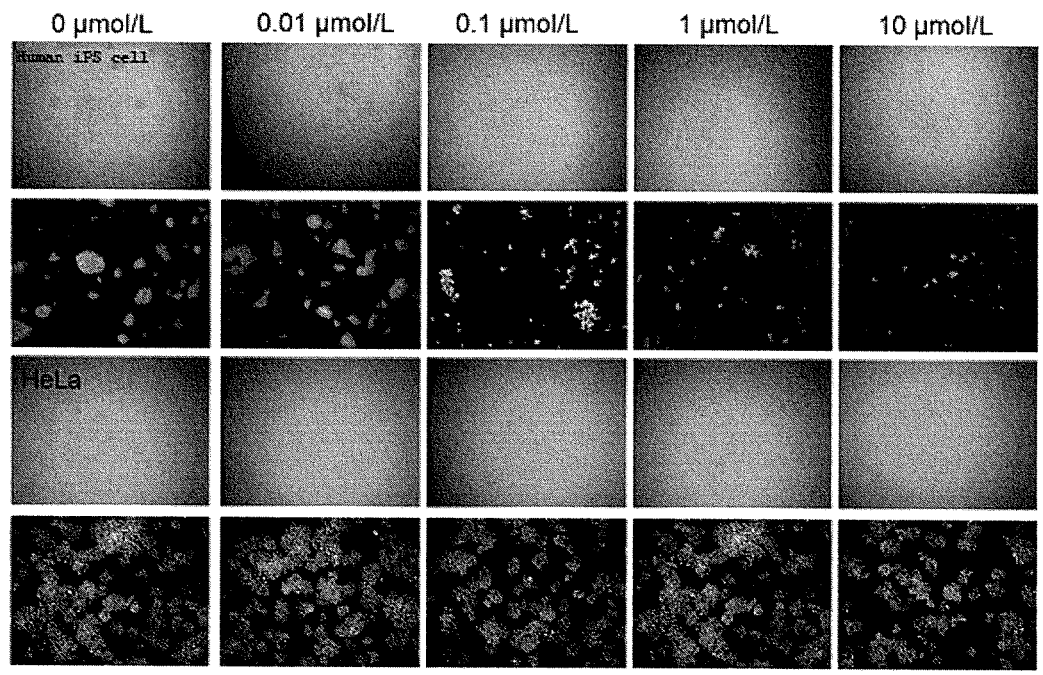
[Fig. 4]
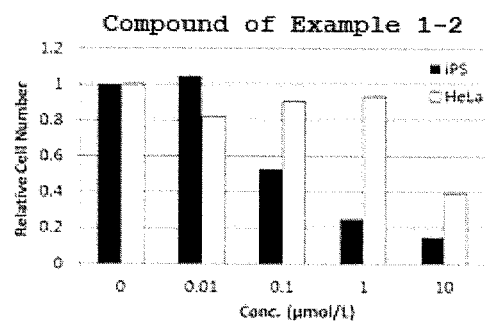
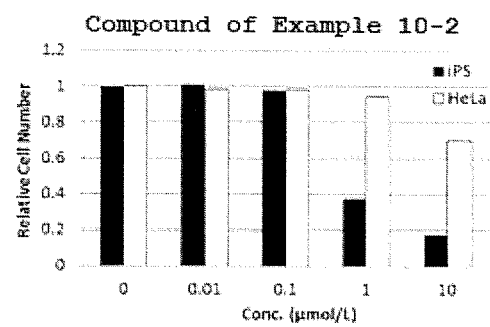
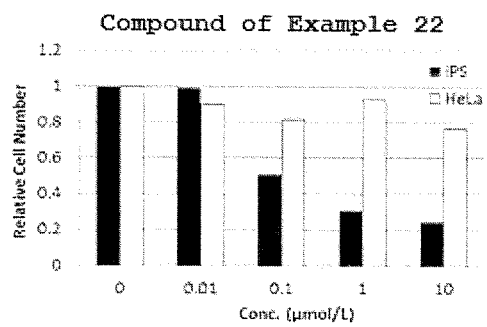

[Fig. 5]
Compound of Example 1-2
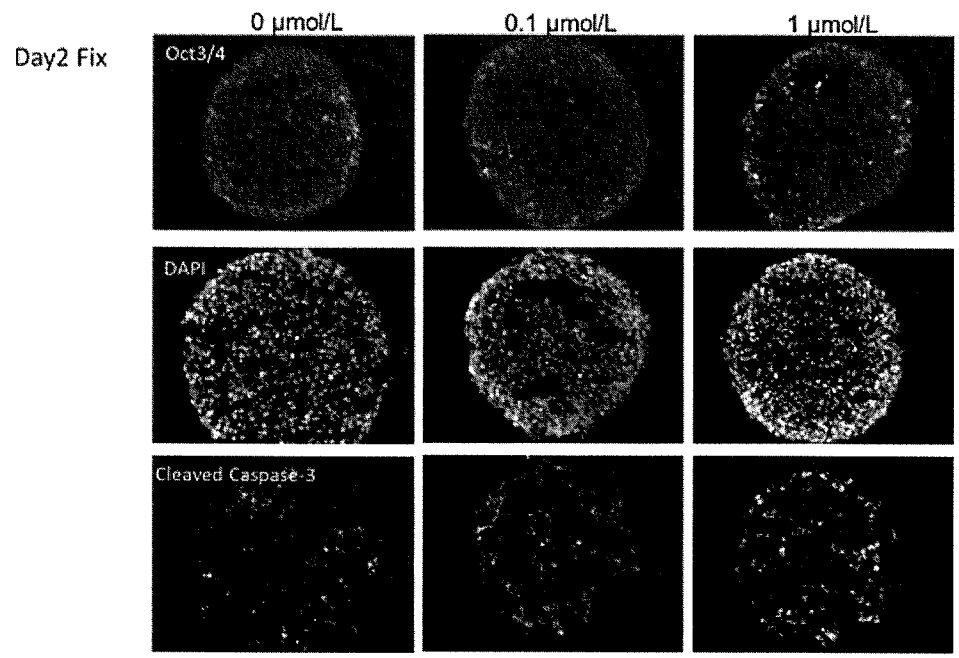
[Fig. 6]
Compound of Example 10-2
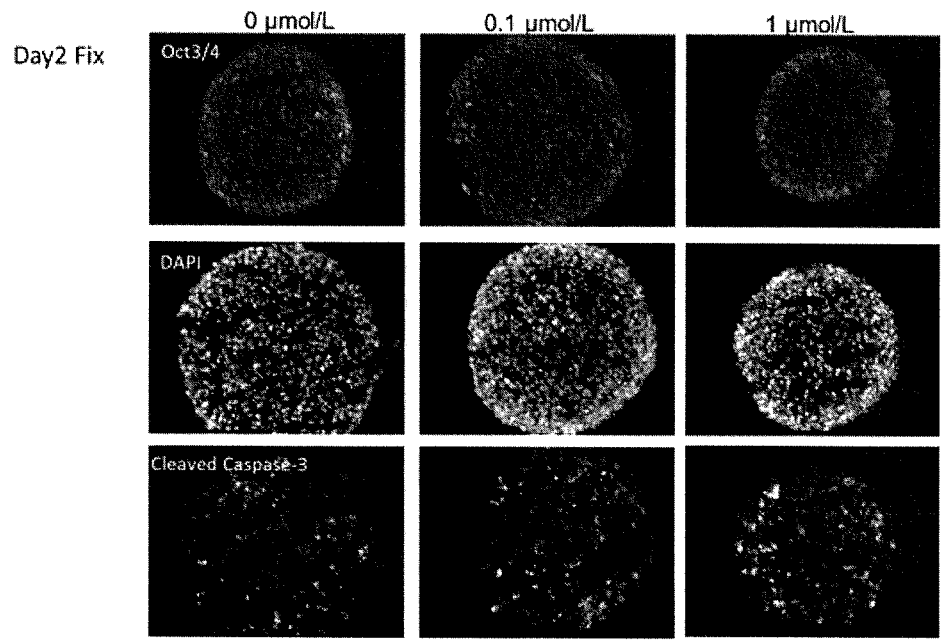

[Fig. 7]
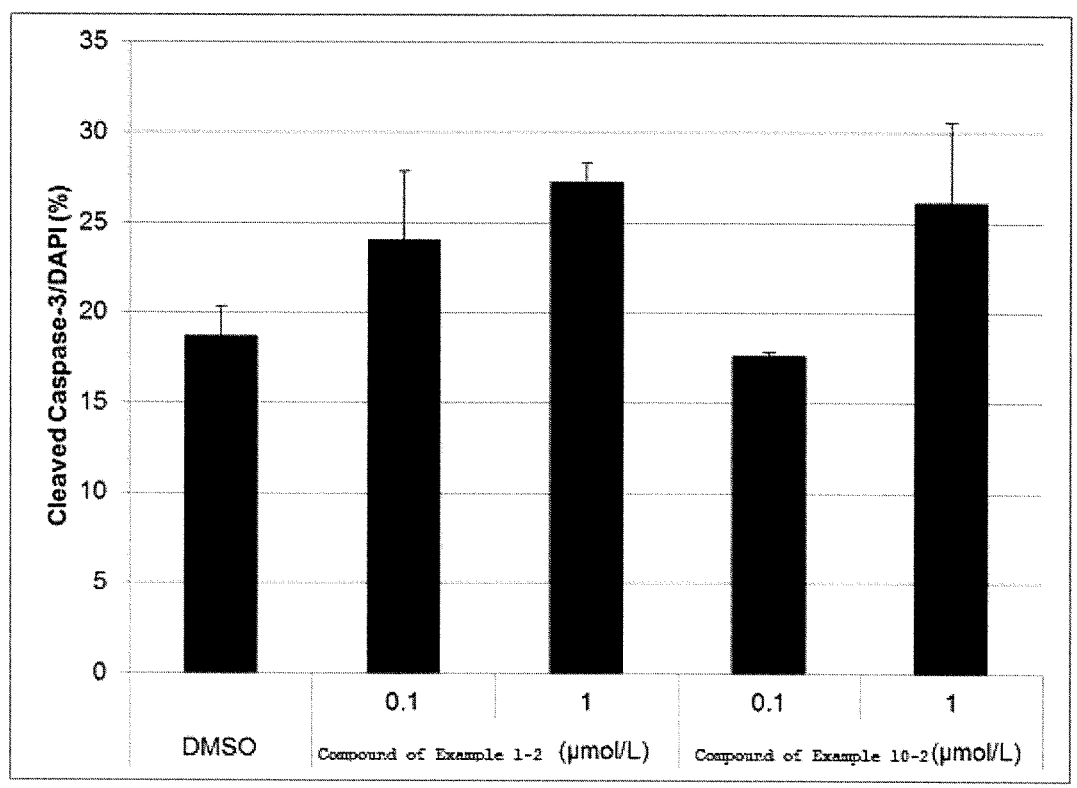

AGENT FOR REMOVING UNDIFFERENTIATED IPS CELLS

TECHNICAL FIELD

The present invention relates to an agent for removing undifferentiated iPS cells, comprising an imidazolylamide derivative including a salt thereof.

BACKGROUND ART

Induced pluripotent stem cells (iPS cells: induced pluripotent stem cell) are cells with both self-renewal ability and differentiation ability, and form a tumor called as Teratoma when the cells are transplanted as they are in vivo and undifferentiated iPS cells are contained therein (Non-Patent Document 1). Teratoma is differentiated from so-called cancer (malignant tumor). However, if teratoma is formed from iPS cells contained in a finished cell product manufactured by using iPS cells as starting material, the safety and effectiveness of the product may be lost. Hence, in the development of iPS cell-derived cell products, it is very important that no undifferentiated iPS cell with teratoma-forming ability is contained in the products.

In these days, it is possible to detect iPS cells with high sensitivity. On the other hand, such detection method is technically limited. When a cell product is produced from a large number of cells, it cannot be completely denied that trace amounts of iPS cells are contained in the cell product. In order to reduce the possibility that iPS cells are contained in a cell product and enhance the safety of the product, various attempts to remove iPS cells in an intermediate or a final product have been done as manufacturing approach. Examples of the methods include a method for removing iPS cells using a compound for inducing cell death.

As the compound capable of inducing cell death for iPS cells, compounds such as a fusion protein of a glycoprotein recognizing iPS cells and a toxin (Non-Patent Document 2), an antibody capable of recognizing iPS cells and inducing cell death (Non-Patent Document 3), and a compound capable of inhibiting the desaturation of a fatty acid (Patent Document 1 and Non-Patent Document 4) have been known. On the other hand, it is not known that the imidazolylamide derivative of the present invention can be used as such compounds. The fusion protein of a glycoprotein recognizing iPS cells and a toxin as well as the antibody for removing iPS cells act effectively on plane-cultured monolayer iPS cells. On the other hand, the penetration efficiency of the compounds into a cell mass without blood circulatory system is considered to be extremely poor when the compounds are added to the cell mass, because the compounds are macromolecules with high molecular weight.

Non-Patent Documents 5 and 6 disclose compounds such as a 4-aminoimidazole derivative useful as an anti-obesity agent. However, there is no disclosure that the compounds can induce cell death for iPS cells.

PRIOR ART DOCUMENTS

Patent Documents

Patent Document 1: JP 2015-525207

Non-Patent Documents

Non-Patent Document 1: PLOS ONE, 9(1), e87151. (2014)
Non-Patent Document 2: Stem Cell Reports, 4(5), 811-20 (2015)
Non-Patent Document 3: Journal of Biological Chemistry, 290, 20071-20085 (2015)
Non-Patent Document 4: Cell Stem Cell, 12, 167-179 (2013)
Non-Patent Document 5: The 27th medicinal chemistry symposium abstract, p. 166-167
Non-Patent Document 6: Monthly Fine Chemicals, August 2009, Vol. 38, No. 8, p. 12-24

SUMMARY OF INVENTION

Problem to be Solved by the Invention

An object of the present invention is to provide a method for effectively removing undifferentiated iPS cells which are contained in an iPS cell-derived cell medicine.

Means for Solving the Problems

The present inventors have extensively studied to reach the above object, and then have found that a compound of the following formula (1) or a salt thereof (hereinafter referred to as "the present compound", as necessary) has an inhibitory effect on the sphere-forming ability of cancer cells and can effectively remove undifferentiated iPS cells which are contained in an iPS cell-derived cell medicine. Based upon the new findings, the present invention has been completed.

The present invention provides inventions described below.

[1] An agent for removing iPS cells, comprising a compound of formula (1):

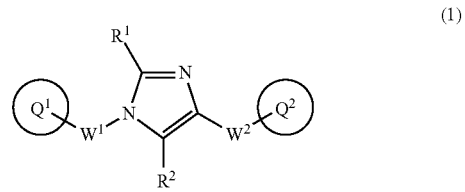

or a salt thereof, wherein $Q^1$ is optionally-substituted $C_{6-10}$ aryl, optionally-substituted $C_{6-10}$ aryloxy, optionally-cycloalkyl, or optionally-substituted 5- to 10-membered heteroaryl;

$R^1$ and $R^2$ are independently hydrogen atom, halogen atom, or $C_{1-6}$ alkyl which may be optionally substituted with the same or different 1 to 3 halogen atoms;

$W^1$ is $C_{1-4}$ alkylene which may be optionally substituted with 1 to 3 fluorine atoms or $C_{3-7}$ cycloalkyl;

$W^2$-$Q^2$ is —$NR^{3a}C(O)$-$Q^2$, —$NR^{3a}C(O)OCH_2$-$Q^2$, —$NR^{3a}C(O)OCH_2$-$Q^2$, —$NR^{3a}C(O)NR^{3b}$-$Q^2$, —$NR^{3a}C(O)NR^{3b}CH_2$-$Q^2$, —$NR^{3a}C(O)CH_2O$-$Q^2$, —$NR^{3a}C(O)CH_2$-$Q^2$, —$NR^{3a}C(O)CH_2CH_2$-$Q^2$, —$C(O)NR^{3a}$-$Q^2$, —$C(O)NR^{3a}CH_2$-$Q^2$, —$C(O)NR^{3a}CH_2CH_2$-$Q^2$, or —$NR^{3a}C(O)$—$CR^{3c}$=$CR^{3d}$-$Q^2$ wherein $R^{3a}$ and $R^{3b}$ are independently hydrogen atom or $C_{1-6}$ alkyl; $R^{3c}$ and $R^{3d}$ are independently hydrogen atom, fluorine atom, or $C_{1-6}$ alkyl; and ring $Q^2$ is optionally-substituted $C_{6-10}$ aryl or optionally-substituted 5- to 10-membered heteroaryl.

[2] The agent according to [1], wherein $Q^1$ is phenyl which may be optionally substituted with the same or different 1 to 4 groups selected from the group consisting of
(1) halogen atom,
(2) $C_{1-6}$ alkyl which may be optionally substituted with the same or different 1 to 3 groups selected from the group consisting of halogen atom, hydroxy, and $C_{1-6}$ alkoxy,
(3) $C_{1-6}$ alkoxy which may be optionally substituted with the same or different 1 to 3 groups selected from the group consisting of halogen atom, hydroxy, $C_{1-6}$ alkoxy, and phenyl,
(4) amino which may be optionally substituted with the same or different 1 to 2 $C_{1-6}$ alkyl groups,
(5) $C_{6-10}$ aryl which may be optionally substituted with the same or different 1 to 4 groups selected from the group consisting of halogen atom, $C_{1-6}$ alkyl, and $C_{1-6}$ alkoxy,
(6) $_{O6-10}$ aryloxy which may be optionally substituted with the same or different 1 to 4 groups selected from the group consisting of halogen atom, $C_{1-6}$ alkyl, and $C_{1-6}$ alkoxy,
(7) 5- to 10-membered heteroaryl which may be optionally substituted with the same or different 1 to 4 groups selected from the group consisting of halogen atom, $C_{1-6}$ alkyl, and $C_{1-6}$ alkoxy, and
(8) $C_{1-6}$ alkoxy-carbonyl.
[3] The agent according to [1] or [2], wherein $Q^1$ is phenyl which may be optionally substituted with the same or different 1 to 4 groups selected from the group consisting of halogen atom, and $C_{1-6}$ alkyl which may be optionally substituted with the same or different 1 to 3 halogen atoms.
[4] The agent according to any one of [1]-[3], wherein $W^2$-$Q^2$ is —NHC(O)-$Q^2$, —NHC(O)—CH=CH-$Q^2$, —C(O)NH-$Q^2$, or —NHC(O)CH$_2$O-$Q^2$.
[5] The agent according to any one of [1]-[4], wherein $W^1$ is methylene.
[6] The agent according to any one of [1]-[5], wherein ring $Q_2$ is
(1) phenyl which may be optionally substituted with the same or different 1 to 4 groups selected from the group consisting of
  (a) halogen atom,
  (b) $C_{1-6}$ alkyl which may be optionally substituted with the same or different 1 to 3 groups selected from the group consisting of halogen atom, hydroxy, and $C_{1-6}$ alkoxy,
  (c) $C_{1-6}$ alkoxy which may be optionally substituted with the same or different 1 to 3 groups selected from the group consisting of halogen atom, hydroxy, and $C_{1-6}$ alkoxy,
  (d) $C_{3-7}$ cycloalkyl,
  (e) $C_{2-6}$ alkenyl,
  (f) cyano,
  (g) amino which may be optionally substituted with the same or different 1 to 2 $C_{1-6}$ alkyl groups, and
  (h) $C_{1-6}$ alkyl-carbonylamino,
(2) 5- to 10-membered heteroaryl which may be optionally substituted with the same or different 1 to 4 groups selected from the group consisting of (a) to (h) defined in the above (1), or
(3) a group of the following formula (11), (12), (13), (14), (15), or (16):

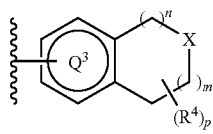
(11)

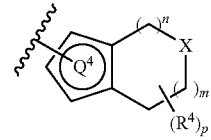
(12)

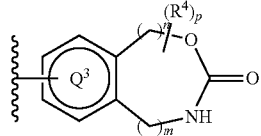
(13)

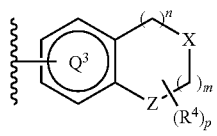
(14)

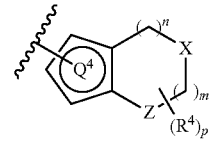
(15)

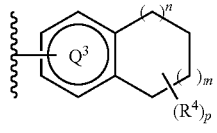
(16)

wherein ring $Q^3$ is optionally-substituted benzene ring, optionally-substituted pyridine ring, optionally-substituted pyrimidine ring, optionally-substituted pyridazine ring, or optionally-substituted pyrazine ring; ring $Q^4$ is optionally-substituted 5-membered heteroaryl ring;

n and m are independently 0, 1, or 2, provided that n and m are not simultaneously 0;

X and Z are independently $NR^5$, —$NR^{3e}C(O)$—, —$C(O)NR^{3e}$—, or O wherein $R^5$ is hydrogen atom, $C_{1-6}$ alkyl which may be optionally substituted with the same or different 1 to 3 halogen atoms, or $C_{1-6}$ alkylcarbonyl; $R^{3e}$ is hydrogen atom or $C_{1-6}$ alkyl;

p is 1, 2, 3, 4, or 5;

$R^4$ is, independently when two or more exist, hydrogen atom, halogen atom, hydroxy, oxo, $C_{1-6}$ alkyl which may be optionally substituted with the same or different 1 to 3 halogen atoms, or $C_{1-6}$ alkoxy which may be optionally substituted with the same or different 1 to 3 halogen atoms.

[7] The agent according to any one of [1]-[6], wherein ring $Q_2$ is (1) phenyl which may be optionally substituted with the same or different 1 to 2 groups selected from the group consisting of $C_{1-6}$ alkoxy which may be optionally substituted with hydroxy and $C_{1-6}$ alkyl-carbonylamino, (2) a group of the following formula (2):

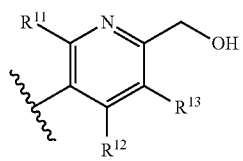

wherein $R^{11}$, $R^{12}$, and $R^{13}$ are independently
(a) hydrogen atom,
(b) halogen atom,
(c) $C_{1-6}$ alkyl which may be optionally substituted with the same or different 1 to 3 fluorine atoms, or
(d) amino which may be optionally substituted with the same or different 1 to 2 $C_{1-6}$ alkyl groups, or
(3) a group of the following formula (21):

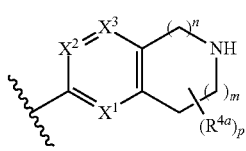

wherein $X^1$ is N or $CR^{14}$;
$X^2$ is N or $CR^{15}$;
$X^3$ is N or $CR^{16}$;
provided that $X^1$, $X^2$ and $X^3$ are not simultaneously N;
$R^{14}$, $R^{15}$, and $R^{16}$ are independently
(a) hydrogen atom,
(b) halogen atom,
(c) $C_{1-6}$ alkyl which may be optionally substituted with the same or different 1 to 3 halogen atoms, or
(d) $C_{1-6}$ alkoxy which may be optionally substituted with the same or different 1 to 3 halogen atoms;
n and m are independently 0, 1 or 2, provided that n and m are not simultaneously 0;
p is 1, 2, 3, 4 or 5;
$R^{4a}$ is, independently when two or more exist, hydrogen atom, halogen atom, or $C_{1-6}$ alkyl which may be optionally substituted with the same or different 1 to 3 halogen atoms.
[8] The agent according to [7], wherein $W^2$-$Q^2$ is —NHC(O)-$Q_2$, or —C(O)NH-$Q^2$; and
ring $Q^2$ is a group of formula (2) or (21).
[9] The agent according to [7] or [8], wherein $R^{11}$ and $R^{12}$ are hydrogen atom;
$R^{13}$ is hydrogen atom, $C_{1-4}$ alkyl which may be optionally substituted with 1 to 3 fluorine atoms, or amino;
$R^{14}$, $R^{15}$, and $R^{16}$ are independently hydrogen atom or fluorine atom;
n is 1;
m is 0 or 1;
p is 1 or 2;
$R^{4a}$ is, independently when two or more exist, hydrogen atom or methyl.
[10] The agent according to any one of [1]-[7], wherein $W^2$-$Q^2$ is —NHC(O)—CH═CH-$Q^2$; and
ring $Q^2$ is phenyl which may be optionally substituted with the same or different 1 to 2 groups selected from the group consisting of $C_{1-6}$ alkoxy which may be optionally substituted with hydroxy, and $C_{1-6}$ alkyl-carbonylamino.

[11] The agent according to any one of [1]-[10], wherein $R^1$ and $R^2$ are hydrogen atom.
[12] An agent for removing iPS cells, comprising the compound of formula (1) according to [1] or a salt thereof selected from the following compounds:
(2E)-3-[4-(acetylamino)phenyl]-N-(1-[3-(trifluoromethyl)benzyl]-1H-imidazol-4-yl)prop-2-enamide Example 1-1

N-[1-(3-chlorobenzyl)-1H-imidazol-4-yl]-3,4-dimethoxybenzamide (Example 10-1), and
6-(hydroxymethyl)-N-{1-[3-(trifluoromethyl)benzyl]-1H-imidazol-4-yl}nicotinamide (Example 22).
[13] A method of removing iPS cells, which comprises adding the compound of formula (1) according to any one of [1]-[12] or a salt thereof into a culture solution containing iPS cells.
[14] A method of removing iPS cells, which comprises adding the compound of formula (1) according to any one of [1]-[12] or a salt thereof into a culture solution containing a cell mass formed from iPS cells.
[15] Use of the compound of formula (1) according to any one of [1]-[12] or a salt thereof for removing iPS cells contained inside a cell mass formed from iPS cells.
[16] Use of the compound of formula (1) according to any one of [1]-[12] or a salt thereof for preparing an iPS cell-derived cell population free of iPS cells.
[17] A method of preparing an iPS cell-derived cell population free of iPS cells, which comprises contacting an iPS cell-derived cell population with the compound of formula (1) according to any one of [1]-[12] or a salt thereof.
[18] A method of preparing an iPS cell-derived cell population free of cells maintaining pluripotency, which comprises
(1) inducing differentiation of a cell population containing iPS cells, and
(2) contacting the cell population obtained in the above (1) with the compound of formula (1) according to any one of [1]-[12] or a salt thereof.
[19] An iPS cell-derived cell population free of iPS cells prepared by the method according to [17] or [18].
[20] The cell population according to [19] containing cells for transplantation.
[21] A pharmaceutical composition comprising cells in the cell population according to [19] as an active ingredient.

Effects of the Invention

The present compound can effectively remove undifferentiated iPS cells from an iPS cell-derived cell medicine. In particular, the present compound can achieve efficient removal of undifferentiated iPS cells contained inside a cell mass formed from iPS cells, which has been technically difficult until now.

BRIEF DESCRIPTION OF THE DRAWINGS

FIG. 1 shows the bright field observation results (first and third lines) and the DAPI nuclear staining results (second and fourth lines) of human iPS cells (first and second lines) and HeLa cells (third and fourth lines) treated with the compound of Example 1-2 in each concentration for 24 hours.
FIG. 2 shows the bright field observation results (first and third lines) and the DAPI nuclear staining results (second and fourth lines) of human iPS cells (first and second lines)

and HeLa cells (third and fourth lines) treated with the compound of Example 10-2 in each concentration for 24 hours.

FIG. 3 shows the bright field observation results (first and third lines) and the DAPI nuclear staining results (second and fourth lines) of human iPS cells (first and second lines) and HeLa cells (third and fourth lines) treated with the compound of Example 22 in each concentration for 24 hours.

FIG. 4 shows the results of the remaining iPS cells (black bar) and HeLa cells (white bar) after the treatment with the compounds of Examples 1-2, 10-2, and 22 quantified by DAPI nuclear staining.

FIG. 5 Cell aggregates formed by inducing differentiation of human iPS cells were treated with the compound of Example 1-2 in each concentration for 24 hours. FIG. 5 shows the results of immunostaining of Oct3/4 positive cells (first line), DAPI nuclear staining (second line), and immunostaining of Cleaved Caspase-3 positive cells (third line) for the cell aggregates.

FIG. 6 Cell aggregates formed by inducing differentiation human iPS cells were treated with the compound of Example 10-2 in each concentration for 24 hours. FIG. 6 shows the results of immunostaining of Oct3/4 positive cells (first line), DAPI nuclear staining (second line), and immunostaining of Cleaved Caspase-3 positive cells (third line) for the cell aggregates.

FIG. 7 The ratio of Cleaved Caspase-3 positive cells in the cell aggregates treated by the compounds of Examples 1-2 and 10-2 was quantified by correction with DAPI nuclear staining. FIG. 7 shows the average of the quantitative results for the negative control (DMSO), the compound of Example 1-2, and the compound of Example 10-2 (each 3 cases).

DESCRIPTION OF EMBODIMENTS

Hereinafter, the present invention is explained in detail. The number of carbon atoms in the definition of the "substituent" used herein may be expressed as, for example, "$C_{1-6}$". Specifically, the term "$C_{1-6}$ alkyl" is used for the same meaning as alkyl having 1 to 6 carbon atoms.

Specific examples of "halogen atom" used herein include fluorine atom, chlorine atom, bromine atom, and iodine atom. The halogen atom is preferably fluorine atom or chlorine atom.

The term "$C_{1-6}$ alkyl" used herein means a straight or branched, saturated hydrocarbon group having 1 to 6 carbon atoms. The group is preferably "$C_{1-4}$ alkyl". Specific examples of the "$C_{1-6}$ alkyl" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, and 2-ethylbutyl.

The term "$C_{2-6}$ alkenyl" used herein means a straight or branched, unsaturated hydrocarbon group having 2 to 6 carbon atoms and 1 to 3 carbon-carbon double bonds. The group is preferably "$C_{2-4}$ alkenyl". Specific examples of the "$C_{2-6}$ alkenyl" include ethenyl, propenyl, butenyl, pentenyl, and hexenyl.

The term "$C_{1-4}$ alkylene" used herein means a straight or branched, divalent saturated hydrocarbon group having 1 to 4 carbon atoms, or a divalent saturated hydrocarbon group containing a cyclic structure having 3 to 4 carbon atoms.

Specific examples of the straight or branched "$C_{1-4}$ alkylene" include methylene, ethylene, propylene, butylene, 1-methylmethylene, 1-ethylmethylene, 1-propylmethylene, 1-methylethylene, 2-methylethylene, and 1-ethylethylene. Preferred examples thereof include methylene and ethylene.

Specific examples of the "$C_{1-4}$ alkylene" containing a cyclic structure include the following groups:

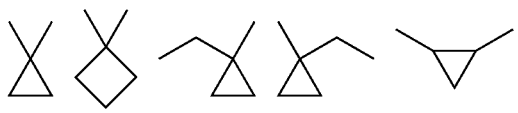

The "$C_{1-6}$ alkyl" moiety of the term "$C_{1-6}$ alkoxy" used herein is as defined in the above "$C_{1-6}$ alkyl". The group is preferably "$C_{1-4}$ alkoxy". Specific examples of the "$C_{1-6}$ alkoxy" include methoxy, ethoxy, propoxy, isopropoxy, butoxy, isobutoxy, sec-butoxy, and tert-butoxy.

The term "$C_{3-10}$ cycloalkyl" used herein means a 3- to 10-membered monocyclic or polycyclic, saturated or partially-unsaturated hydrocarbon group. The group is preferably "$C_{3-7}$ cycloalkyl". Specific examples of the "$C_{3-10}$ cycloalkyl" include cyclopropyl, cyclobutyl, cyclopentyl, cyclohexyl, cycloheptyl, cyclopentenyl, cyclohexenyl, decalinyl, adamantyl, and norbornyl.

The term "$C_{6-10}$ aryl" used herein means an aromatic hydrocarbon group having 6 to 10 carbon atoms. The group is preferably "$C_6$ aryl" (phenyl). Specific examples of the "$C_{6-10}$ aryl" include phenyl, 1-naphthyl, and 2-naphthyl.

The "$C_{6-10}$ aryl" also encompasses a fused ring group of phenyl with a 5- to 7-membered non-aromatic ring which contains the same or different one or more (e.g., 1 to 4) heteroatoms selected from nitrogen atom, sulfur atom, or oxygen atom or a 5- to 7-membered saturated or partially-unsaturated hydrocarbon ring (cyclopentane or cyclohexane). The polycyclic "$C_{6-10}$ aryl" in which an aromatic ring and a non-aromatic ring are fused has the bond for a "group" in only the aromatic ring.

Specific examples of the group include the groups of the following formulae. The bond across a ring in the following formulae means that a "group" is linked at any replaceable position in the ring.

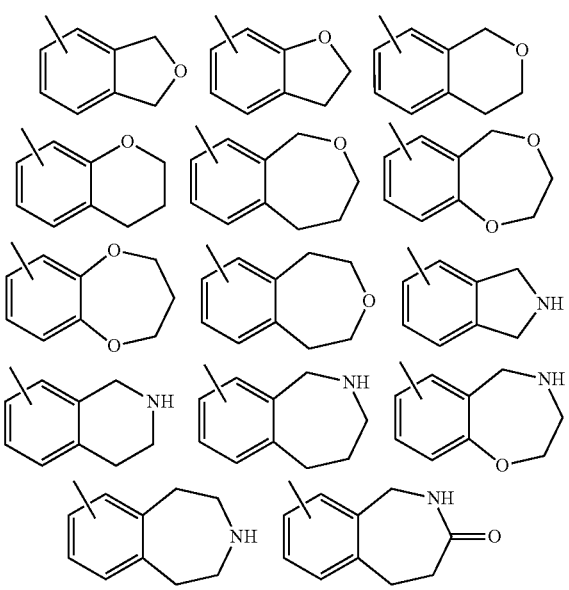

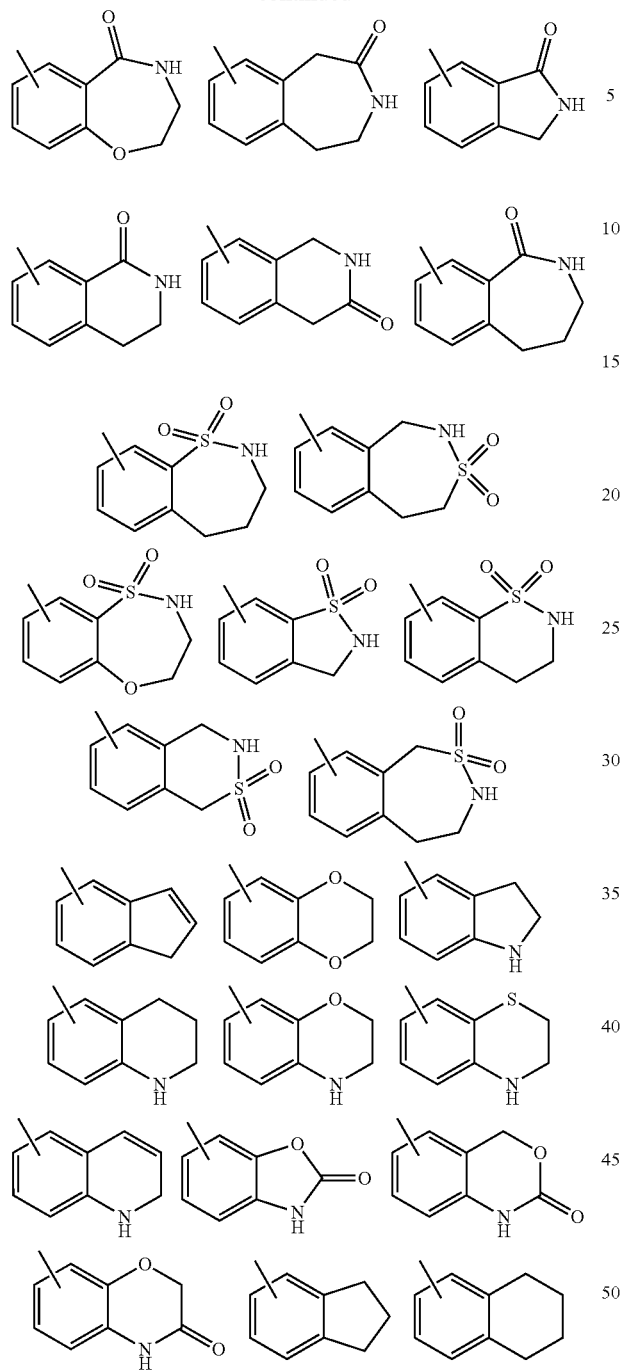
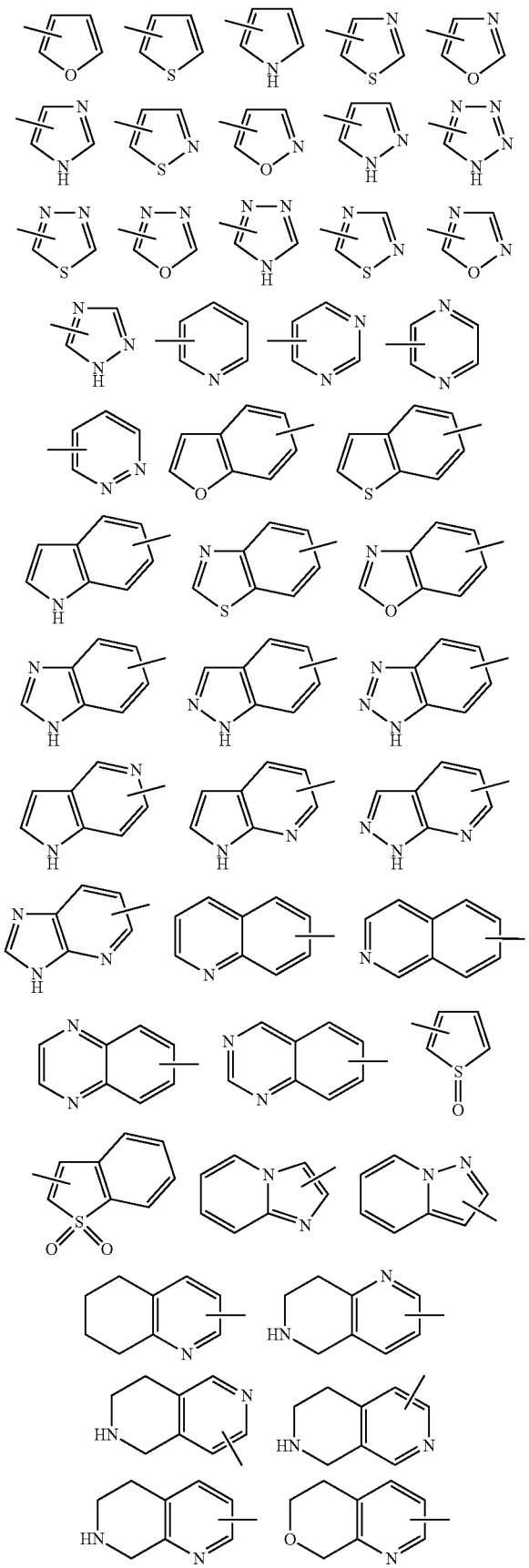

Examples of the term "5- to 10-membered heteroaryl" used herein include a 5- to 10-membered mono- or bi-cyclic aromatic heterocyclic group which contains the same or different one or more (e.g., 1 to 4) heteroatoms selected from the group consisting of nitrogen atom, sulfur atom, and oxygen atom. The bicyclic heteroaryl also encompasses a fused ring group of a monocyclic heteroaryl group mentioned above with an aromatic ring (such as benzene and pyridine) or a non-aromatic ring (such as cyclohexane, pyrrolidine, piperidine, tetrahydrofuran, tetrahydropyran, and 1,4-dioxane). Specific examples of the "heteroaryl" include the groups of the following formulae:

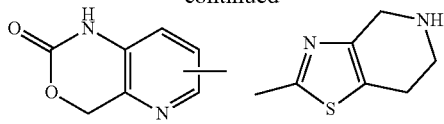

The bond across a ring in the above formulae means that a "group" is linked at any replaceable position in the ring. For example, when a group is the heteroaryl group of the following formula:

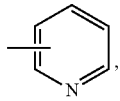

the group means 2-pyridyl, 3-pyridyl, or 4-pyridyl.

Furthermore, when the "heteroaryl" is a bicyclic group, for example, the group of the following formula:

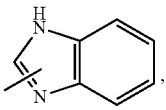

the group may be 1-benzimidazolyl, 2-benzimidazolyl, or 4-, 5-, 6- or 7-benzimidazolyl.

The polycyclic heteroaryl in which an aromatic ring and a non-aromatic ring (such as cyclohexane and piperidine) are fused has the bond for a "group" in only the aromatic ring. For example, when the "polycyclic heteroaryl" is the group of the following formula:

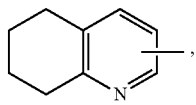

the bond means that a "group" is linked at the 2-, 3-, or 4-position.

In the groups of formulae (11)-(16) defined in the above [6], the two atoms indicated by arrows, which are shared between ring $Q^3$ or ring $Q^4$ and another ring fused with the ring, are carbon.

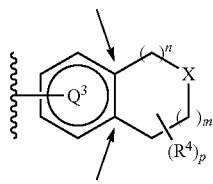
(11)

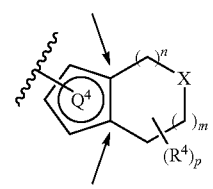
(12)

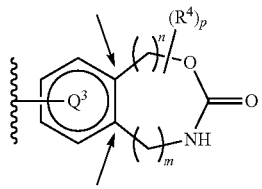
(13)

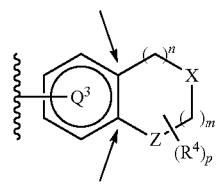
(14)

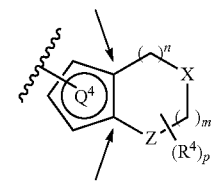
(15)

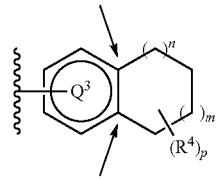
(16)

The "$C_{1-6}$ alkyl" moiety of the term "$C_{1-6}$ alkyl-carbonylamino" used herein is as defined in the above "$C_{1-6}$ alkyl". The group is preferably "$C_{1-4}$ alkyl-carbonylamino", more preferably methylcarbonylamino (acetylamino).

Examples of the substituent in the terms "optionally-substituted $C_{6-10}$ aryl", "optionally-substituted $C_{6-10}$ aryloxy", "optionally-substituted $C_{6-10}$ arylthio", "optionally-substituted $C_{3-10}$ cycloalkyl", "optionally-substituted 5- to 10-membered heteroaryl", "optionally-substituted benzene ring", "optionally-substituted pyridine ring", "optionally-substituted pyrimidine ring", "optionally-substituted pyridazine ring", and "optionally-substituted pyrazine ring" include (a) halogen atom,
(b) $C_{1-6}$ alkyl which may be optionally substituted with the same or different 1 to 3 groups selected from the group consisting of halogen atom, hydroxy, and $C_{1-6}$ alkoxy,
(c) $C_{1-6}$ alkoxy which may be optionally substituted with the same or different 1 to 3 groups selected from the consisting of halogen atom, hydroxy, and $C_{1-6}$ alkoxy,
(d) cyano,
(e) phenyl which may be optionally substituted with the same or different 1 to 4 groups selected from the group consisting of halogen atom, $C_{1-6}$ alkyl, and $C_{1-6}$ alkoxy,
(f) 5- or 6-membered heteroaryl which may be optionally substituted with the same or different 1 to 4 groups selected from the group consisting of halogen atom, $C_{1-6}$ alkyl, and $C_{1-6}$ alkoxy,
(g) phenoxy which may be optionally substituted with the same or different 1 to 4 groups selected from the group consisting of halogen atom, $C_{1-6}$ alkyl, and $C_{1-6}$ alkoxy,
(h) hydroxy,
(i) amino which may be optionally substituted with the same or different 1 to 2 $C_{1-6}$ alkyl groups, and (j) aminocarbonyl wherein the amino moiety thereof may be optionally substituted with the same or different 1 to 2 $C_{1-6}$ alkyl groups.

The substituent is preferably halogen atom, $C_{1-6}$ alkyl which may be optionally substituted with the same or different 1 to 3 groups selected from the group consisting of halogen atom, hydroxy, and $C_{1-6}$ alkoxy, $C_{1-6}$ alkoxy which may be optionally substituted with the same or different 1 to 3 groups selected from the group consisting of halogen atom, hydroxy, and $C_{1-6}$ alkoxy, or cyano.

The substituent is more preferably halogen atom, or $C_{1-6}$ alkyl which may be optionally substituted with 1 to 3 fluorine atoms.

In the polycyclic aryl or heteroaryl in which an aromatic ring and a non-aromatic ring are fused, the above substituents may be introduced on either the aromatic ring or the non-aromatic ring.

In the present compound of formula (1), $W^1$, $W^2$, $R^1$, $R^2$, ring $Q^1$, and ring $Q^2$ are preferably those shown below, but the technical scope of the present invention should not be limited to the following compounds.

$W^1$ is preferably methylene.

$W_2$-$Q_2$ is preferably —NHC(O)-$Q^2$, —NHC(O)—CH═CH-$Q^2$, —C(O)NH-$Q^2$, or —NHC(O)CH$_2$O-$Q_2$. $W^2$-$Q^2$ is more preferably —NHC(O)-$Q^2$ or —NHC(O)—CH═CH-$Q^2$.

Preferably, $R^1$ and $R^2$ are independently hydrogen atom, chlorine atom, or methyl. $R^1$ and $R^2$ are more preferably hydrogen atom.

Ring $Q^1$ is preferably phenyl which may be optionally substituted with the same or different 1 to 4 groups selected from the group consisting of
(1) halogen atom,
(2) $C_{1-6}$ alkyl which may be optionally substituted with the same or different 1 to 3 groups selected from the group consisting of halogen atom, hydroxy, and $C_{1-6}$ alkoxy,
(3) $C_{1-6}$ alkoxy which may be optionally substituted with the same or different 1 to 3 groups selected from the group consisting of halogen atom, hydroxy, $C_{1-6}$ alkoxy, and phenyl,
(4) amino which may be optionally substituted with the same or different 1 to 2 $C_{1-6}$ alkyl groups,
(5) $C_{6-10}$ aryl which may be optionally substituted with the same or different 1 to 4 groups selected from the group consisting of halogen atom, $C_{1-6}$ alkyl, and $C_{1-6}$ alkoxy,
(6) $C_{6-10}$ aryloxy which may be optionally substituted with the same or different 1 to 4 groups selected from the group consisting of halogen atom, $C_{1-6}$ alkyl, and $C_{1-6}$ alkoxy,
(7) 5- to 10-membered heteroaryl which may be optionally substituted with the same or different 1 to 4 groups selected from the group consisting of halogen atom, $C_{1-6}$ alkyl, and alkoxy, and
(8) $C_{1-6}$ alkoxycarbonyl.

Ring $Q^1$ is more preferably phenyl which may be optionally substituted with the same or different 1 to 4 groups selected from the group consisting of halogen atom, and $C_{1-6}$ alkyl which may be optionally substituted with the same or different 1 to 3 halogen atoms; and furthermore preferably phenyl substituted with the same or different 1 to 3 halogen atoms, or trifluoromethylphenyl.

Ring $Q^2$ is preferably
(1) phenyl which may be optionally substituted with the same or different 1 to 4 groups selected from the group consisting of (a) halogen atom,
(b) $C_{1-6}$ alkyl which may be optionally substituted with the same or different 1 to 3 groups selected from the group consisting of halogen atom, hydroxy, and $C_{1-6}$ alkoxy,
(c) $C_{1-6}$ alkoxy which may be optionally substituted with the same or different 1 to 3 groups selected from the group consisting of halogen atom, hydroxy, and $C_{1-6}$ alkoxy,
(d) $C_{3-7}$ cycloalkyl,
(e) $C_{2-6}$ alkenyl,
(f) cyano,
(g) amino which may be optionally substituted with the same or different 1 to 2 $C_{1-6}$ alkyl groups, and
(h) $C_{1-6}$ alkyl-carbonylamino,
(2) 5- or 6-membered heteroaryl which may be optionally substituted with the same or different 1 to 4 groups selected from the group consisting of (a) to (h) defined in the above (1), or
(3) a group of the following formula (11), (12), (13), (14), (15), or (16):

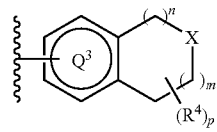

(11)

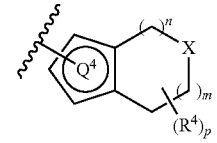

(12)

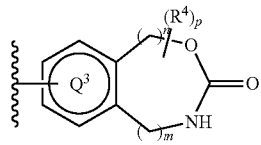

(13)

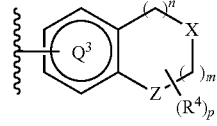

(14)

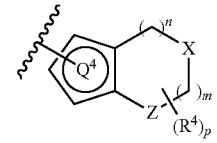

(15)

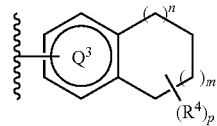

(16)

wherein ring $Q^3$ is optionally-substituted benzene ring, optionally-substituted pyridine ring, optionally-substituted pyrimidine ring, optionally-substituted pyridazine ring, or optionally-substituted pyrazine ring;

ring $Q^4$ is optionally-substituted 5-membered heteroaryl ring;

n and m are independently 0, 1, or 2, provided that n and m are not simultaneously 0;

X and Z are independently $NR^5$, $-NR^{3e}C(O)-$, $-C(O)NR^{3e}-$, or O wherein $R^5$ is hydrogen atom, $C_{1-6}$ alkyl which may be optionally substituted with the same or different 1 to 3 halogen atoms, or $C_{1-6}$ alkylcarbonyl; Rae is hydrogen atom or $C_{1-6}$ alkyl;

p is 1, 2, 3, 4, or 5;

$R^4$ is, independently when two or more exist, hydrogen atom, halogen atom, hydroxy, oxo, $C_{1-6}$ alkyl which may be optionally substituted with the same or different 1 to 3 halogen atoms, or $C_{1-6}$ alkoxy which may be optionally substituted with the same or different 1 to 3 halogen atoms.

Ring $Q^3$ is preferably benzene ring or pyridine ring.

Ring $Q^4$ is preferably imidazole ring, oxazole ring, or thiazole ring; and more preferably thiazole ring.

Ring $Q^2$ is preferably
(1) phenyl which may be optionally substituted with the same or different 1 to 2 groups selected from the group consisting of $C_{1-6}$ alkoxy which may be optionally substituted with hydroxy and $C_{1-6}$ alkyl-carbonylamino,
(2) a group of the following formula (2):

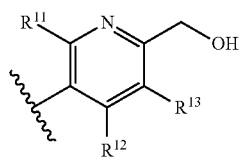

(2)

wherein $R^{11}$, $R^{12}$ and $R^{13}$ are independently
(a) hydrogen atom,
(b) halogen atom,
(c) $C_{1-6}$ alkyl which may be optionally substituted with 1 to 3 fluorine atoms, or
(d) amino which may be optionally substituted with the same or different 1 to 2 $C_{1-6}$ alkyl groups, or
(3) a group of the following formula (21):

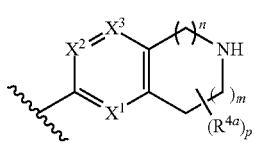

(21)

wherein $X^1$ is N or $CR^{14}$;
$X^2$ is N or $CR^{15}$;
$X^3$ is N or $CR^{16}$;
provided that $X^1$, $X^2$ and $X^3$ are not simultaneously N;
$R^{14}$, $R^{15}$, and $R^{16}$ are independently
(a) hydrogen atom,
(b) halogen atom,
(c) $C_{1-6}$ alkyl which may be optionally substituted with the same or different 1 to 3 halogen atoms, or
(d) alkoxy which may be optionally substituted with the same or different 1 to 3 halogen atoms;

n and m are independently 0, 1, or 2, provided that n and m are not simultaneously 0;

p is 1, 2, 3, 4, or 5;

$R^{4a}$ independently when two or more exist, hydrogen atom, halogen atom, or $C_{1-6}$ alkyl which may be optionally substituted with the same or different 1 to 3 halogen atoms.

Ring $Q^2$ is furthermore preferably
(1) acetylaminophenyl,
(2) 6-hydroxymethylpyridin-3-yl wherein the pyridine moiety thereof may be optionally further substituted with $C_{1-4}$ alkyl which may be optionally substituted with 1 to 3 fluorine atoms, or amino, or
(3) a group of the following formula (21):

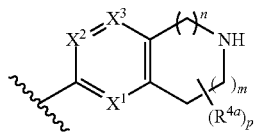

(21)

wherein $X^1$ is N, CH, or CF;
$X^2$ is N, CH, or CF;
$X^3$ is N, CH, or CF;
provided that $X^1$, $X^2$ and $X^3$ are not simultaneously N;
n is 1;
m is 0 or 1;
p is 1 or 2;
$R^{4a}$ is, independently when two or more exist, hydrogen atom or methyl.

The present compound may be in the forms of a hydrate and/or a solvate. Thus, the present compound also encompasses the hydrate and/or the solvate such as ethanol solvate. Furthermore, the present compound encompasses all types of crystal forms of the present compound.

Specific examples of the salt of the compound of formula (1) include an inorganic acid salt such as hydrochloride, hydrobromide, sulfate, phosphate, and nitrate; and an organic acid salt such as acetate, propionate, oxalate, succinate, lactate, malate, tartrate, citrate, maleate, fumarate, methanesulfonate, p-toluenesulfonate, benzenesulfonate, and ascorbate.

The compound of formula (1) may be in the form of a tautomer. Thus, the present compound also encompasses the tautomer of the compound of formula (1).

The compound of formula (1) may contain one or more asymmetric carbon atoms. Thus, the present compound encompasses not only racemic forms of the compound of formula (1) but also optically-active forms thereof. When the compound of formula (1) contains two or more asymmetric carbon atoms, the compound can result in various stereoisomerisms. Thus, the present compound also encompasses the stereoisomer of the compound and a mixture or isolate thereof.

Also, the compound of formula (1) encompasses the compound wherein one or more of $^1H$ are replaced with $^2H(D)$ (i.e. deuterated form).

Hereinafter, the preparations of the compound of formula (1) are illustrated with some examples, but the invention should not be limited thereto.

The compound of formula (1) can be prepared according to processes shown below and according to the processes in combination with known compounds and known synthesis processes.

As appropriate, each compound used as a starting compound may be used in the salt form. The shown processes are just examples to prepare the compounds, and may be optionally modified by those skilled in the organic synthesis field.

In each process shown below, any functional groups which need to be protected may be optionally protected and then deprotected after the reaction or reactions are completed to give the desired compound even though the use of protective groups is not specifically described.

The protective group used herein includes any conventional groups described in various literatures, for example, T. W. Greene and P. G. M. Wuts, "Protective Groups in Organic Synthesis", 3rd Ed., John Wiley and Sons, inc., New York (1999). In more detail, specific examples of the protective groups for amino group include benzyloxycarbonyl, tert-butoxycarbonyl, acetyl, and benzyl, and specific examples of the protective groups for hydroxy group include trialkylsilyl, acetyl, and benzyl.

The protective groups can be introduced and cleaved according to commonly-used methods in synthetic organic chemistry (e.g. the method described in T. W. Greene and P. G. M. Wuts, "Protective Groups in Organic Synthesis", 3rd Ed., John Wiley and Sons, inc., New York (1999)) and similar methods thereto.

Preparation 1

One of the compounds of formula (1), the compound of formula (1-7) is prepared by linking each fragment in positions a and b, respectively.

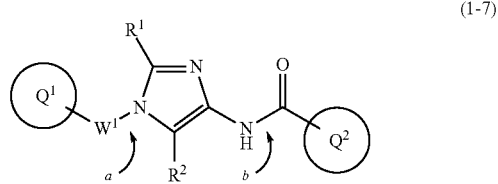

wherein $W^1$, $R^1$, $R^2$, ring $Q^1$, and ring $Q^2$ are as defined in the above [1].

The processes for forming each bond in positions a and b can be illustrated as follows, but the order of procedure for forming each bond may be optionally changed:

(e.g., New Version of Heterocyclic Compound (advanced level) edited by Kodansha Scientific Ltd.).

Step 1-1: Preparation Process of Compound (1-2)

Compound (1-2) is prepared by hydrolyzing compound (1-1) according to a similar process to a known process (e.g., Protective Groups in Organic Synthesis $3^{rd}$ Edition (John Wiley & Sons, Inc.), Comprehensive Organic Transformation, by R. C. Larock, VCH publisher Inc., 1989).

Step 1-2: Preparation Process of Compound (1-5)

Compound (1-5) is prepared by the alkylation reaction of compounds (1-3) and (1-4) in an inert solvent in the presence of a base.

Specific examples of the base include an organic base such as triethylamine, diisopropylethylamine, and pyridine; an inorganic base such as potassium carbonate, sodium carbonate, cesium carbonate, potassium hydrogen carbonate, sodium hydrogen carbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and a metal alkoxide such as sodium methoxide and potassium tert-butoxide.

Specific examples of the inert solvent include a halogenated hydrocarbon such as chloroform and dichloromethane; an aromatic hydrocarbon such as toluene; an ether-type solvent such as diethyl ether, tetrahydrofuran (THF), and 1,4-dioxane; an aprotic polar solvent such as acetonitrile, acetone, methyl ethyl ketone, N,N-dimethylformamide, N-methyl-2-pyrrolidinone, and dimethyl sulfoxide; a basic solvent such as pyridine; and a mixture thereof.

The reaction temperature is typically 0° C. to 150° C., preferably 20° C. to 100° C., but is not limited thereto. The reaction time is typically 30 minutes to 48 hours, preferably 30 minutes to 10 hours.

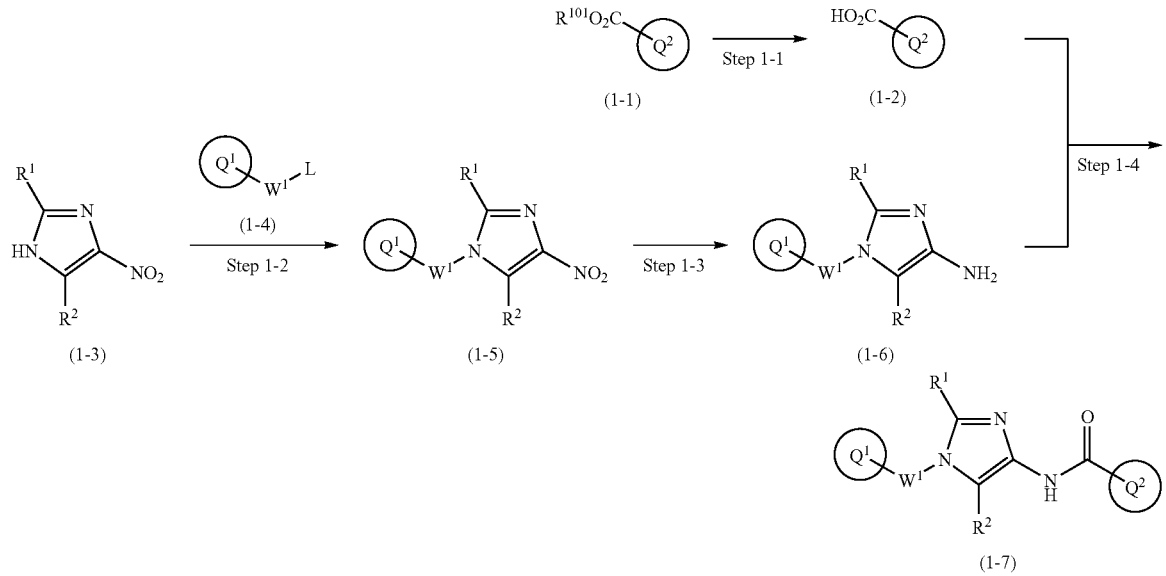

wherein $W^1$, $R^1$, $R^2$, ring $Q^1$, and ring $Q^2$ are as defined in the above [1]; $R^{101}$ is $C_{1-6}$ alkyl; L is a leaving group (such as iodine atom, bromine atom, chlorine atom, and substituted sulfonyloxy (e.g., methanesulfonyloxy and p-toluenesulfonyloxy)).

Compound (1-1) may be a commercially available product or be prepared according to known synthesis processes Step 1-3: Preparation Process of Compound (1-6)

Compound (1-6) is prepared by reducing the nitro group in compound (1-5). For example, reductions under an acidic condition with a metal such as zinc, iron, and tin or a metal salt such as tin (II) chloride; reductions with a sulfide such as sodium hypodisulfite ($Na_2S_2O_4$); and catalytic hydrogenations with a metal catalyst such as palladium/carbon, Raney nickel, platinum oxide/carbon, and rhodium/carbon under hydrogen atmosphere may be used.

In the reduction with a metal or a metal salt, the amount of the metal or metal salt to be used is typically about 1 mole to 100 moles, preferably about 10 moles to 30 moles per mole of compound (1-5). Also, the amount of the acid to be used is typically about 1 mole to 100 moles, preferably about 10 moles to 30 moles per mole of compound (1-5). The reduction is typically carried out in a solvent which has no negative effect on the reaction (e.g. ethanol). The reaction temperature is typically 0° C. to 100° C., but is not limited thereto. The reaction time is typically 30 minutes to 8 hours.

In the catalytic hydrogenation reaction, the amount of the metal catalyst to be used for compound (1-5) is typically 0.1% by weight to 1000% by weight, preferably 1% by weight to 100% by weight. The reaction may be carried out in a solvent such as an alcohol such as methanol; an ether such as tetrahydrofuran; and an ester such as ethyl acetate. The hydrogen pressure is typically 1 atm to 100 atms, preferably 1 atm to 5 atms. The reaction temperature is typically 0° C. to 120° C., preferably 20° C. to 80° C., but is not limited thereto. The reaction time is typically 30 minutes to 72 hours, preferably 1 hour to 48 hours.

Also, the reaction may be carried out in the presence of an acid catalyst, as appropriate. For example, an organic acid such as formic acid, acetic acid, and trifluoroacetic acid, and an inorganic acid such as sulfuric acid, hydrochloric acid, and hydrobromic acid are used as the acid catalyst. The amount of the acid to be used is 0.1 mole or more per mole of compound (1-5).

Step 1-4: Preparation Process of Compound (1-7)

Compound (1-7) is prepared by reacting compound (1-2) with compound (1-6) in an inert solvent in the presence of a condensation agent.

The reaction may be carried out in the presence of a base, as appropriate. The reaction temperature is typically about −20° C. to the boiling point of the used solvent, but is not limited thereto. The reaction time is typically 10 minutes to 48 hours, which may vary according to various conditions such as a reaction temperature, a condensation agent, a starting material, and a solvent to be used.

Specific examples of the condensation agent include dicyclohexylcarbodiimide (DCC), diisopropylcarbodiimide (DIPC), 1-ethyl-3-(3-dimethylaminopropyl)-carbodiimide (WSC), benzotriazol-1-yloxytris(dimethylamino)phosphonium hexafluorophosphate (BOP), diphenylphosphoryl azide (DPPA), N,N'-carbonyldiimidazole (CDI), O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), and diphenyl chlorophosphate. As appropriate, the reaction may be carried out with the addition of an additive such as N-hydroxysuccinimide (HOSu), 1-hydroxybenzotriazole (HOBt), and 3-hydroxy-4-oxo-3,4-dihydro-1,2,3-benzotriazine (HOOBt).

Specific examples of the base include an organic base such as triethylamine, diisopropylethylamine, and pyridine; an inorganic base such as potassium carbonate, sodium carbonate, cesium carbonate, potassium hydrogen carbonate, sodium hydrogen carbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and a metal alkoxide such as sodium methoxide and potassium tert-butoxide.

Specific example of the inert solvent include a halogenated hydrocarbon such as chloroform and dichloromethane; an aromatic hydrocarbon such as toluene; an ether-type solvent such as diethyl ether, tetrahydrofuran (THF), and 1,4-dioxane; an aprotic polar solvent such as acetonitrile, acetone, methyl ethyl ketone, dimethylformamide, N-methyl-2-pyrrolidinone, and dimethyl sulfoxide; a basic solvent such as pyridine; and a mixture thereof.

Compound (1-7) is also prepared by reacting compound (1-6) with an acid halide or an acid anhydride derived from compound (1-2) in an inert solvent in the presence of a base.

Preparation 2

One of the compounds of formula (1), the compound of formula (2-4) is prepared according to, for example, the following process:

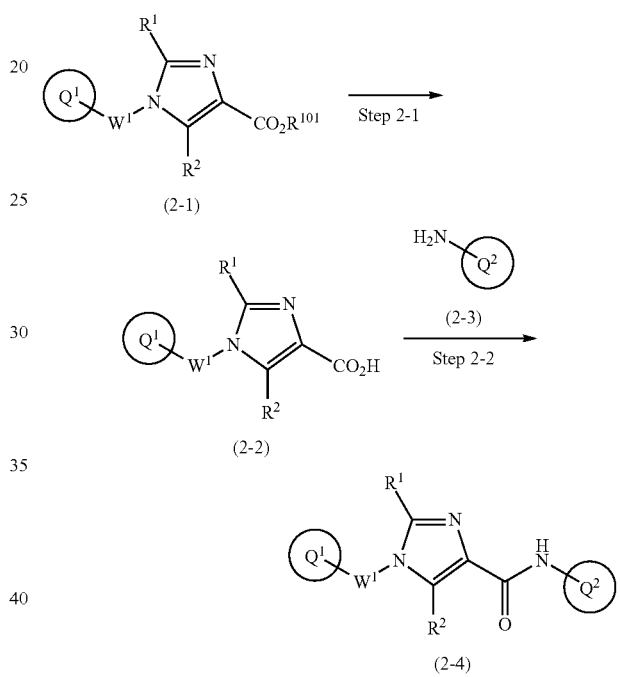

wherein $W^1$, $R^1$, $R^2$, ring $Q^1$, and ring $Q^2$ are as defined in the above [1]; and $R^{101}$ is $C_{1-6}$ alkyl.

Compound (2-1) may be a commercially available product or be prepared according to known synthesis processes (e.g., WO 2014/125444).

Step 2-1: Preparation Process of Compound (2-2)

Compound (2-2) is prepared by hydrolyzing compound (2-1) according to a similar process to a known process (e.g., Protective Groups in Organic Synthesis $3^{rd}$ Edition (John Wiley & Sons, Inc.), Comprehensive Organic Transformation, by R. C. Larock, VCH publisher Inc., 1989).

Step 2-2: Preparation Process of Compound (2-4)

Compound (2-4) is prepared from compounds (2-2) and (2-3) according to the process of Step 1-4.

Preparation 3

One of the compounds of formula (1), the compound of formula (1-7) is prepared according to, for example, the following process:

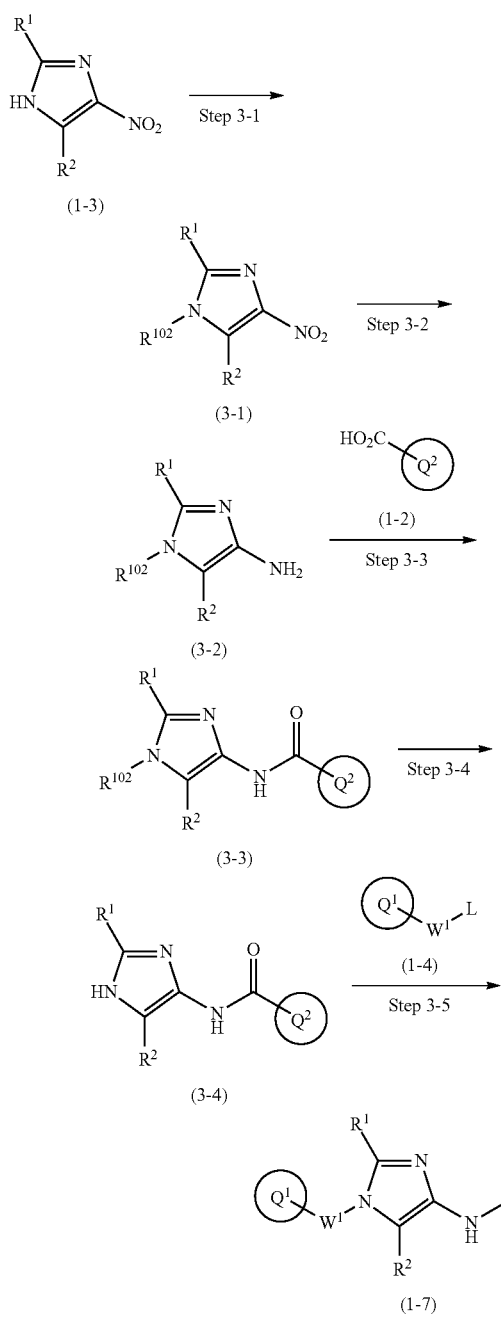

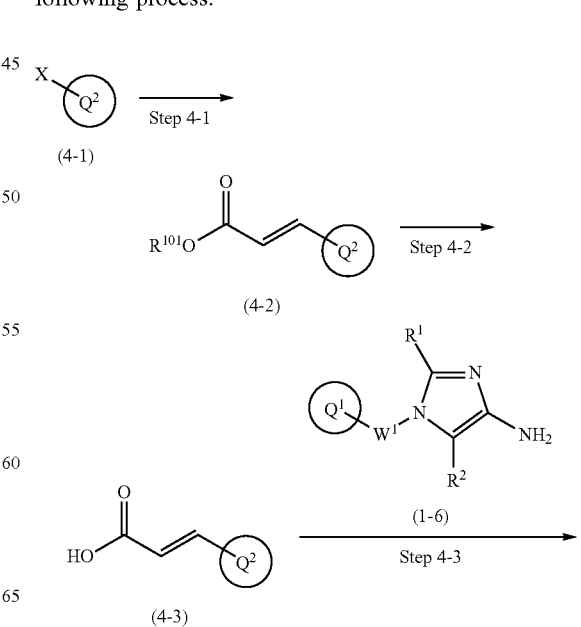

Examples of the base include potassium carbonate, sodium carbonate, cesium carbonate, potassium tert-butoxide, sodium hydride, sodium bis(trimethylsilyl)amide, lithium bis(trimethylsilyl)amide, potassium bis(trimethylsilyl)amide, and lithium diisoproylamide.

Examples of the inert solvent include DMF, THF, acetonitrile, and a mixture thereof.

The reaction temperature is typically 0° C. to 150° C., preferably 0° C. to 100° C., but is not limited thereto. The reaction time is typically 10 minutes to 24 hours, preferably 20 minutes to 6 hours.

Step 3-2: Preparation Process of Compound (3-2)

Compound (3-2) is prepared from compound (3-1) according to the process of Step 1-3.

Step 3-3: Preparation Process of Compound (3-3)

Compound (3-3) is prepared from compounds (3-2) and (1-2) according to the process of Step 1-4.

Step 3-4: Preparation Process of Compound (3-4)

Compound (3-4) is prepared by cleaving the protective group in nitrogen atom of imidazole group in compound (3-3) in an inert solvent.

For example, when 2-(trimethylsilyl)ethoxymethyl group is cleaved, compound (3-4) is prepared by reacting compound (3-3) with an acid or a fluorinating reagent.

Examples of the acid include TFA, formic acid, hydrochloric acid, sulfuric acid, p-toluenesulfonic acid, methanesulfonic acid, and (±) 10-camphorsulfonic acid.

Examples of the fluorinating reagent include hydrofluoric acid and tetrabutylammonium fluoride.

Examples of the solvent used include dichloromethane, 1,2-dichloroethane, 1,4-dioxane, THF, toluene, ethyl acetate, methanol, ethanol, 2-propanol, and a mixture thereof.

The reaction temperature is typically 0° C. to 150° C., preferably 0° C. to 50° C., but is not limited thereto. The reaction time is typically 5 minutes to 24 hours, preferably 1 hour to 9 hours.

Step 3-5: Preparation Process of Compound (1-7)

Compound (1-7) is prepared from compounds (3-4) and (1-4) according to the process of Step 1-2.

Preparation 4

One of the compounds of formula (1), the compound of formula (4-4) is prepared according to, for example, the following process:

wherein $W^1$, $R^1$, $R^2$, ring $Q^1$, and ring $Q^2$ are as defined in the above [1]; $R^{102}$ is a protective group; L is a leaving group (such as iodine atom, bromine atom, chlorine atom, and substituted sulfonyloxy (e.g., methanesulfonyloxy and p-toluenesulfonyloxy)).

Step 3-1: Preparation Process of Compound (3-1)

Compound (3-1) is prepared by introducing a protective group to nitrogen atom of imidazole group in compound (1-3) in an inert solvent. Examples of the protective group include 2-(trimethylsilyl)ethoxymethyl, benzyloxycarbonyl, tert-butoxycarbonyl, acetyl, and benzyl.

For example, when 2-(trimethylsilyl)ethoxymethyl group is introduced, compound (3-1) is prepared by reacting compound (1-3) with 2-(trimethylsilyl)ethoxymethyl chloride in an inert solvent in the presence of a base.

-continued (4-4)

wherein $W^1$, $R^1$, $R^2$, ring $Q^1$, and ring $Q^2$ are as defined in the above [1]; $R^{101}$ is $C_{1-6}$ alkyl; and X is halogen atom.

Step 4-1: Preparation Process of Compound (4-2)

Compound (4-2) is prepared by reacting compound (4-1) with acrylate in an inert solvent in the presence of a palladium catalyst and a base.

Specific examples of the palladium catalyst include tetrakis(triphenylphosphine)palladium (O), dichlorodi(tri(o-tolylphosphine))palladium, bis(dibenzylideneacetone)palladium (O), tris(dibenzylideneacetone)dipalladium (O), bis(tri-tert-butylphosphine)palladium (O), [1,1'-bis(diphenylphosphino)ferrocene]palladium (II) dichloride.

Specific examples of the base include an inorganic base such as potassium carbonate, sodium carbonate, cesium carbonate, potassium phosphate, potassium hydroxide, and sodium hydroxide, triethylamine, and diisopropylethylamine.

Examples of the inert solvent include THF, acetonitrile, propionitrile, toluene, 1,2-dimethoxyethane, 1,4-dioxane, DMF, water, and a mixture thereof.

The reaction temperature is typically 50° C. to 150° C., preferably 80° C. to 120° C., but is not limited thereto. The reaction may be carried out under microwave irradiation. The reaction time is typically 1 hour to 24 hours, preferably 2 hours to 12 hours.

Step 4-2: Preparation Process of Compound (4-3)

Compound (4-3) is prepared by hydrolyzing compound (4-2) according to a similar process to a known process (e.g., Protective Groups in Organic Synthesis 3$^{rd}$ Edition (John Wiley & Sons, Inc.), Comprehensive Organic Transformation, by R. C. Larock, VCH publisher Inc., 1989).

Step 4-3: Preparation Process of Compound (4-4)

Compound (4-4) is prepared from compounds (4-3) and (1-6) according to the process of Step 1-4.

Preparation 5

One of the compounds of formula (1), the compound of formula (5-5) is prepared according to, for example, the following process:

(5-1)

(5-3)

-continued (5-4)

(5-5)

wherein ring $Q^2$ is as defined in the above [1]; A is boronic acid or boronate; $R^{101}$ is $C_{1-6}$ alkyl; $R^a$ and $R^b$ are independently the same or different hydrogen atom or methyl; X is halogen atom.

Step 5-1: Preparation Process of Compound (5-3)

Compound (5-3) is prepared by reacting compound (5-1) with compound (5-2) in an inert solvent in the presence of a palladium catalyst and a base.

Specific examples of the palladium catalyst include tetrakis(triphenylphosphine)palladium (O), bis(dibenzylideneacetone)palladium (O), tris(dibenzylideneacetone)dipalladium (O), bis(tri-tert-butylphosphine)palladium (O), [1,1'-bis(diphenylphosphino) ferrocene]palladium (II) dichloride.

Specific examples of the base include potassium carbonate, sodium carbonate, cesium carbonate, potassium phosphate, potassium hydroxide, and sodium hydroxide.

Examples of the inert solvent include THF, toluene, 1,2-dimethoxyethane, 1,4-dioxane, DMF, water, and a mixture thereof.

The reaction temperature is typically 50° C. to 150° C., preferably 80° C. to 120° C., but is not limited thereto. The reaction may be carried out under microwave irradiation. The reaction time is typically 1 hour to 24 hours, preferably 2 hours to 12 hours.

Step 5-2: Preparation Process of Compound (5-4)

Compound (5-4) is prepared by reacting compound (5-3) with osmium tetroxide solution (immobilized catalyst, including microencapsulated osmium tetroxide) or potassium osmate (IV) dihydrate in the presence of sodium periodate.

Examples of the solvent used include acetone, 1,4-dioxane, THF, tert-butanol, water, and a mixture thereof.

The reaction temperature is typically 0° C. to 100° C., preferably 25° C. to 50° C., but is not limited thereto. The reaction time is typically 1 hour to 72 hours, preferably 1 hour to 24 hours.

Also, compound (5-4) is prepared by treating compound (5-3) with oxygen currents including ozone and then reacting the treated compound with a reducing agent such as dimethyl sulfide in a solvent such as dichloromethane, ethyl acetate, and methanol. The reaction temperature is typically −78° C. to room temperature, but is not limited thereto. The reaction time is typically 1 hour to 72 hours, preferably 6 hours to 24 hours.

Step 5-3: Preparation Process of Compound (5-5)

Compound (5-5) is prepared by reacting compound (5-4) with a hydride reducing agent or an organometallic reagent.

Specific examples of the hydride reducing agent include sodium borohydride and sodium cyanoborohydride.

The solvent used in the reaction with the hydride reducing agent includes methanol, ethanol, dichloromethane, toluene, and a mixture thereof.

The reaction temperature is typically −78° C. to 50° C., preferably 0° C. to 25° C., but is not limited thereto. The reaction time is typically 5 minutes to 12 hours, preferably 30 minutes to 6 hours.

Specific examples of the organometallic reagent include methylmagnesium bromide, methylmagnesium iodide, and methyllithium.

Examples of the solvent used in the reaction with the organometallic reagent include THF, diethyl ether, and a mixture thereof.

The reaction temperature is typically −78° C. to 25° C., preferably −40° C. to 0° C., but is not limited thereto. The reaction time is typically 5 minutes to 12 hours, preferably 30 minutes to 6 hours.

Preparation 6

The compound of formula (6-5) is prepared according to, for example, the following process:

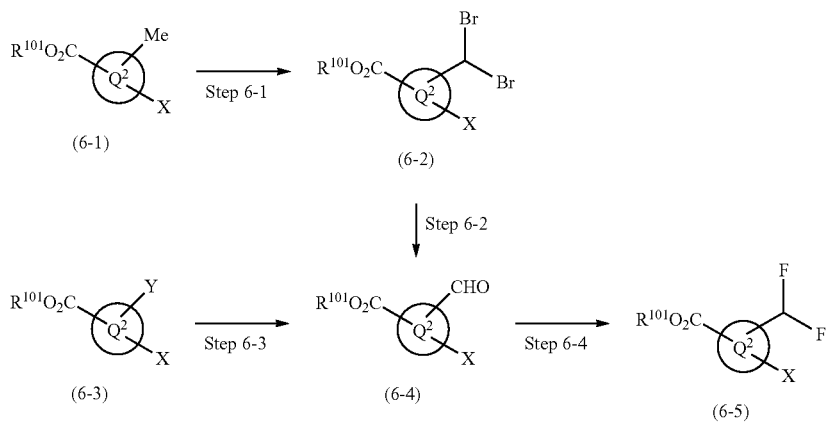

wherein ring $Q^2$ is as defined in the above [1]; $R^{101}$ is $C_{1-6}$ alkyl; X is halogen atom; and Y is bromine atom or iodine atom.

Step 6-1: Preparation Process of Compound (6-2)

Compound (6-2) is prepared by reacting compound (6-1) with a brominating agent in an inert solvent in the presence of a radical initiator.

Specific examples of the radical initiator include azobisisobutyronitrile (AIBN) and benzoyl peroxide (BPO).

Specific examples of the brominating agent include N-bromosuccinimide and bromine.

Examples of the inert solvent include carbon tetrachloride, chlorobenzene, and a mixture thereof.

The reaction temperature is typically 50° C. to 150° C., preferably 80° C. to 120° C., but is not limited thereto. The reaction time is typically 3 hours to 48 hours, preferably 4 hours to 12 hours.

Step 6-2: Preparation Process of Compound (6-4)

Compound (6-4) is prepared by reacting compound (6-2) with silver nitrate in an inert solvent.

Specific examples of the inert solvent include acetonitrile, THF, 1,4-dioxane, and a mixture thereof.

The reaction temperature is typically 50° C. to 150° C., preferably 80° C. to 120° C., but is not limited thereto. The reaction time is typically 3 hours to 48 hours, preferably 4 hours to 12 hours.

Step 6-3: Preparation Process of Compound (6-4)

Compound (6-4) is also prepared by reacting compound (6-3) with an organometallic reagent and then treating the resulting compound with a formylating agent.

Examples of the organometallic reagent include isopropylmagnesium chloride-lithium chloride complex, isopropylmagnesium chloride, and n-butyllithium.

Examples of the solvent used include THF, diethyl ether, toluene, and a mixture thereof.

Examples of the formylating agent include DMF and N-formylmorpholine.

The reaction temperature is typically −78° C. to 50° C., preferably −30° C. to 25° C., but is not limited thereto. The reaction time is typically 30 minutes to 24 hours, preferably 1 hour to 6 hours.

Step 6-4: Preparation Process of Compound (6-5)

Compound (6-5) is prepared by reacting compound (6-4) with a deoxofluorinating agent in an inert solvent.

Specific examples of the deoxofluorinating agent include diethylaminosulfur trifluoride (DAST), bis(2-methoxyethyl) aminosulfur trifluoride (Deoxo-Fluor®), XtalFluor-E®, XtalFluor-M®, and 4-tert-butyl-2,6-dimethylphenylsulfur trifluoride (Fluolead®). As appropriate, compounds such as diazabicycloundecene (DBU), triethylamine trihydrofluoride, and triethylamine dihydrofluoride may be used as a promoter.

Specific examples of the inert solvent include dichloromethane, 1,2-dichloroethane, toluene, THF, and a mixture thereof.

The reaction temperature is typically −20° C. to 50° C., preferably 0° C. to 25° C., but is not limited thereto. The reaction time is typically 10 minutes to 12 hours, preferably 30 minutes to 3 hours.

Compound (6-5) is also prepared by reacting compound (6-4) with sulfur tetrafluoride.

Preparation 7

One of the compounds of formula (1), the compound of formula (7-3) is prepared according to, for example, the following process:

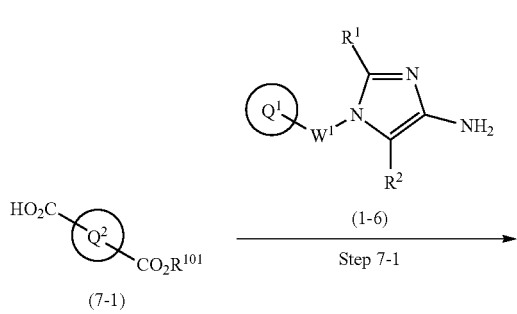

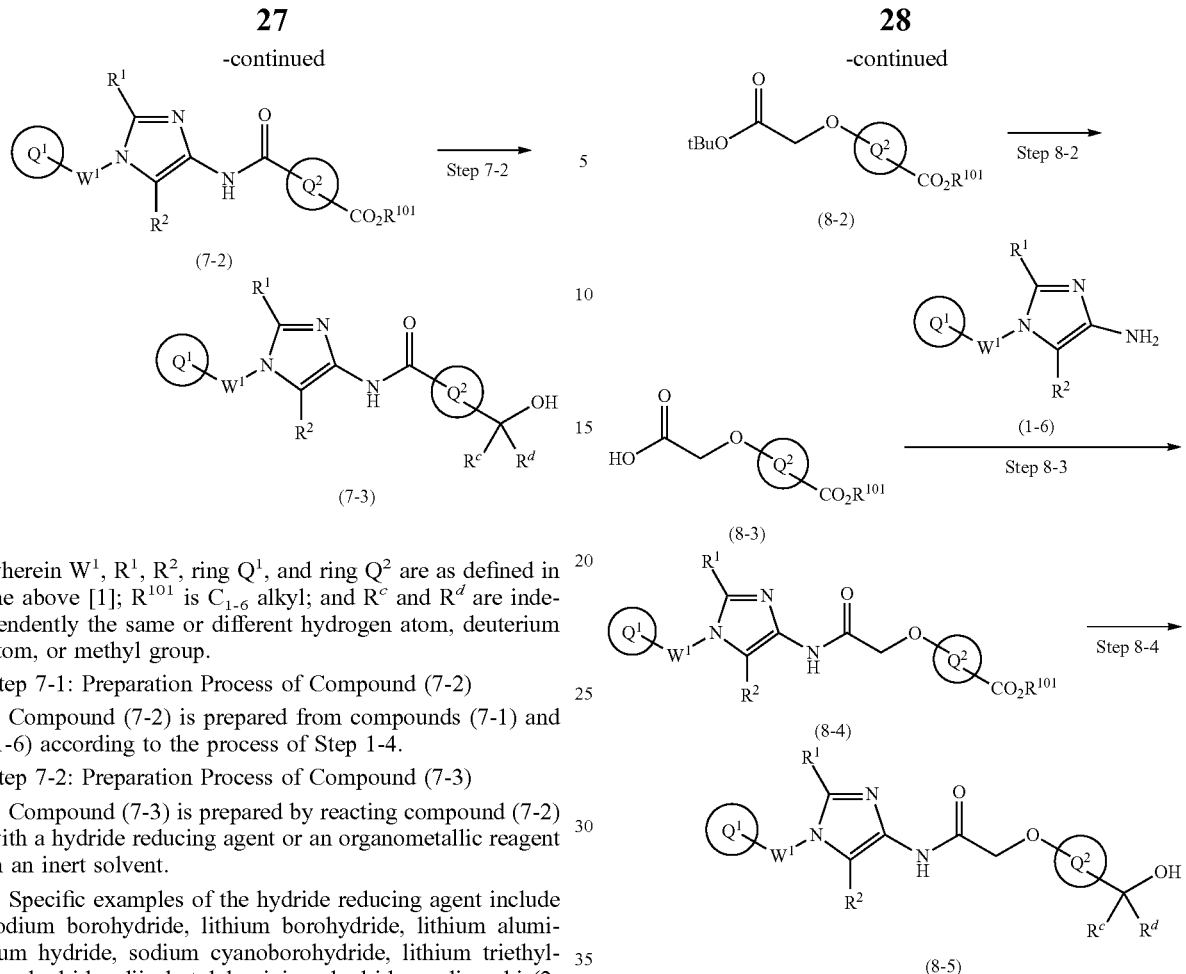

wherein $W^1$, $R^1$, $R^2$, ring $Q^1$, and ring $Q^2$ are as defined in the above [1]; $R^{101}$ is $C_{1-6}$ alkyl; and $R^c$ and $R^d$ are independently the same or different hydrogen atom, deuterium atom, or methyl group.

Step 7-1: Preparation Process of Compound (7-2)

Compound (7-2) is prepared from compounds (7-1) and (1-6) according to the process of Step 1-4.

Step 7-2: Preparation Process of Compound (7-3)

Compound (7-3) is prepared by reacting compound (7-2) with a hydride reducing agent or an organometallic reagent in an inert solvent.

Specific examples of the hydride reducing agent include sodium borohydride, lithium borohydride, lithium aluminum hydride, sodium cyanoborohydride, lithium triethylborohydride, diisobutylaluminium hydride, sodium bis(2-methoxyethoxy)aluminium hydride, lithium borodeuteride, and lithium aluminum deuteride. Examples of the solvent used include methanol, ethanol, dichloromethane, toluene, and a mixture thereof.

The reaction temperature is typically −78° C. to 25° C., preferably 0° C. to 25° C., but is not limited thereto. The reaction time is typically 5 minutes to 12 hours, preferably 30 minutes to 6 hours.

Specific examples of the organometallic reagent include methylmagnesium bromide, methylmagnesium iodide, and methyllithium.

Examples of the solvent used in the reaction with the organometallic reagent include THF, diethyl ether, and a mixture thereof.

The reaction temperature is typically −78° C. to 50° C., preferably 0° C. to 25° C., but is not limited thereto. The reaction time is typically 5 minutes to 12 hours, preferably 30 minutes to 6 hours.

Preparation 8

One of the compounds of formula (1), the compound of formula (8-5) is prepared according to, for example, the following process:

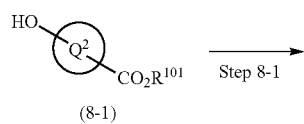

wherein $W^1$, $R^1$, $R^2$, ring $Q^1$, and ring $Q^2$ are as defined in [1]; $R^{101}$ is $C_{1-6}$ alkyl; and $R^c$ and $R^d$ are independently the same or different hydrogen atom, deuterium atom; or methyl.

Step 8-1: Preparation Process of Compound (8-2)

Compound (8-2) is prepared by reacting compound (8-1) with a haloacetate in an inert solvent in the presence of a base.

Specific examples of the haloacetate include tert-butyl chloroacetate, tert-butyl bromoacetate, and tert-butyl iodoacetate.

Examples of the base include potassium carbonate, sodium carbonate, cesium carbonate, potassium tert-butoxide, sodium hydride, sodium bis(trimethylsilyl)amide, lithium bis(trimethylsilyl)amide, potassium bis(trimethylsilyl)amide, and lithium diisopropylamide.

Examples of the inert solvent include DMF, THF, acetonitrile, and a mixture thereof.

The reaction temperature is typically 25° C. to 150° C., preferably 70° C. to 100° C., but is not limited thereto. The reaction time is typically 10 minutes to 12 hours, preferably 20 minutes to 6 hours.

Step 8-2: Preparation Process of Compound (8-3)

Compound (8-3) is prepared by cleaving tert-butyl ester group in compound (8-2) under an acid condition.

Examples of the acid used in the deprotection step include hydrochloric acid, sulfuric acid, HBr, HI, and TFA.

Examples of the solvent used include methanol, ethanol, dichloromethane, 1,2-dichloroethane, THF, 1,4-dioxane, ethyl acetate, and a mixture thereof.

The reaction temperature is typically 0° C. to 100° C., preferably 25° C. to 50° C., but is not limited thereto. The reaction time is typically 1 hour to 24 hours, preferably 2 hours to 12 hours.

Step 8-3: Preparation Process of Compound (8-4)

Compound (8-4) is prepared from compounds (8-3) and (1-6) according to the process of Step 1-4.

Step 8-4: Preparation Process of Compound (8-5)

Compound (8-5) is prepared from compound (8-4) according to the process of Step 7-2.

Preparation 9

The compound of formula (9-4) is prepared according to, for example, the following process:

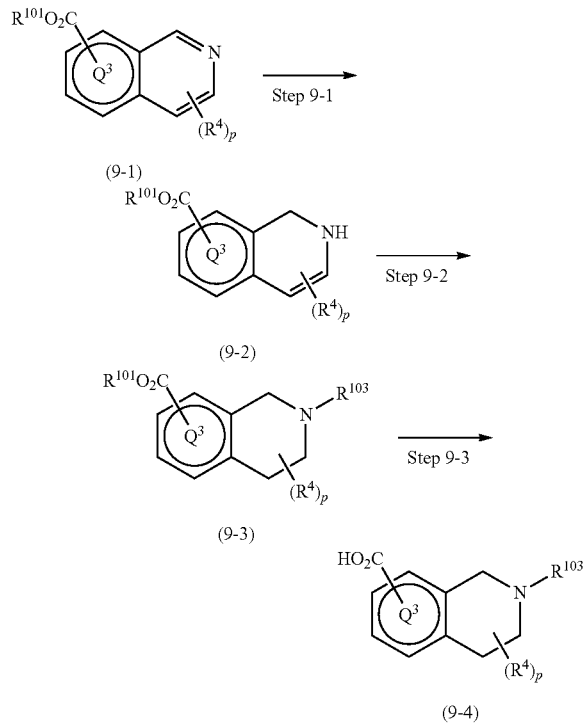

wherein $R^4$, p, and ring $Q^3$ are as defined in the above [6]; $R^{101}$ is $C_{1-6}$ alkyl; and $R^{103}$ is Cbz, Boc, benzyl, 4-methoxybenzyl, or Fmoc.

Compound (9-1) may be a commercially available product.

Step 9-1: Preparation Process of Compound (9-2)

Compound (9-2) is prepared by reacting compound (9-1) with a hydride reducing agent in an inert solvent.

Specific examples of the hydride reducing agent include sodium borohydride, sodium cyanoborohydride, borane, and hydride aluminium hydride.

Examples of the solvent to be used in the reaction with the hydride reducing agent include methanol, ethanol, dichloromethane, toluene, tetrahydrofuran, and a mixture thereof.

The reaction temperature is typically −78° C. to 100° C., preferably 0° C. to 50° C., but is not limited thereto. The reaction time is typically 5 minutes to 12 hours, preferably 30 minutes to 6 hours.

Step 9-2: Preparation Process of Compound (9-3)

Compound (9-3) is prepared by reducing olefin in compound (9-2) with a reagent for introducing a protective group. For example, reactions such as catalytic hydrogenation reaction with a metal catalyst such as palladium/carbon, Raney nickel, platinum oxide/carbon, and rhodium/carbon under hydrogen atmosphere in the presence of $Boc_2O$ are used.

In the catalytic hydrogenation reaction, the amount of the metal catalyst to be used for compound (9-2) is typically 0.1% by weight to 1000% by weight, preferably 1% by weight to 100% by weight. The reaction may be carried out in a solvent such as an alcohol such as methanol; an ether such as tetrahydrofuran; and an ester such as ethyl acetate. The hydrogen pressure is typically 1 atm to 100 atms, preferably 1 atm to 5 atms. The reaction temperature is typically 0° C. to 120° C., preferably 20° C. to 80° C., but is not limited thereto. The reaction time is typically 30 minutes to 72 hours, preferably 1 hour to 48 hours.

When $R^{103}$ is benzyl group, 4-methoxybenzyl group, etc., compound (9-3) can be directly prepared through a pyridinium salt intermediate of compound (9-1). For example, compound (9-3) is prepared by reducing the pyridinium salt of compound (9-1) synthesized by reacting compound (9-1) with a reagent such as benzyl bromide. Reduction reactions such as reduction with a hydride reducing agent and catalytic hydrogenation with a metal catalyst such as palladium/carbon, Raney nickel, platinum oxide/carbon, and rhodium/carbon under hydrogen atmosphere are used.

Step 9-3: Preparation Process of Compound (9-4)

Compound (9-4) is prepared by hydrolyzing compound (9-3) according to a similar process to a known process (e.g. Protective Groups in Organic Synthesis $3^{rd}$ Edition (John Wiley & Sons, Inc.), Comprehensive Organic Transformation, by R. C. Larock et al., VCH publisher Inc., 1989).

Preparation 10

The compound of formula (10-5) is prepared according to, for example, the following process:

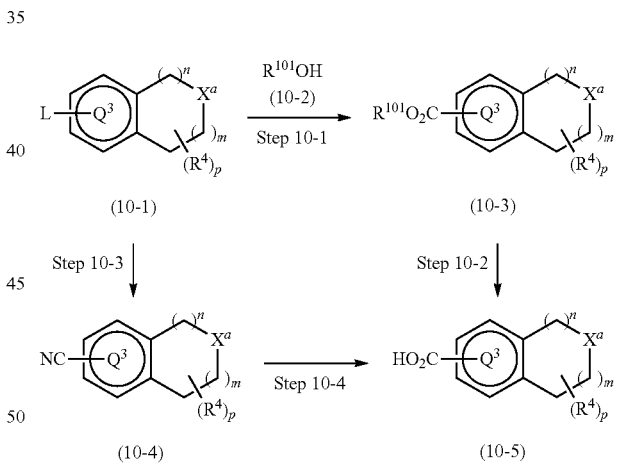

wherein $R^4$, n, m, p, and ring $Q^3$ are as defined in the above [6]; $R^{101}$ is $C_{1-6}$ alkyl; $X^a$ is O or $NR^{103}$; $R^{103}$ is Cbz, Boc, benzyl, 4-methoxybenzyl, or Fmoc; L is a leaving group (such as iodine atom, bromine atom, chlorine atom, and substituted sulfonyl (e.g., methanesulfonyl and p-toluenesulfonyl)).

Compound (10-1) may be a commercially available product or be prepared according to known synthesis processes (e.g., WO 2009/056556, WO 2006/065215).

Step 10-1: Preparation Process of Compound (10-3)

Compound (10-3) is prepared by introducing ester group to compound (10-1) under carbon monoxide atmosphere in the presence of a palladium catalyst, phosphorus ligand, an alcohol of formula (10-2) in an inert solvent.

The pressure of carbon monoxide is selected according to various conditions such as a reaction temperature, a starting material, and a solvent to be used, as appropriate, and is typically 1 atm to 100 atms, preferably 1 atm to 5 atms. The reaction temperature is typically about −20° C. to the boiling point of the used solvent, preferably room temperature to the boiling point of the used solvent. The reaction time is typically 10 minutes to 48 hours, which may vary according to various conditions such as a reagent, a reaction temperature, a starting material, and a solvent to be used.

Examples of the palladium catalyst include tetrakis(triphenylphosphine)palladium and di-tert-butylphosphinepalladium.

Examples of the inert solvent include N,N-dimethylformamide, N-methyl-2-pyrrolidinone, 1,4-dioxane, and a mixture thereof.

In addition, an organic base such as N,N-diisopropylethylamine and triethylamine may be added thereto, as appropriate.

Step 10-2: Preparation Process of Compound (10-5)

Compound (10-5) is prepared by hydrolyzing compound (10-3) according to a similar process to a known process (e.g. Protective Groups in Organic Synthesis 3$^{rd}$ Edition (John Wiley & Sons, Inc.), Comprehensive Organic Transformation, by R. C. Larock et al., VCH publisher Inc., 1989).

Step 10-3: Preparation Process of Compound (10-4)

Compound (10-4) is prepared by the cyanation of compound (10-1) in an inert solvent in the presence of a palladium catalyst, phosphorus ligand, and a cyanating agent.

The reaction temperature is typically about −20° C. to the boiling point of the used solvent, preferably room temperature to the boiling point of the used solvent. The reaction may be carried out using a microwave reaction device. The reaction time is typically 10 minutes to 48 hours, which may vary according to various conditions such as a reaction temperature, a reagent, a starting material, and a solvent to be used.

Examples of the cyanating agent include sodium cyanide, potassium cyanide, zinc cyanide, and copper (I) cyanide, preferably zinc cyanide.

Examples of the palladium catalyst include tetrakis(triphenylphosphine)palladium and di-tert-butylphosphinepalladium.

Examples of the inert solvent include N,N-dimethylformamide, N-methyl-2-pyrrolidinone, 1,4-dioxane and a mixture thereof.

Step 10-4: Preparation Process of Compound (10-5)

Compound (10-5) is prepared by hydrolyzing cyano group of compound (10-4) in an appropriate solvent in the presence of a base.

The reaction temperature is typically about −20° C. to the boiling point of the used solvent, preferably room temperature to the boiling point of the used solvent. The reaction time is typically 10 minutes to 48 hours, which may vary according to various conditions such as a reaction temperature, a starting material, and a solvent to be used.

Examples of the base include sodium hydroxide, potassium hydroxide.

Examples of the solvent used include methanol, ethanol, 2-propanol, acetone, tetrahydrofuran, 1,4-dioxane, water, and a mixture thereof.

The intermediates and desired compounds in the above preparations may be isolated and purified by a conventional purification method in organic synthetic chemistry such as neutralization, filtration, extraction, washing, drying, concentration, recrystallization, and each type of chromatography. The intermediates may be also used in the next reaction without any specific purification.

An optically-active product of the present compound can be prepared from an optically-active starting material or intermediate, or by the optical resolution of the racemate of a final product. The optical resolution method includes a physical separation method with optically-active column, and a chemical separation method such as a fractional crystallization method. A diastereomer of the present compound can be prepared by, for example, a fractional crystallization method.

The salt of the compound of formula (1) can be prepared by, for example, mixing the compound of formula (1) with an organic acid or an inorganic acid in a solvent such as water, methanol, ethanol, and acetone.

The induced pluripotent stem cell (iPS cell) of the present invention is a cell induced to have pluripotency by reprogramming a somatic cell by a known method (Cell 126, p 663-676, 2006, Cell 131, p 861-872, 2007, Science 318, p 1917-1920, 2007, Nat Biotechnol 26, p 101-106, 2008). Specifically, cells induced to have pluripotency by reprogramming differentiated somatic cells such as fibroblast cells and peripheral blood mononuclear cells by the expression of a combination of a plurality of genes selected from the group consisting of reprogramming genes such as Oct3/4, Klf4, Klf1, Klf2, Klf5, Sox2, Sox1, Sox3, Sox15, Sox17, Sox18, c-Myc, N-Myc, L-Myc, TERT, SV40 Large T antigen, Glisl, Nanog, Sall4, lin28, and Esrrb can be mentioned. The combination of reprogramming factors may comprise at least one, two, or three reprogramming factors. Preferably, the combination comprises four reprogramming factors. Preferred examples of the combination of reprogramming factors include (1) Oct3/4, Sox2, Klf4, and Myc (c-Myc or L-Myc), and (2) Oct3/4, Sox2, Klf4, Lin28 and L-Myc.

The reprogramming factors can be introduced into cells in a protein form by a method such as lipofection, fusion with a cell-penetrating peptide, and microinjection, and also in a DNA form by a method such as lipofection, a method using liposome, microinjection, and a method using virus vector, plasmid vector, or artificial chromosome vector. Examples of the virus vector include lentivirus vector, retrovirus vector, adenovirus vector, adeno-associated virus vector, and Sendai virus vector. The plasmid vector may use commonly-available plasmid vector for the expression of mammalian cells. The plasmid vector can typically introduce a regulatory sequence such as a promoter, an enhancer, a ribosome binding site, and a terminator to enhance the expression efficiency of reprogramming factors, and can also introduce a factor such as EBNA-1 to increase the plasmid self-renewal efficiency. In addition, the induced pluripotent stem cell can be obtained from somatic cell by a method such as the addition of a compound besides the production method based on direct reprogramming by gene expression (Science 341, p 651-654, 2013, WO 2010/068955).

In addition, established induced pluripotent stem cells are available. For example, iPS cell lines established by Center for iPS Cell Research and Application, Kyoto University (CiRA) are available from Kyoto University and iPS Academia Japan, Inc.

The somatic cells used as starting material in the production of induced pluripotent stem cells may be any cells other than germ cells. Examples thereof include fibroblast cells, epithelial cells, mucosal epithelial cells, exocrine epithelial cells, hormone secretion cells, alveolar cells, neurons, pigment cells, blood-lineage cells (e.g., peripheral blood mononuclear cells (PBMC) and T cells), mesenchymal stem cells, hepatic cells, pancreatic cells, intestinal epithelial cells, smooth muscle cells, and precursor cells thereof. The degree of tissue differentiation and the age of animal for collecting the tissue are not particularly limited. All of the collected tissues can be used as materials of the somatic cells of the present invention.

The induced pluripotent stem cells of the present invention are induced pluripotent stem cells of a mammal (e.g., human, monkey, pig, rabbit, rat, mouse), preferably induced pluripotent stem cells of rodents (e.g., mouse, rat) or primates (e.g., human, monkey), and more preferably human induced pluripotent stem cells (human iPS cells). Also, the induced pluripotent stem cells of the present invention encompass induced pluripotent stem cells genetically modified by a method such as genome editing.

Regenerative medical products are often cell masses, specifically thick multi-layered cell masses formed from many cell layers, or cell aggregates formed by a large number of cells. Thus, when iPS cells to be removed are contained inside a cell mass, compounds with high molecular weight and low permeability inside a cell mass do not act on iPS cells inside the cell mass, and thus the effect for removing iPS cells is considered to be extremely poor. Under these circumstances, it has been strongly desired that methods of removing undifferentiated iPS cells contained in a cell mass using a low-molecular compound with high permeability inside a cell mass are developed.

The stem cell typically means a cell having self-renewal ability and differentiation ability. One of the features in cancer stem cells is the self-renewal ability (Oncogene 2004, 23, 7274). The reliable methods established for measuring the self-renewal ability of cells include a method for measuring the sphere-forming ability of cancer cells in non-adherent condition in the absence of serum (Cancer Res 65, 5506). Also, it is widely known that iPS cells have self-renewal ability. The sphere-forming ability reflects self-renewal ability and is deemed to be one of the important phenotypes of stem cells. As a result, the inhibition of sphere-forming ability is expected to lead to the inhibition of self-renewal ability, and even the proliferation inhibition of cancer stem cells and iPS cells. In addition, the inhibition of iPS cell proliferation is expected to lead to the preparation of useful cells.

The compound of formula (1) or a salt thereof has an inhibitory effect on sphere-forming ability, specifically an inhibitory effect on the sphere-forming ability of cancer stem cells, and inhibits the proliferation of iPS cells and induces cell death. Thus, the compound or a salt thereof can effectively remove iPS cells from an iPS cell-derived cell population. In addition, the present compound is low-molecular compound with high permeability inside a cell mass, and can achieve efficient removal of undifferentiated iPS cells contained inside a cell mass formed from iPS cells, which has been technically difficult until now.

Examples of the cell mass of the present invention include a multi-layered cell mass formed by stacking two or more monolayer cells or forming new cell layer onto monolayer cell, a cell aggregate formed by aggregating cells, a cell population formed by sterically stacking cells with a device such as 3D bioprinter. The cell mass forms culture scaffold by the adhesion of cells to neighboring cells to retain its structure, but may be in the state containing a scaffold material such as hydrogel in the cell mass. Hydrogel is a material capable of containing a large amount of water, and can easily diffuse and transfer materials necessary for survival such as oxygen, water, and nutrients as well as waste materials. As the hydrogel, a biocompatible material is typically used. Examples of the hydrogel include gelatin hydrogel.

The iPS cell-derived cell population of the present invention is a cell population formed by inducing differentiation of iPS cells which is used as an active ingredient of cell medicines including regenerative medical products or an immediate thereof. Examples thereof include plane-cultured cells including colonies, and the above cell mass.

Examples of the cells differentiated and induced from induced pluripotent stem cells include cells for forming a tissue such as hair, eye (retina, cornea), nervous tissue (brain, spinal cord, peripheral nerve), heart, bone (cartilage), lung, kidney, pancreas, intestinal tract, blood vessels, blood, muscle, meniscal, Achilles tendon, liver, fat (breast), skin, and esophagus, and precursor cells thereof, but are not limited thereto.

A method of inducing differentiation of induced pluripotent stem cells into each tissue is not limited as long as the method induces differentiation of the cells. For example, a method such as the method described in WO 2016/063985 can be used in the differentiation-inducing cell aggregates shown in Test Examples, or the cell aggregates containing visual cells for forming retina induced therefrom.

In order to remove undifferentiated cells maintaining pluripotency, specifically iPS cells contained in a cell population formed by inducing differentiation of cells, the method of contacting the cells or the cell population with the present compound can be used as a method of treating the cell population with the present compound. Specifically, the method of adding a liquid (solution or suspension) comprising a compound or a compound itself to a culture solution containing cells or a cell mass is used. The method of adding a concentrated solution of a compound into a culture solution is typically used. The solvent for the concentrated solution is not limited as long as it dissolves the compound. A solvent with relatively high solubility and low toxicity to cells regardless of the physical property of a compound such as dimethyl sulfoxide (DMSO) and ethanol is frequently used as such solvent. The concentration of a compound to be added is 0.001 µmol/L to 10 µmol/L, and preferably 0.01 µmol/L to 1 µmol/L.

The time for contacting the cell population with the present compound is not particularly limited as long as cells are viable. The time is typically 1 hour to 72 hours, and preferably 24 hours to 48 hours.

The temperature for contacting the cell population with the present compound is not particularly limited as long as it is the temperature viable for cells. The temperature is typically 4° C. to 40° C., and preferably 20° C. to 37° C.

The medium used for contacting the cell population with the present compound or a salt thereof is not particularly limited as long as it is a medium or buffer solution which is commonly used for cell culture. Preferably, the medium for inducing differentiation of cells is used.

The present compound was evaluated by the immunostaining of Cleaved Caspase-3, which is a marker of apoptosis, and the quantification of the resulting positive cells. When undifferentiated cells are induced to cell death by the exposure of the present compound, it is thought that the ratio of positive cells of Cleaved Casplase-3 is increased.

EXAMPLES

Hereinafter, the invention is illustrated in more detail with Reference Examples, Examples, and Test Examples, but the invention should not be limited thereto. The compound names as shown in the following Reference Examples and Examples do not necessarily follow the IUPAC nomenclature system.

The following abbreviations may be used herein.
THF: tetrahydrofuran
TFA: trifluoroacetic acid
TBSCl: tert-butyldimethylchlorosilane
DAST: N,N-diethylaminosulfur trifluoride
DMAP: N,N-dimethylaminopyridine
DMF: N,N-dimethylformamide
WSCI.HCl: 1-(3-dimethylaminopropyl)-3-ethylcarbodiimide hydrochloride
HOBt: 1-hydroxybenzotriazole
HATU: O-(7-azabenzotriazol-1-yl)-N,N,N',N'-tetramethyluroni um hexafluorophosphate
Me: methyl
Et: ethyl
Ac: acetyl
TBS: tert-butyldimethylsilyl
Boc: tert-butoxycarbonyl
THP: tetrahydropyranyl LC/MS analysis condition in the compound identification is as follows. The compounds of Reference Examples or Examples were analyzed under LC/MS analysis condition A, B, or C described below.

| Analysis condition A: LC/MS | |
|---|---|
| MS | detector Perkin-Elmer Sciex API 150EX Mass spectrometer (40 eV) |
| HPLC | Shimadzu LC 8A |
| Column | Shiseido CAPCELL PAK C18 Type-MG (5 µm, 4.6 mm × 50 mm), Cat. No.-90105 or Shiseido CAPCELL PAK C18 Type-ACR (5 µm, 4.6 mm × 50 mm), Cat. No.-91105 |
| Detector | UV: 220 nm |
| Solvent | A: 0.035% TFA/CH$_3$CN, B: 0.05% TFA/H$_2$O |
| Flow rate | 3.5 mL/min |
| Gradient condition | 0.0-0.5 min A 10%, 0.5-4.2 min Linear gradient from A 10% to 99%, 4.2-6.3 min A 99% |

| Analysis condition B: LC/MS | |
|---|---|
| Detection device | ACQUITY ® SQ deteceter (Waters) |
| HPLC | ACQUITY UPLC ® system |
| Column | Waters ACQUITY UPLC ® BEH C18 (1.7 µm, 2.1 mm × 30 mm) |
| Solvent | 0.06% formic acid/H$_2$O, B solution: 0.06% formic acid/CH$_3$CN |
| Gradient condition | 0.0-1.3 min Linear gradient from B 2% to 96% |
| Flow rate | 0.8 mL/min |
| Detector | UV: 220 nm and 254 nm |

| Analysis condition C: LC/MS | |
|---|---|
| MS | detector Perkin-Elmer Sciex API 150EX Mass spectrometer (40 eV) |
| HPLC | Agilent 1100 Series |
| Column | YMC CombiScreen ODS-A (S-5 µm, 12 nm) 50 × 4.6 mm |
| Detector | UV: 220 nm |
| Solvent | A: 0.035% TFA/CH$_3$CN, B: 0.05% TFA/H$_2$O, |
| Flow rate | 3.5 mL/min |
| Gradient condition | 0.0-1 min A 10%, 1-4.7 min Linear gradient from A 10% to 99%, 4.7-4.9 min A 99% |

Reference Example 1

1-(3-(Trifluoromethyl)benzyl)-1H-imidazole-4-amine hydrochloride

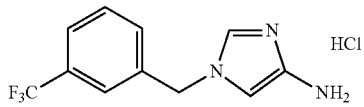

To a solution of 4-nitroimidazole (20 g) in acetonitrile (150 mL) were added potassium carbonate (26.9 g) and potassium iodide (0.074 g), and then a solution of 3-trifluoromethylbenzyl bromide (42.3 g) in acetonitrile (50 mL) was added dropwise thereto at room temperature. The mixture was stirred at 80° C. for 4 hours and cooled to room temperature, and water was added thereto, and then the mixture was extracted with ethyl acetate. The organic layer was dried over anhydrous sodium sulfate, filtrated, and then concentrated in vacuo. To a solution of the resulting crude product (46.1 g) in ethyl acetate (500 mL) was added rhodium-carbon (23.1 g), and the mixture was stirred at room temperature under hydrogen atmosphere. After 20 hours, the reaction mixture was filtrated through Celite®. To the resulting filtrate was added 4 mol/L hydrochloric acid-dioxane (55.3 mL), and the mixture was stirred at room temperature. The resulting precipitate was collected on a filter and washed with ethyl acetate to give the title compound (22.8 g).
LC-MS, condition B ([M+H]+/Rt (min)): 242.1/0.529

Reference Examples 2-6

The compounds of Reference Examples 2-6 were prepared from each corresponding starting compound according to a similar process to that of Reference Example 1.

| Reference Example | Chemical Structural Formula | LC-MS, condition B: [M + H]+/ Rt (min) |
|---|---|---|
| 2 | | 208.1/0.461 |
| 3 | | 258.1/0.564 |
| 4 | | 228.1/0.473 |
| 5 | | 210.1/0.424 |

| Reference Example | Chemical Structural Formula | LC-MS, condition B: [M + H]+/ Rt (min) |
|---|---|---|
| 6 | 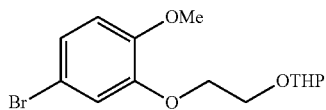 HCl | 210.1/0.422 |

Reference Example 7-1

2-(2-(5-Bromo-2-methoxyphenoxy)ethoxy)tetra-hydro-2H-pyrane

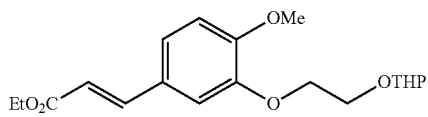

To a solution of 5-bromo-2-methoxyphenol (10.0 g) in DMF (50 mL) were added 2-(2-bromoethoxy)tetrahydro-2H-pyrane (10.8 g) and potassium carbonate (8.86 g), and the mixture was stirred at 80° C. for 2.5 hours. To the reaction mixture was added water, and the mixture was extracted with ethyl acetate. The organic layer was washed with brine, dried over magnesium sulfate, filtrated, and then concentrated in vacuo to give the title compound (15.1 g).

$^1$H-NMR (400 MHz, CDCl$_3$) δ 7.12 (1H, d, J=2.0 Hz), 7.05 (1H, dd, J=8.4, 2.0 Hz), 6.75 (1H, d, J=8.4 Hz), 4.72 (1H, t, J=3.6 Hz), 4.26-4.19 (2H, m), 4.14-4.03 (1H, m), 3.92-3.82 (2H, m), 3.85 (3H, s), 3.57-3.50 (1H, m), 1.90-1.78 (1H, m), 1.78-1.70 (1H, m), 1.68-1.53 (4H, m).

Reference Example 7-2

Ethyl (E)-3-(4-methoxy-3-(2-((tetrahydro-2H-pyran-2-yl)oxy)ethoxy)phenyl)acrylate

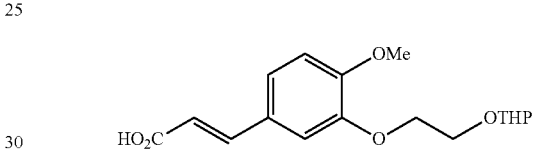

To a solution of the compound of Reference Example 7-1 (14.0 g) in propionitrile (120 mL) were added ethyl acrylate (6.9 mL), N,N-diisopropylethylamine (14.7 mL), palladium acetate (0.48 g), and tris(o-tolyl)phosphine (1.29 g), and the mixture was stirred at 100° C. for 13 hours. To the reaction mixture was added water, and the mixture was extracted with ethyl acetate. The organic layer was washed with brine, dried over magnesium sulfate, filtrated, and then concentrated in vacuo. The residue was purified by silica gel column chromatography (hexane/ethyl acetate) to give the title compound (8.0 g).

$^1$H-NMR (400 MHz, CDCl$_3$) δ 7.62 (1H, d, J=16.0 Hz), 7.19 (1H, d, J=2.0 Hz), 7.12 (1H, dd, J=8.4, 2.0 Hz), 6.87 (1H, d, J=8.4 Hz), 6.31 (1H, d, J=16.0 Hz), 4.73 (1H, t, J=3.6 Hz), 4.31-4.22 (4H, m), 4.15-4.08 (1H, m), 3.93-3.86 (5H, m), 3.57-3.51 (1H, m), 1.88-1.81 (1H, m), 1.78-1.71 (1H, m), 1.68-1.53 (4H, m), 1.35 (3H, t, J=6.8 Hz).

Reference Example 7-3

(E)-3-(4-Methoxy-3-(2-((tetrahydro-2H-pyran-2-yl)oxy)ethoxy)phenyl)acrylic acid

To a solution of the compound of Reference Example 7-2 (3.6 g) in THF/methanol (20 mL/20 mL) was added 2 mol/L aqueous sodium hydroxide solution (15 mL), and the mixture was stirred at 60° C. for 7 hours. To the reaction mixture was added aqueous hydrochloric acid solution to adjust pH to 5.0, and the mixture was extracted with ethyl acetate. The organic layer was washed with brine, dried over magnesium sulfate, filtrated, and then concentrated in vacuo to give the title compound (3.1 g).

$^1$H-NMR (400 MHz, CDCl$_3$) δ 7.72 (1H, d, J=15.6 Hz), 7.23 (1H, d, J=1.6 Hz), 7.15 (1H, dd, J=8.4, 2.0 Hz), 6.89 (1H, d, J=8.4 Hz), 6.33 (1H, d, J=15.6 Hz), 4.74 (1H, t, J=3.6 Hz), 4.33-4.25 (2H, m), 4.15-4.07 (1H, m), 3.95-3.86 (5H, m), 3.58-3.53 (1H, m), 1.88-1.81 (1H, m), 1.79-1.71 (1H, m), 1.69-1.51 (4H, m).

Reference Example 8

The compound of Reference Example 8 was prepared from the corresponding starting compound according to a similar process to that of Reference Example 7.

| Reference Example | Chemical Structural Formula | $^1$H-NMR (400 MHz, CDCl$_3$) |
|---|---|---|
| 8 |  | δ 7.74 (1H, d, J = 15.6 Hz), 7.61 (1H, d, J = 8.0 Hz), 7.24-7.19 (2H, m), 6.53 (1H, d, J = 15.6 Hz), 4.78-4.76 (1H, m), 4.40-4.33 (2H, m), 4.18-4.13 (1H, m), 3.97-3.89 (2H, m), 3.60-3.56 (1H, m), 1.87-1.73 (2H, m), 1.67-1.51 (4H, m). |

Reference Example 9

(E)-N-(1-(3-Chlorobenzyl)-1H-imidazol-4-yl)-3-(4-methoxy-3-(2-((tetrahydro-2H-pyran-2-yl)oxy)ethoxy)phenyl)acrylamide

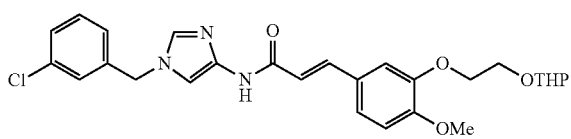

To a solution of the compound of Reference Example 2 (1.20 g) in DMF (30 mL) were added the compound of Reference Example 7-3 (1.90 g), WSCI.HCl (1.13 g), HOBt (0.80 g), and triethylamine (2.2 mL), and the mixture was stirred at room temperature for 2 hours. To the reaction mixture was added water, and the mixture was extracted with chloroform. The organic layer was washed with brine, dried over magnesium sulfate, filtrated, and then concentrated in vacuo. The residue was purified by silica gel column chromatography (chloroform/methanol) to give the title compound (1.25 g). $^1$H-NMR (400 MHz, CDCl$_3$) δ 8.84 (1H, s), 7.64 (1H, d, J=16.0 Hz), 7.48-7.43 (2H, m), 7.35-7.29 (2H, m), 7.23-7.17 (2H, m), 7.14-7.10 (2H, m), 6.87 (1H, d, J=8.0 Hz), 6.43 (1H, d, J=16.0 Hz), 5.10 (2H, s), 4.72-4.69 (1H, m), 4.29-4.24 (2H, m), 4.16-4.07 (1H, m), 3.94-3.85 (5H, m), 3.56-3.51 (1H, m), 1.88-1.80 (1H, m), 1.78-1.71 (1H, m), 1.64-1.52 (4H, m).

Reference Examples 10-12

The compounds of Reference Examples 10-12 were prepared from each corresponding starting compound according to a similar process to that of Reference Example 9.

Reference Example 13

Methyl 6-({1-[3-(trifluoromethyl)benzyl]-1H-imidazol-4-yl}carbamoyl)nicotinate

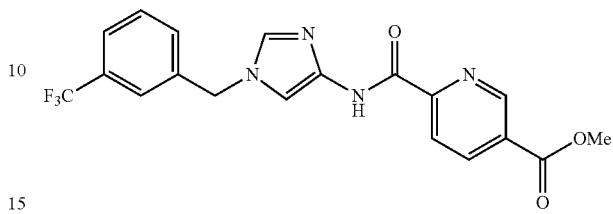

The title compound was prepared from the compound of Reference Example 1 and the corresponding starting compound according to a similar process of that of Reference Example 9.
LC-MS, condition B ([M+H]+/Rt (min)): 404.9/0.901

Reference Example 14-1

Methyl 1-(3,4,5-trifluorobenzyl-1H-imidazole-4-carboxylate

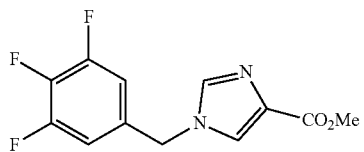

| Reference Example | Chemical Structural Formula | LC-MS, condition B: [M + H]$^+$/Rt (min) |
|---|---|---|
| 10 | 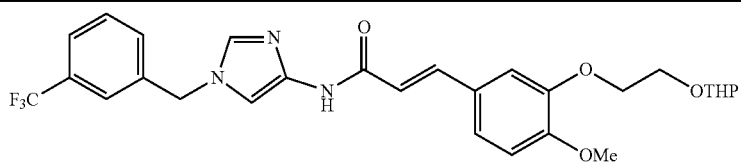 | 546.8/0.968 |
| 11 | 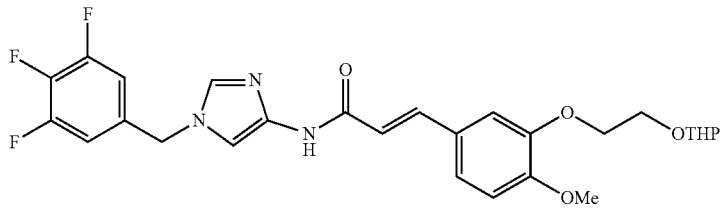 | 532.3/0.964 |
| 12 | 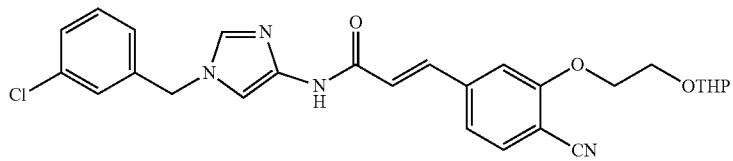 | 507.2/1.010 |

To a solution of methyl 1H-imidazole-4-carboxylate (14.0 g) in acetonitrile (200 mL) were added potassium carbonate (19.9 g) and potassium iodide (0.092 g), and 3,4,5-trifluorobenzyl bromide (14.6 mL) was added dropwise thereto at room temperature, and then the mixture was stirred at 70° C. for 6 hours. The mixture was cooled to room temperature, and to the reaction mixture was added water, and then the mixture was extracted with ethyl acetate. The organic layer was dried over anhydrous magnesium sulfate, filtrated, and then concentrated in vacuo. The resulting crude product was washed with hexane/ethyl acetate (1/2, 60 mL) to give the title compound (14.0 g).

LC-MS, condition B ([M+H]+/Rt (min)): 271.4/0.725

Reference Example 14-2

1-(3,4,5-Trifluorobenzyl)-1H-imidazole-4-carboxylic acid

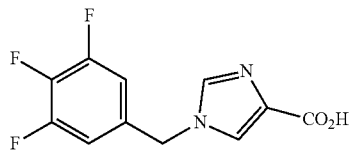 [SMILES: O=C(O)c1cn(Cc2cc(F)c(F)c(F)c2)cn1]

To a solution of the compound of Reference Example 14-1 (4.75 g) in methanol/THF (50 mL/50 mL) was added 2 mol/L aqueous sodium hydroxide solution (13.2 mL), and the mixture was stirred at 50° C. for 5 hours. The reaction mixture was concentrated in vacuo, and the residue was dissolved in water, and then aqueous hydrochloric acid solution was added thereto to adjust pH to 5. The resulting precipitate was collected on a filter, washed with water and hexane, and then dried in vacuo at 50° C. to give the title compound (4.52 g). LC-MS, condition B ([M+H]+/Rt (min)): 257.1/0.513

Reference Example 15

6-({[tert-Butyl(dimethyl)silyl]oxy}methyl)pyridine-3-amine

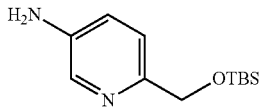 [SMILES: CC(C)(C)[Si](C)(C)OCc1ccc(N)cn1]

To a solution of (5-aminopyridin-2-yl)methanol (135 mg) in THF (15 mL) were added triethylamine (0.30 mL) and TBSCl (328 mg), and the mixture was stirred at room temperature for 6 hours. The solvent was removed in vacuo, and the resulting residue was purified by silica gel column chromatography (chloroform/methanol) to give the title compound (99 mg).

LC-MS, condition B ([M+H]+/Rt (min)): 239.2/0.726

Reference Example 16

2-({[tert-Butyl(dimethyl)silyl]oxy}methyl)quinoline-6-amine

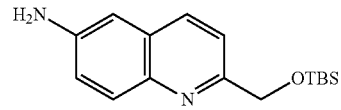

The title compound was prepared from (6-aminoquinolin-2-yl)methanol according to the process of Reference Example 15.

LC-MS, condition B ([M+H]+/Rt (min)): 289.9/0.836

Reference Example 17

According to the process of Reference Example 9, the compound of Reference Example 17 was prepared from the compound of Reference Example 14-2 and the corresponding starting compound.

| Reference Example | Chemical Structural Formula | LC-MS, condition B: [M + H]+/Rt (min) |
|---|---|---|
| 17 | 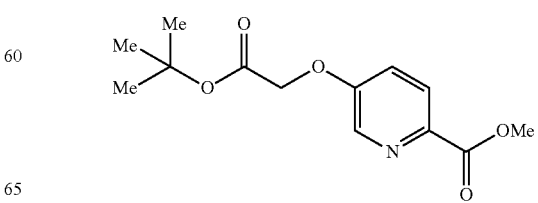 | 411.2/0.915 |

Reference Example 18-1

Methyl 5-(2-tert-butoxy-2-oxoethoxy)-picolinate

To a solution of methyl 5-hydroxy-picolinate (200 mg) in DMF (5 mL) were added potassium carbonate (361 mg) and tert-butyl bromoacetate, and the mixture was stirred at 70° C. for 20 minutes. The mixture was cooled to room temperature, and to the reaction mixture was added water, and then the mixture was extracted with ethyl acetate. The organic layer was washed with brine twice, dried over anhydrous magnesium sulfate, filtrated, and then concentrated in vacuo to give the title compound (320 mg).
LC-MS, condition B ([M+H]$^+$/Rt (min)): 268.2/0.777

Reference Example 18-2

{[6-(Methoxycarbonyl)pyridin-3-yl]oxy}acetic acid

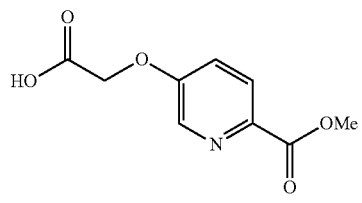 [SMILES: COC(=O)c1ccc(OCC(=O)O)cn1]

To a solution of the compound of Reference Example 18-(320 mg) in dichloromethane (4 mL) was added TFA (2 mL), and the mixture was stirred at room temperature for 2 hours. The solvent was removed to give the title compound (253 mg). LC-MS, condition B ([M+H]$^+$/Rt (min)): 212.0/0.394

Reference Example 18-3

Methyl 5-(2-oxo-2-{[1-(3,4,5-trifluorobenzyl)-1H-imidazol-4-yl]amino}ethoxy)-picolinate

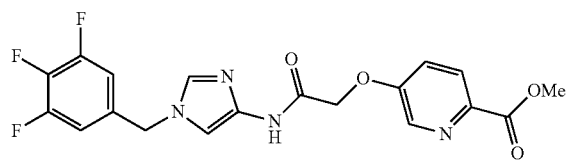 [SMILES: COC(=O)c1ccc(OCC(=O)Nc2cn(Cc3cc(F)c(F)c(F)c3)cn2)cn1]

The title compound was prepared from the compounds of Reference Examples 4 and 18-2 according to the process of Reference Example 9.
LC-MS, condition B ([M+H]$^+$/Rt (min)): 421.2/0.731

Reference Example 19-1

Methyl 6-chloro-5-(dibromomethyl)-nicotinate

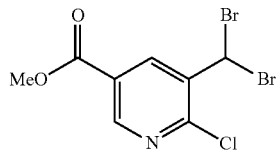 [SMILES: COC(=O)c1cnc(Cl)c(C(Br)Br)c1]

To a suspension of methyl 6-chloro-5-methyl-nicotinate (467 mg) in carbon tetrachloride (25 mL) were added N-bromosuccinimide (1.34 g) and benzoyl peroxide (218 mg), and the mixture was stirred at 100° C. for 7.5 hours. The mixture was cooled to room temperature, and to the reaction mixture were added saturated aqueous sodium thiosulfate solution and water, and the reaction mixture was extracted with chloroform. The organic layer was washed with brine, dried over anhydrous sodium sulfate, filtrated, and then concentrated in vacuo. The residue was purified by silica gel column chromatography (hexane/ethyl acetate) to give the title compound (833 mg). LC-MS, condition B ([M+H]$^+$/Rt (min)): 341.9/1.011

Reference Example 19-2

Methyl 6-chloro-5-formyl-nicotinate

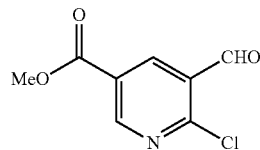 [SMILES: COC(=O)c1cnc(Cl)c(C=O)c1]

To a solution of the compound of Reference Example 19-1 (2.71 g) in acetonitrile (40 mL)/water (20 mL) was added silver nitrate (6.70 g), and the mixture was stirred at 100° C. for 3 hours. The insoluble product was removed by filtration, and the solvent was removed. To the residue was added saturated aqueous sodium hydrogen carbonate solution to adjust pH to 8, and the mixture was extracted with ethyl acetate. The organic layer was washed with brine, dried over anhydrous sodium sulfate, filtrated, and then concentrated in vacuo to give the title compound (0.84 g). LC-MS, condition B ([M+H]$^+$/Rt (min)): 200.0/0.671

Reference Example 19-3

Methyl 6-chloro-5-(difluoromethyl)-nicotinate

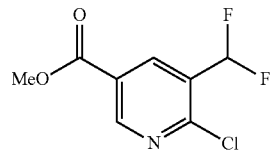 [SMILES: COC(=O)c1cnc(Cl)c(C(F)F)c1]

To a solution of the compound of Reference Example 19-(0.84 g) in dichloromethane (20 mL) was added DAST (1.11 mL) with ice-cooling, and the mixture was stirred with ice-cooling for 30 minutes. To the reaction mixture was added saturated aqueous sodium hydrogen carbonate solution to adjust pH to 8, and the mixture was extracted with chloroform. The organic layer was washed with brine, dried over anhydrous sodium sulfate, filtrated, and then concentrated in vacuo. The residue was purified by silica gel column chromatography (hexane/ethyl acetate) to give the title compound (0.45 g). LC-MS, condition B ([M+H]$^+$/Rt (min)): 222.0/0.828

Reference Example 19-4

Methyl 5-(difluoromethyl)-6-(ethenyl)-nicotinate

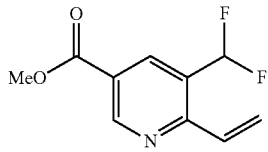

To a solution of the compound of Reference Example 19-3 (450 mg) in a mixture of 1,2-dimethoxyethane (15 mL)/water (1.5 mL) were added vinylboronic acid pinacol ester (0.521 mL), tetrakis(triphenylphosphine)palladium (235 mg), and potassium carbonate (702 mg), and the mixture was stirred at 100° C. for 3.5 hours. The reaction mixture was cooled to room temperature, and water was added thereto, and then the reaction mixture was extracted with chloroform. The organic layer was washed with brine, dried over sodium sulfate, filtrated, and then concentrated in vacuo. The residue was purifed by silica gel column chromatography (hexane/ethyl acetate) to give the title compound (240 mg).
LC-MS, condition B ([M+H]$^+$/Rt (min)): 214.1/0.842

Reference Example 19-5

Methyl 5-(difluoromethyl)-6-(formyl)-nicotinate

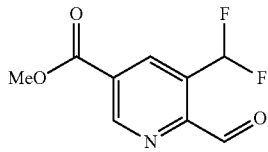 [SMILES: COC(=O)c1cnc(C=O)c(C(F)F)c1]

To a solution of the compound of Reference Example 19-(243 mg) in a mixture of acetone (5 mL)/water (2.5 mL) were added sodium periodate (488 mg) and osmium tetroxide (2.5 wt % in tert-butanol, 0.716 mL), and the mixture was stirred at room temperature for 8 hours. To the reaction mixture was added water, and the reaction mixture was extracted with ethyl acetate. The organic layer was washed with brine, dried over sodium sulfate, filtrated, and then concentrated in vacuo. The residue was purified by silica gel column chromatography (hexane/ethyl acetate) to give the title compound (120 mg).
LC-MS, condition B ([M+H]$^+$/Rt (min)): 216.1/0.736

Reference Example 19-6

Methyl 5-(difluoromethyl)-6-(hydroxymethyl)-nicotinate

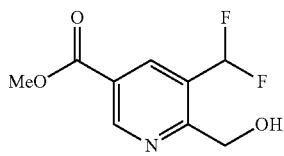 [SMILES: COC(=O)c1cnc(CO)c(C(F)F)c1]

To a solution of the compound of Reference Example 19-(120 mg) in methanol (3 mL) was added sodium borohydride (21 mg), and the mixture was stirred at room temperature for 1 hour. To the reaction mixture were added saturated aqueous ammonium chloride solution and water, and the mixture was extracted with ethyl acetate. The organic layer was washed with brine, dried over sodium sulfate, filtrated, and then concentrated in vacuo to give the title compound (116 mg).
LC-MS, condition B ([M+H]$^+$/Rt (min)): 218.1/0.564

Reference Example 20

Methyl 6-(hydroxymethyl)-5-(trifluoromethyl)-nicotinate

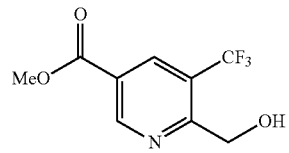

The title compound was prepared from methyl 6-chloro-5-(trifluoromethyl)-nicotinate according to the processes of Reference Examples 19-4, 19-5, and 19-6.
LC-MS, condition B ([M+H]$^+$/Rt (min)): 236.1/0.649

Reference Example 21

Methyl 5-(hydroxymethyl)pyrazine-2-carboxylate

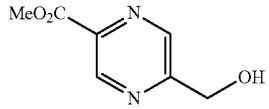

The title compound was prepared from methyl 5-chloropyrazine-2-carboxylate according to the processes of Reference Examples 19-4, 19-5, and 19-6.
LC-MS, condition B ([M+H]$^+$/Rt (min)): 169.0/0.334

Reference Example 22

1-(3,4-Difluorobenzyl)-1H-imidazole-4-carboxylic acid

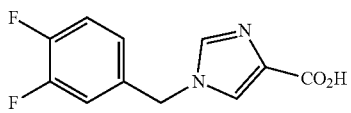 [SMILES: O=C(O)c1cn(Cc2ccc(F)c(F)c2)cn1]

The title compound was prepared from 3,4-difluorobenzyl bromide according to the processes of Reference Examples 14-1 and 14-2.
LC-MS, condition B ([M+H]$^+$/Rt (min)): 239.1/0.460

Reference Example 23 tert-Butyl 6-{[(trifluoromethyl)sulfonyl]oxy}-3,4-dihydro-2,7-naphthyridine-2(1H)-carboxylate

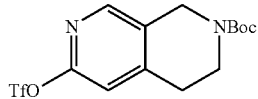

To a solution of tert-butyl 6-hydroxy-1,2,3,4-tetrahydro-2,7-naphthyridine-2-carboxylate (1.73 g) in pyridine (20 mL) was added trifluoromethanesulfonic anhydride (1.28 mL) with ice-cooling, and the mixture was stirred at room temperature for 2 hours. The reaction mixture was concentrated in vacuo, and the residue was purified by silica gel column chromatography (hexane/ethyl acetate) to give the title compound (1.72 g).
LC-MS, condition B ([M+H]$^+$/Rt (min)): 383.2/10.112

Reference Example 24 tert-Butyl 6-bromo-5-fluoro-3,4-dihydroisoquinoline-2(1H)-carboxylate

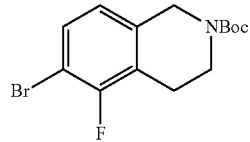 [SMILES: CC(C)(C)OC(=O)N1CCc2c(ccc(Br)c2F)C1]

To acetic acid (15 mL) was added sodium borohydride (340 mg) at room temperature. To the reaction solution was added 6-bromo-5-fluoroisoquinoline (1.0 g), and the mixture was stirred at room temperature 15 hours. To the reaction solution was added sodium borohydride (345 mg), and the mixture was stirred at room temperature for 1 hour. The reaction mixture was concentrated in vacuo, and the residue was dissolved in THF (20 mL). Di-tert-butyl dicarbonate (2.04 g) and triethylamine (3.1 mL) were added thereto, and the mixture was stirred at room temperature for 2 hours. To the reaction mixture was added water, and the mixture was extracted with ethyl acetate. The organic layer was washed with brine, dried over sodium sulfate, filtrated, and then concentrated in vacuo. The residue was purified by silica gel column chromatography (hexane/ethyl acetate) to give the title compound (1.17 g).
LC-MS, condition B ([M+H]$^+$/Rt (min)): 330.2/1.213

Reference Examples 25-26

According to the process of Reference Example 24, the compounds of Reference Examples 25 and 26 were prepared from each corresponding starting compound.

| Reference Example | Chemical Structureal Formula | LC-MS, condition B: [M + H]$^+$/Rt (min) |
|---|---|---|
| 25 | 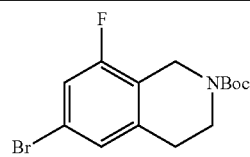 | 330.1/1.244 |
| 26 |  | 330.4/1.217 |

Reference Example 27-1 tert-Butyl 6-cyano-8-fluoro-3,4-dihydroisoquinoline-2(1H)-carboxylate

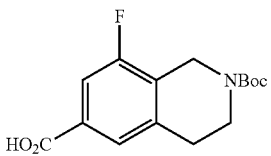 [SMILES: CC(C)(C)OC(=O)N1CCc2cc(C(=O)O)cc(F)c2C1]

To a solution of the compound of Reference Example 25 (124 mg) in DMF (1 mL) was added tetrakis(triphenylphosphine)palladium (45 mg) and zinc cyanide (57 mg), and the mixture was stirred at 120° C. for 8 hours. The reaction mixture was concentrated in vacuo, and the residue was purified by silica gel column chromatography (hexane/ethyl acetate) to give the title compound (48 mg).
LC-MS, condition B ([M+H]$^+$/Rt (min)): 277.2/10.048

Reference Example 27-2

2-(tert-Butoxycarbonyl)-8-fluoro-1,2,3,4-tetrahydroquinoline-6-carboxylic acid

To a solution of the compound of Reference Example 27-1 (2.13 g) in 2-propanol (40 mL) were added water (10 mL) and sodium hydroxide (5 g), and the mixture was stirred at 110° C. for 11 hours. The reaction mixture was concentrated in vacuo, and the residue was extracted with saturated aqueous sodium hydrogen carbonate solution. The aqueous layer was adjusted to acidity with sodium hydrogen sulfate and extracted with chloroform. The resulting organic layer was dried over sodium sulfate and concentrated in vacuo to give the title compound (2.54 g).
LC-MS, condition B ([M+H]$^+$/Rt (min)): 296.2/0.907

Reference Example 28

Methyl 6-(hydroxymethyl)-5-methyl-nicotinate

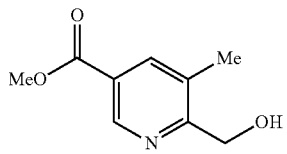 [SMILES: COC(=O)c1cnc(CO)c(C)c1]

The title compound was prepared from methyl 6-chloro-5-methyl-nicotinate according to the processes of Reference Examples 19-4, 19-5, and 19-6.
LC-MS, condition B ([M+H]$^+$/Rt (min)): 182.0/0.354

Reference Example 29-1

Methyl 5-[(tert-butoxycarbonyl)amino]-6-chloro-nicotinate

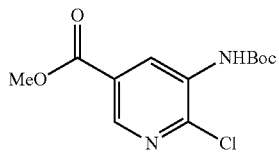

To a solution of methyl 5-amino-6-chloro-nicotinate (325 mg) in THF (10 mL) were added di-tert-butyl dicarbonate (760 mg) and DMAP (11 mg), and the mixture was stirred at room temperature for 15.5 hours. Additional di-tert-butyl dicarbonate (38 mg) was added thereto, and the mixture was stirred at 60° C. for 45 minutes. The mixture was cooled to room temperature, and then the solvent was removed. To the residue were added methanol (5 mL) and potassium carbonate (481 mg), and the mixture was stirred at room temperature for 2.5 hours. Saturated aqueous ammonium chloride solution was added thereto, and the mixture was extracted with ethyl acetate. The organic layer was washed with brine, dried over anhydrous sodium sulfate, filtrated, and then concentrated in vacuo. The residue was purified by silica gel column chromatography (hexane/ethyl acetate) to give the title compound (321 mg).
LC-MS, condition B ([M+H]$^+$/Rt (min)): 287.1/0.985

Reference Example 29-2

Methyl 5-[(tert-butoxycarbonyl)amino]-6-(hydroxymethyl)-nicotinate

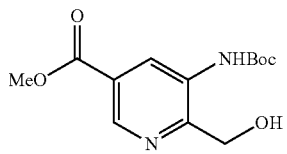 [SMILES: COC(=O)c1cnc(CO)c(NC(=O)OC(C)(C)C)c1]

The title compound was prepared from the compound of Reference Example 29-1 according to the processes of Reference Examples 19-4, 19-5, and 19-6. LC-MS, condition B ([M+H]$^+$/Rt (min)): 282.8/0.761

Reference Example 29-3

2-Oxo-1,4-dihydro-2H-pyrido[3,2-d][1,3]oxazine-7-carboxylic acid

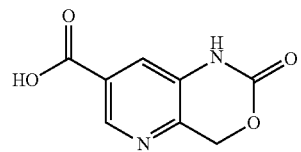 [SMILES: O=C1Nc2cc(C(=O)O)cnc2CO1]

To a solution of the compound of Reference Example 29-(111 mg) in THF (2 mL)/methanol (4 mL) was added 2 mol/L aqueous sodium hydroxide solution (0.39 mL), and the mixture was stirred at room temperature for 16 hours. To the reaction solution was added 2 mol/L hydrochloric acid (0.25 mL) to adjust pH to 7. The reaction mixture was concentrated in vacuo to give the title compound (76 mg).
LC-MS, condition B ([M+H]$^+$/Rt (min)): 195.1/0.325

Reference Examples 30-32

According to the processes of Reference Examples 27-1 and 27-2, the compounds of Reference Examples 30-32 were prepared from the compounds of Reference Examples 23, 24, and 26.

| Reference Example | Chemical Structural Formula | LC-MS: [M + H]$^+$/Rt (min) |
|---|---|---|
| 30 | ![structure] | 296.2/0.867 |
| 31 | ![structure] | 296.1/0.864 |
| 32 | ![structure] | 279.0/0.537 |

Example 1-1

(2E)-3-[4-(Acetylamino)phenyl]-N-(1-[3-(trifluoromethyl)benzyl]-1H-imidazol-4-yl)prop-2-enamide

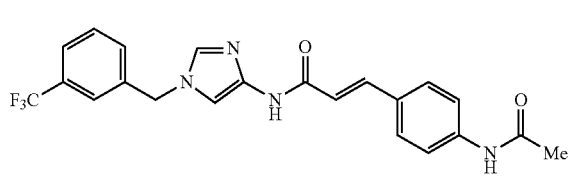 [SMILES: CC(=O)Nc1ccc(/C=C/C(=O)Nc2cn(Cc3cccc(C(F)(F)F)c3)cn2)cc1]

To a solution of the compound of Reference Example 1 (2.0 g) in dimethylformamide (20 mL) were added (E)-3-(4-acetylaminophenyl)acrylic acid (1.41 g), HATU (2.88 g), and diisopropylethylamine (2.97 mL), and the mixture was stirred at room temperature overnight. To the reaction mixture were added saturated aqueous sodium hydrogen carbonate solution and water, and then the resulting precipitate was collected on a filter and washed with water and acetonitrile. The resulting solid was purified by silica gel column chromatography (chloroform/methanol) to give the title compound (0.706 g).

$^1$H-NMR (400 MHz, DMSO-d$_6$) δ 10.51 (1H, s), 10.09 (1H, s), 7.71-7.66 (3H, m), 7.63-7.59 (4H, m), 7.47 (2H, d, J=8.5 Hz), 7.40 (1H, d, J=15.9 Hz), 7.36 (1H, d, J=1.8 Hz), 6.74 (1H, d, J=15.9 Hz), 5.28 (2H, s), 2.05 (3H, s). LC-MS, condition B ([M+H]$^+$/Rt (min)): 429.5/0.88

Example 1-2

(2E)-3-[4-(Acetylamino)phenyl]-N-(1-[3-(trifluoromethyl)benzyl]-1H-imidazol-4-yl)prop-2-enamide hydrochloride To a suspension of the compound of Example 1-1 (500 mg) in ethanol was added 4 mol/L hydrochloric acid-ethyl acetate (350 μL) at 60° C., and the mixture was stirred at this temperature for 5 minutes. An oil bath was removed, a seed crystal was added thereto, and the mixture was stirred at room temperature for 40 minutes and then for 35 minutes with ice-cooling. The resulting precipitate was collected on a filter, washed with iced ethanol, and then dried in vacuo to give the title compound (474 mg).

$^1$H-NMR (400 MHz, DMSO-d$_6$) δ 11.13 (1H, brs), 10.20 (1H, s), 8.62 (1H, brs), 7.85 (1H, s), 7.74-7.62 (5H, m), 7.57-7.49 (4H, m), 6.74 (1H, d, J=15.8 Hz), 5.42 (2H, s), 2.05 (3H, s).

Examples 2-4

The compounds of Examples 2-4 were prepared from each corresponding starting compound according to a similar process to that of Example 1-1.

| Example | Chemical Structural Formula | $^1$H-NMR (400 MHz, DMSO-d$_6$) | LC-MS, condition B: [M + H]$^+$/Rt (min) |
|---|---|---|---|
| 2 | | δ10.51 (1H, s), 10.10 (1H, s), 7.64 (1H, d, J = 1.2 Hz), 7.62 (2H, d, J = 8.5 Hz), 7.47 (2H, d, J = 8.5 Hz), 7.42-7.36 (4H, m), 7.33 (1H, d, J = 1.2 Hz), 7.27-7.24 (1H, m), 6.74 (1H, d, J = 15.8 Hz), 5.18 (2H, s), 2.05 (3H, s). | 395.2/0.80 |
| 3 | | δ10.50 (1H, s), 10.09 (1H, s), 7.64 (1H, brs), 7.61 (2H, d, J = 8.5 Hz), 7.53-7.50 (1H, m), 7.47 (2H, d, J = 8.5 Hz), 7.40 (1H, d, J = 15.9 Hz), 7.35-7.29 (4H, m), 6.74 (1H, d, J = 15.9 Hz), 5.23 (2H, s), 2.05 (3H, s). | 445.2/0.89 |
| 4 | | δ10.51 (1H, s), 10.10 (1H, s), 7.64-7.61 (3H, m), 7.47 (2H, d, J = 8.5 Hz), 7.41 (1H, d, J = 15.9 Hz), 7.37 (1H, d, J = 1.2 Hz), 7.34-7.29 (2H, m), 6.74 (1H, d, J = 15.9 Hz), 5.15 (2H, s), 2.05 (3H, s). | 415.3/0.78 |

Example 5

(E)-3-(3-(2-Hydroxyethoxy)-4-methoxyphenyl)-N-(1-(3,4,5-trifluorobenzyl)-1H-imidazol-4-yl)acrylamide

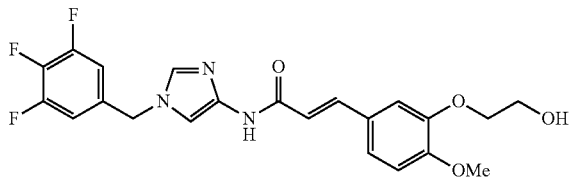 [SMILES: COc1ccc(/C=C/C(=O)Nc2cn(Cc3cc(F)c(F)c(F)c3)cn2)cc1OCCO]

To a solution of the compound of Reference Example 11 (125 mg) in methanol (10 mL) was added 4 mol/L hydrochloric acid-dioxane (88 pt), and the mixture was stirred at 80° C. for 40 minutes. The reaction mixture was concentrated in vacuo, and 2 mol/L aqueous sodium hydroxide solution was added thereto, and then the mixture was extracted with chloroform. The organic layer was washed with brine, dried over magnesium sulfate, filtrated, and then concentrated in vacuo. The residue was purified by silica gel column chromatography (chloroform/methanol) to give the title compound (72 mg).

To a solution of the compound of Reference Example 9 (1.25 g) in methanol (10 mL) was added tosic acid monohydrate (0.46 g), and the mixture was stirred at 40° C. for 2.5 hours. To the reaction mixture were added saturated aqueous sodium hydrogen carbonate solution and chloroform, and the resulting solid was washed with water and dried. The filtrate was extracted with chloroform, washed with brine, and then dried over magnesium sulfate. The reaction mixture was filtrated and concentrated in vacuo, and then the resulting solid was washed with methanol and ethyl acetate and combined with the above solid to give the title compound (0.84 g).

$^1$H-NMR (400 MHz, DMSO-$d_6$) δ 10.40 (1H, s), 7.64 (1H, d, J=1.2 Hz), 7.43-7.36 (4H, m), 7.33 (1H, d, J=1.2 Hz), 7.27-7.24 (1H, m), 7.16-7.10 (2H, m), 7.00 (1H, d, J=8.8 Hz), 6.75 (1H, d, J=16.0 Hz), 5.18 (2H, s), 4.87 (1H, t, J=5.6 Hz), 4.02-3.98 (2H, m), 3.78 (3H, s), 3.75-3.70 (2H, m).

LC-MS, condition B ([M+H]$^+$/Rt (min)): 428.2/0.772

Examples 7-8

The compounds of Examples 7 and 8 were prepared from the compounds of Reference Examples 10 and 12 according to a similar process to that of Example 6.

| Example | Chemical Structural Formula | LC-MS, condition B: [M + H]$^+$/Rt (min) |
|---|---|---|
| 7 | ![structure] | 462.2/0.86 |
| 8 | ![structure] | 423.2/0.815 |

$^1$H-NMR (400 MHz, DMSO-$d_6$) δ 10.39 (1H, s), 7.63 (1H, d, J=1.2 Hz), 7.42-7.30 (4H, m), 7.15-7.11 (2H, m), 6.99 (1H, d, J=8.8 Hz), 6.74 (1H, d, J=16.0 Hz), 5.15 (2H, s), 4.85 (1H, t, J=5.6 Hz), 4.02-3.98 (2H, m), 3.78 (3H, s), 3.74-3.70 (2H, m).

LC-MS, condition B ([M+H]$^+$/Rt (min)): 448.3/0.758

Example 6

(2E)-N-[1-(3-Chlorobenzyl)-1H-imidazol-4-yl]-3-[3-(2-hydroxyethoxy)-4-methoxyphenyl]prop-2-enamide

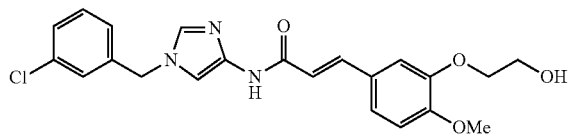 [SMILES: COc1ccc(/C=C/C(=O)Nc2cn(Cc3cccc(Cl)c3)cn2)cc1OCCO]

Example 9

(2E)-N-(1-(3-Chlorobenzyl)-1H-imidazol-4-yl)-3-(pyridin-3-yl)prop-2-enamide

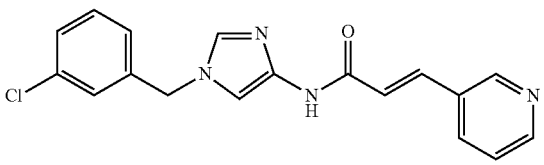 [SMILES: O=C(/C=C/c1cccnc1)Nc1cn(Cc2cccc(Cl)c2)cn1]

The title compound was prepared from the compound of Reference Example 2 and the corresponding starting compound according to a similar process of that of Reference Example 9.

$^1$H-NMR (400 MHz, DMSO-$d_6$) δ 10.7 (1H, s), 8.75 (1H, s), 8.56-8.55 (1H, m), 7.95 (1H, d, J=9.0 Hz), 7.67 (1H, s), 7.55-7.38 (6H, m), 7.27-7.25 (1H, m), 6.96 (1H, d, J=15.0 Hz), 5.19 (2H, s).

Example 10-1

N-[1-(3-Chlorobenzyl)-1H-imidazol-4-yl]-3,4-dimethoxybenzamide

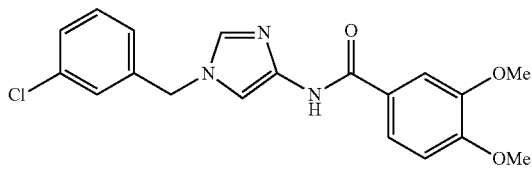 [SMILES: COc1ccc(C(=O)Nc2cn(Cc3cccc(Cl)c3)cn2)cc1OC]

To a solution of the compound of Reference Example 2 (11.0 g) in methylene chloride (240 mL) were added triethylamine (15.8 mL) and 3,4-dimethoxybenzoyl chloride (9.04 g), and the mixture was stirred at room temperature overnight. The reaction solution was concentrated in vacuo, and then the resulting solid was washed with ethyl acetate and collected by a filter to give the title compound (9.7 g). LC-MS, condition C ([M+H]$^+$/Rt (min)): 372.0/2.69

$^1$H-NMR (400 MHz, DMSO-d$_6$) δ 10.64 (1H, s), 7.63 (1H, d, J=1.2 Hz), 7.60-7.56 (2H, m), 7.39-7.31 (4H, m), 7.25-7.21 (1H, m), 6.97 (1H, d, J=8.4 Hz), 5.16 (2H, s), 3.78 (3H, s), 3.76 (3H, s).

Example 10-2

N-[1-(3-Chlorobenzyl)-1H-imidazol-4-yl]-3,4-dimethoxybenzamide hydrochloride

To a solution of the compound of Example 10-1 (70.0 g) in 1,4-dioxane (1.5 L) was added 4 mol/L hydrochloric acid-dioxane (94 mL) and a seed crystal, and the mixture was placed in an ultrasound bath. The solvent was removed, and to the residue was added ethanol (500 mL), and the mixture was again placed in the ultrasound bath. The resulting precipitate was collected on a filter and concentrated in vacuo to give the title compound (72.4 g).

$^1$H-NMR (400 MHz, DMSO-d$_6$) δ 11.53 (1H, s), 8.87 (1H, s), 7.68-7.64 (3H, m), 7.58 (1H, s), 7.46-7.40 (3H, m), 7.09 (1H, d, J=8.8 Hz), 5.40 (2H, s), 3.83 (3H, s), 3.82 (3H, s).

Examples 11-12

The compounds of Examples 11 and 12 were prepared from each corresponding starting compound according to a similar process to that of Example 10-1.

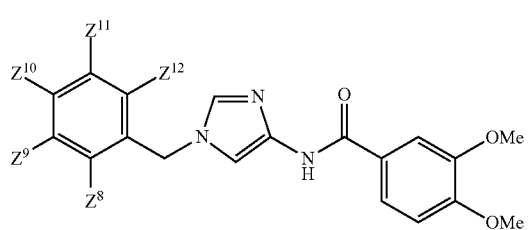

| Example | $Z^8$ | $Z^9$ | $Z^{10}$ | $Z^{11}$ | $Z^{12}$ | LC-MS, condition A: [M + H]$^+$/Rt (min) |
|---|---|---|---|---|---|---|
| 11 | H | F | F | H | H | 374.5/3.47 |
| 12 | H | F | H | F | H | 374.5/3.49 |

Examples 13-14

The compounds of Examples 13 and 14 were prepared from each corresponding starting compound according to a similar process to that of Reference Example 9.

| Example | Chemical Structural Formula | $^1$H-NMR (400 MHz, DMSO-d$_6$) | LC-MS, condition B: [M + H]$^+$/Rt (min) |
|---|---|---|---|
| 13 | ![structure] | δ 10.63 (1H, s), 7.64-7.57 (3H, m), 7.40-7.39 (1H, m), 7.32-7.26 (2H, m) 6.97 (1H, d, J = 8.8 Hz), 5.13 (2H, s), 3.78 (3H, s), 3.76 (3H, s). | 392.3/0.794 |
| 14 | ![structure] | δ 9.63 (1H, s), 7.94-7.91 (1H, m), 7.89-7.87 (1H, m), 7.48-7.46 (1H, m), 7.42-7.32 (3H, m), 6.87-6.82 (1H, m), 5.23 (2H, s), 3.69 (6H, s). | 392.2/0.85 |

Example 15

5-(Hydroxymethyl)-N-{1-[3-(trifluoromethyl)benzyl]-1H-imidazol-4-yl}picolinamide

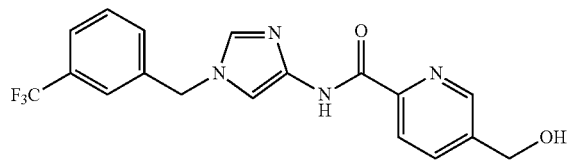 [SMILES: O=C(Nc1cn(Cc2cccc(C(F)(F)F)c2)cn1)c1ccc(CO)cn1]

To a solution of the compound of Reference Example 13 (100 mg) in THF (2 mL)/methanol (1 mL) was added lithium borohydride (3 mol/L in THF, 0.08 mL), and the mixture was stirred at room temperature for 3 hours. To the reaction mixture were added saturated aqueous ammonium chloride solution and water, and the mixture was extracted with ethyl acetate. The organic layer was washed with brine, dried over anhydrous sodium sulfate, filtrated, and then concentrated in vacuo. To the resulting solid were added ethyl acetate (2 mL) and hexane (2 mL), and the mixture was placed in an ultrasound bath. The resulting solid was collected by a filter, washed wish hexane/ethyl acetate (1/1, 1 mL×2), and then dried in vacuo at 40° C. to give the title compound (70 mg).

LC-MS, condition B ([M+H]$^+$/Rt (min)): 377.2/0.733

Examples 16-17

The compounds of Examples 16 and 17 were prepared from the compounds of Reference Examples 17 and 18-3 according to the process of Example 15.

| Example | Chemical Structural Formula | LC-MS, condition B: [M + H]$^+$/Rt (min) |
|---|---|---|
| 16 | | 369.1/0.732 |
| 17 | | 393.2/0.594 |

Examples 18-19

The compounds of Examples 18 and 19 were prepared from the compounds of Reference Examples 1 and 4 and each corresponding starting compound according to the process of Reference Example 9.

| Example | Chemical Structural Formula | LC-MS, condition B: [M + H]$^+$/Rt (min) |
|---|---|---|
| 18 | | 383.2/0.729 |
| 19 | | 369.1/0.690 |

Example 20

6-(Hydroxymethyl)-N-[1-(3,4,5-trifluorobenzyl)-1H-imidazol-4-yl]nicotinamide

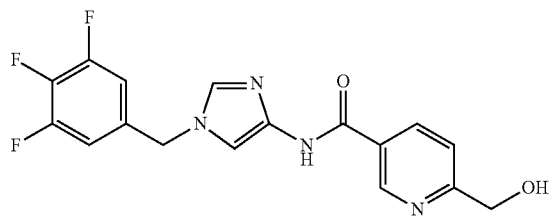 [SMILES: O=C(Nc1cn(Cc2cc(F)c(F)c(F)c2)cn1)c1ccc(CO)nc1]

To a solution of methyl 6-(hydroxymethyl)-nicotinate (0.924 g) in THF (22 mL) was added 5 mol/L aqueous potassium hydroxide solution (2.2 ml). The mixture was stirred at room temperature overnight, concentrated in vacuo to remove the solvent, and then dried in vacuo. To a solution of the resulting solid in DMF (25 mL) were added the compound of Reference Example 4 (1.61 g), HATU (2.52 g), and diisopropylethylamine (2.38 mL), and the mixture was stirred at room temperature for 1 hour. To the reaction mixture were added saturated aqueous sodium hydrogen carbonate solution and water, and the resulting precipitate was collected on a filter. The resulting solid was washed with water and acetonitrile and then ethyl acetate, and then dried in vacuo to give the title compound (1.375 g).

$^1$H-NMR (400 MHz, DMSO-$d_6$) δ 11.00 (1H, s), 9.01 (1H, d, J=1.8 Hz), 8.30 (1H, dd, J=7.9, 1.8 Hz), 7.69 (1H, d, J=1.2 Hz), 7.54 (1H, d, J=7.9 Hz), 7.48 (1H, d, J=1.2 Hz), 7.38-7.30 (2H, m), 5.52 (1H, t, J=6.1 Hz), 5.18 (2H, s), 4.60 (2H, d, J=6.1 Hz).

LC-MS, condition B ([M+H]$^+$/Rt (min)): 363.1/0.66

Examples 21-27

The compounds of Examples 21-27 were prepared from the compounds of each Reference Example according to the process of Example 20.

| Example | Chemical Structural Formula | Instrumental Analysis Data |
|---|---|---|
| 21 | (structure) | LC-MS, condition B: [M + H]$^+$/Rt (min) 343.2/0.611 |
| 22 | (structure) | $^1$H-NMR (400 MHz, DMSO-$d_6$) δ 10.99 (1H, s), 9.01 (1H, d, J = 1.8 Hz), 8.30 (1H, dd, J = 8.5, 1.8 Hz), 7.73-7.72 (2H, m), 7.70-7.68 (1H, m), 7.64-7.59 (2H, m), 7.54 (1H, d, J = 8.5 Hz), 7.47 (1H, d, J = 1.2 Hz), 5.51 (1H, t, J = 6.1 Hz), 5.31 (2H, s), 4.60 (2H, d, J = 6.1 Hz). LC-MS, condition B: [M + H]$^+$/Rt (min) 377.3/0.672 |
| 23 | (structure) | $^1$H-NMR (400 MHz, DMSO-$d_6$) δ 11.27 (1H, s), 9.17 (1H, d, J = 1.8 Hz), 8.54 (1H, d, J = 1.8 Hz), 7.75-7.73 (2H, m), 7.70-7.68 (1H, m), 7.64-7.61 (2H, m), 7.49 (1H, d, J = 1.2 Hz), 7.42 (1H, t, J = 54.3 Hz), 5.61 (1H, t, J = 5.8 Hz), 5.31 (2H, s), 4.75 (2H, d, J = 5.8 Hz). LC-MS, condition B: [M + H]$^+$/Rt (min) 427.2/0.787 |
| 24 | (structure) | $^1$H-NMR (400 MHz, DMSO-$d_6$) δ 11.27 (1H, s), 9.17 (1H, s), 8.54 (1H, s), 7.71 (1H, s), 7.51 (1H, s), 7.42 (1H, t, J = 54.8 Hz), 7.37-7.33 (2H, m), 5.61 (1H, t, J = 5.8 Hz), 5.19 (2H, s), 4.75 (2H, d, J = 5.8 Hz). LC-MS, condition B: [M + H]$^+$/Rt (min) 413.2/0.751 |

| Example | Chemical Structural Formula | Instrumental Analysis Data |
|---|---|---|
| 25 | | LC-MS, condition B: [M + H]⁺/Rt (min) 445.2/0.852 |
| 26 | | LC-MS, condition B: [M + H]⁺/Rt (min) 378.2/0.713 |
| 27 | | $^1$H-NMR (400 MHz, DMSO-$d_6$) δ 10.97 (1H, s), 7.73-7.68 (3H, m), 7.64-7.57 (2H, m), 7.45 (1H, s), 6.81 (1H, s), 5.73 (1H, t, J = 5.8 Hz), 5.30 (2H, s), 4.60 (2H, d, J = 5.8 Hz).<br><br>LC-MS, condition B: [M + H]⁺/Rt (min) 367.2/0.735 |

Example 28

N-[6-(Hydroxymethyl)pyridin-3-yl]-1-(3,4,5-trifluorobenzyl)-1H-imidazole-4-carboxamide

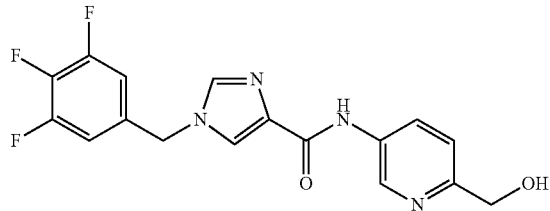 [SMILES: O=C(Nc1ccc(CO)nc1)c1cn(Cc2cc(F)c(F)c(F)c2)cn1]

To a solution of the compound of Reference Example 14-(138 mg) and the compounds of Reference Example 15 (141 mg) in DMF (15 mL) were added WSCI.HCl (124 mg), HOBt (87 mg), and N,N-diisopropylethylamine (0.188 mL), and the mixture was stirred at 80° C. for 6 hours. To the reaction mixture was added water and aqueous sodium hydroxide solution, and the mixture was extracted with chloroform. The organic layer was washed with brine, dried over magnesium sulfate, filtrated, and then concentrated in vacuo. The resulting residue was dissolved in methanol (5 mL), 2 mol/L hydrochloric acid-methanol (0.81 mL) was added thereto, and the mixture was stirred at 40° C. for 5 hours. To the reaction mixture were added water and then aqueous sodium hydroxide solution, and the mixture was extracted with chloroform. The organic layer was washed with brine, dried over magnesium sulfate, filtrated, and then concentrated in vacuo. The residue was purified by silica gel column chromatography (chloroform/methanol) to give the title compound (86.4 mg).

LC-MS, condition B ([M+H]⁺/Rt (min)) 363.2/0.640

$^1$H-NMR (400 MHz, DMSO-$d_6$) δ 10.06 (1H, s), 8.84 (1H, s), 8.19-8.14 (1H, m), 7.97-7.95 (2H, m), 7.42-7.34 (3H, m), 5.31-5.26 (1H, m), 5.24 (2H, s), 4.48 (2H, d, J=4.8 Hz).

Example 29

The compound of Example 29 was prepared from the compound of corresponding Reference Example according to the process of Example 28.

| Example | Chemical Structural Formula | Instrumental Analysis Data |
|---|---|---|
| 29 | | $^1$H-NMR (400 MHz, DMSO-$d_6$) δ 10.13 (1H, s), 8.49 (1H, d, J = 2.0 Hz), 8.24 (1H, d, J = 9.2 Hz), 8.04 (1H, dd, J = 9.2, 2.0 Hz), 8.00 (1H, s), 7.98 (1H, s), 7.85 (1H, d, J = 8.8 Hz), 7.57 (1H, d, J = 8.8 Hz), 7.44-7.38 (2H, m), 5.50-5.46 (1H, m), 5.25 (2H, s), 4.60 (2H, d, J = 5.6 Hz).<br><br>LC-MS, condition B: [M + H]⁺/Rt (min) 413.3/0.673 |

Example 30

N-(7-Fluoro-1,2,3,4-tetrahydroquinolin-6-yl)-1-(3,4,5-trifluorobenzyl)-1H-imidazole-4-carboxamide

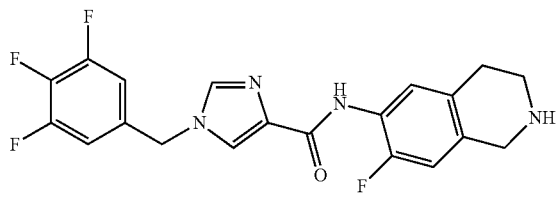 [SMILES: O=C(Nc1cc2c(cc1F)CNCC2)c1cn(Cc2cc(F)c(F)c(F)c2)cn1]

According to the process of Reference Example 9, tert-butyl 7-fluoro-6-({[1-(3,4,5-trifluorobenzyl)-1H-imidazol-4-yl]carbonyl}amino)-3,4-dihydroisoquinoline-2(1H)-carboxylate was prepared from the compound of Reference Example 14-2 and tert-butyl 6-amino-7-fluoro-3,4-dihydroisoquinoline-2(1H)-carboxylate. To a solution of said compound in methanol was added 4 mol/L hydrochloric acid-dioxane, and the mixture was stirred at room temperature overnight. The reaction mixture was concentrated in vacuo, and water and 2 mol/L aqueous sodium hydroxide solution were added thereto. The resulting precipitate was collected on a filter, washed with water and hexane/ethyl acetate (2/1), and dried in vacuo to give the title compound. LC-MS, condition B ([M+H]$^+$/Rt (min)): 405.2/0.665

$^1$H-NMR (400 MHz, DMSO-$d_6$) δ 9.27 (1H, s), 7.96-7.93 (2H, m), 7.69 (1H, d, J=8.0 Hz), 7.43-7.34 (2H, m), 6.91 (1H, d, J=11.6 Hz), 5.23 (2H, s), 3.75 (2H, s), 2.90-2.86 (2H, m), 2.62-2.57 (2H, m).

Examples 31-32

The compounds of Examples 31 and 32 were prepared from the compounds of Reference Examples 14-2 and 22 and each corresponding compound according to the process of Example 30.

Example 33

N-(1,2,3,4-Tetrahydroquinolin-6-yl)-1-(3,4,5-trifluorobenzyl)-1H-imidazole-4-carboxamide dihydrochloride

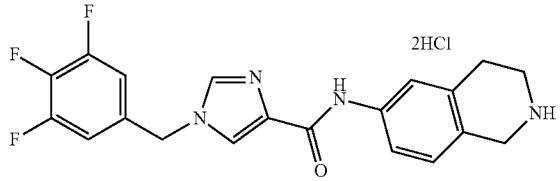 [SMILES: O=C(Nc1ccc2c(c1)CCNC2)c1cn(Cc2cc(F)c(F)c(F)c2)cn1]

According to the process of Reference Example 9, tert-butyl 6-({[1-(3,4,5-trifluorobenzyl)-1H-imidazol-4-yl]carbonyl}amino)-3,4-dihydroisoquinoline-2(1H)-carboxylate was prepared from the compound of Reference Example 14-2 and tert-butyl 6-amino-3,4-dihydroisoquinoline-2(1H)-carboxylate. To a solution of said compound in methanol was added 4 mol/L hydrochloric acid-dioxane, and the mixture was stirred at 80° C. The resulting precipitate was collected on a filter, washed with diisopropyl ether, and then dried in vacuo to give the title compound.

LC-MS, condition B ([M+H]$^+$/Rt (min)): 387.2/0.615

Examples 34-49

The compounds of Examples 34-49 were prepared from the compound of each Reference Example and each corresponding starting compound according to the process of Example 33.

| Example | Chemical Structure Formula | Instrumental Analysis Data |
|---|---|---|
| 31 | 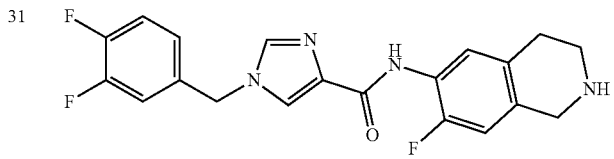 | $^1$H-NMR (400 MHz, DMSO-$d_6$) δ 9.28 (1H, s), 7.96-7.93 (2H, m), 7.71 (1H, d, J = 7.6 Hz), 7.53-7.42 (2H, m), 7.22-7.18 (1H, m), 6.93 (1H, d, J = 10.8 Hz), 5.24 (2H, s), 3.78 (2H, s), 2.93-2.89 (2H, m), 2.65-2.59 (2H, m). LC-MS, condition B: [M + H]$^+$/Rt (min) 387.0/0.660 |
| 32 | 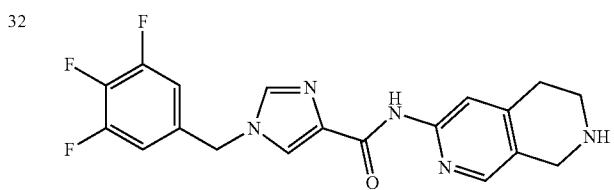 | $^1$H-NMR (400 MHz, DMSO-$d_6$) δ 9.30 (1H, s), 8.02 (1H, s), 7.97 (1H, s), 7.96 (1H, s), 7.88 (1H, s), 7.43-7.37 (2H, m), 5.23 (2H, s), 3.78 (2H, s), 2.92-2.88 (2H, m), 2.71-2.66 (2H, m). LC-MS, condition B: [M + H]$^+$/Rt (min) 388.2/0.601 |

| Example | Chemical Structural Formula | Instrumental Analysis Data |
|---|---|---|
| 34 | | ¹H-NMR (400 MHz, CD₃OD) δ 8.94 (1H, d, J = 1.6 Hz), 7.78 (1H, s), 7.65 (1H, d, J = 9.2 Hz), 7.58 (1H, d, J = 2.0 Hz), 7.33-7.30 (2H, m), 5.44 (2H, s), 4.46 (2H, s), 3.56 (2H, t, J = 6.4 Hz), 3.24 (2H, t, J = 6.0 Hz). LC-MS, condition B: [M + H]⁺/Rt (min) 405.2/0.645 |
| 35 | | ¹H-NMR (400 MHz, CD₃OD) δ 8.89 (1H, d, J = 2.0 Hz), 7.87 (2H, m), 7.55 (1H, d, J = 2.0 Hz), 7.42 (1H, d, J = 8.4 Hz), 7.33-7.27 (2H, m), 5.43 (2H, s), 4.46 (2H, s), 3.56 (2H, t, J = 6.4 Hz), 3.22 (2H, t, J = 6.4 Hz). LC-MS, condition B: [M + H]⁺/Rt (min) 387.2/0.635 |
| 36 | | ¹H-NMR (400 MHz, CD₃OD) δ 7.77 (1H, d, J = 6.8 Hz), 7.58 (1H, s), 7.27-7.22 (4H, m), 5.37 (2H, s), 4.44 (2H, s), 3.54 (2H, t, J = 6.4 Hz), 3.16 (2H, t, J = 6.4 Hz). LC-MS, condition B: [M + 2H]²⁺/Rt (min) 203.1/0.620 |
| 37 | | ¹H-NMR (400 MHz, CD₃OD) δ 8.90 (1H, d, J = 1.6 Hz), 8.61 (1H, s), 8.17 (1H, s), 7.65 (1H, d, J = 1.6 Hz), 7.35-7.28 (2H, m), 5.43 (2H, s), 4.54 (2H, s), 3.58 (2H, t, J = 6.4 Hz), 3.26 (2H, t, J = 6.4 Hz). LC-MS, condition B: [M + H]⁺/Rt (min) 388.2/0.554 |
| 38 | | ¹H-NMR (400 MHz, CD₃OD) δ 8.94 (1H, s), 8.60 (1H, s), 8.12 (1H, s), 7.82 (1H, s), 7.76-7.65 (4H, m), 5.55 (2H, s), 4.53 (2H, s), 3.58 (2H, t, J = 5.2 Hz), 3.26 (2H, t, J = 6.4 Hz) LC-MS, condition B: [M + 2H]²⁺/Rt (min) 201.7/0.659 |
| 39 | | ¹H-NMR (400 MHz, CD₃OD) δ 8.84 (1H, s), 8.12 (1H, d, J = 8.4 Hz), 7.91 (1H, d, J = 8.4 Hz), 7.81 (1H, s), 7.75-7.64 (4H, m), 5.54 (2H, s), 4.53 (2H, s), 3.69 (2H, t, J = 6.4 Hz), 3.36 (2H, t, J = 6.4 Hz). LC-MS, condition B: [M + 2H]²⁺/Rt (min) 201.7/0.620 |
| 40 | | ¹H-NMR (400 MHz, CD₃OD) δ 8.80 (1H, d, J = 1.6 Hz), 8.13 (1H, d, J = 8.0 Hz), 7.92 (1H, d, J = 8.4 Hz), 7.67 (1H, d, J = 2.0 Hz), 7.33-7.26 (2H, m), 5.42 (2H, s), 4.54 (2H, s), 3.70 (2H, t, J = 6.4 Hz), 3.37 (2H, t, J = 6.4 H). |

-continued

| Example | Chemical Structural Formula | Instrumental Analysis Data |
|---|---|---|
| | | LC-MS, condition B: [M + 2H]²⁺/Rt (min) 194.7/0.636 |
| 41 | 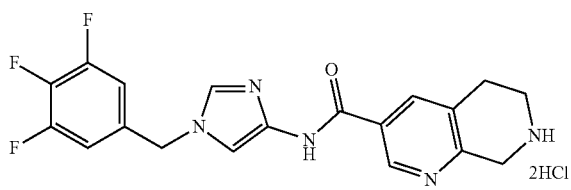 [SMILES: O=C(Nc1cn(Cc2cc(F)c(F)c(F)c2)cn1)c1cnc2c(c1)CCNC2] | ¹H-NMR (400 MHz, CD₃OD) δ 9.03 (1H, s), 9.00 (1H, s), 8.31 (1H, s), 7.61 (1H, s), 7.32 (2H, t, J = 7.2 Hz), 5.44 (2H, s), 4.50 (2H, s), 3.61 (2H, t, J = 6.4 Hz), 3.26 (2H, t, J = 6.4 Hz). LC-MS, condition B: [M + 2H]²⁺/Rt (min) 194.7/0.624 |
| 42 | 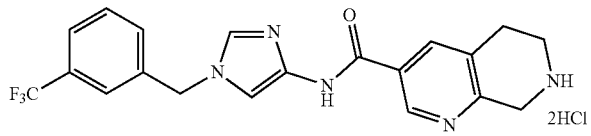 [SMILES: O=C(Nc1cn(Cc2cccc(C(F)(F)F)c2)cn1)c1cnc2c(c1)CCNC2] | ¹H-NMR (400 MHz, CD₃OD) δ 9.00 (1H, d, J = 2.4 Hz), 8.76 (1H, s), 8.26 (1H, d, J = 1.6 Hz), 7.78-7.57 (4H, m), 7.56 (1H, d, J = 0.8 Hz), 5.51 (2H, s), 4.48 (2H, s), 3.60 (2H, t, J = 6.4 Hz), 3.24 (2H, t, J = 6.4 Hz). LC-MS, condition B: [M + H]⁺/Rt (min) 402.3/0.590 |
| 43 | 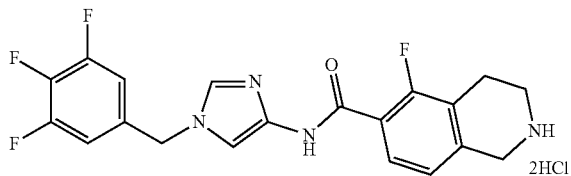 | ¹H-NMR (400 MHz, CD₃OD) δ 8.72 (1H, s), 7.77 (1H, t, J = 7.6 Hz), 7.59 (1H, d, J = 1.2 Hz), 7.29-7.24 (3H, m), 5.39 (2H, s), 4.47 (2H, s), 3.58 (2H, t, J = 6.4 Hz), 3.15 (2H, t, J = 6.4 Hz). LC-MS, condition B: [M + 2H]²⁺/Rt (min) 203.1/0.650 |
| 44 | 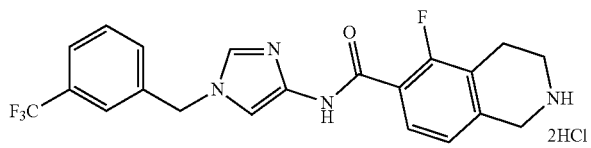 [SMILES: O=C(Nc1cn(Cc2cccc(C(F)(F)F)c2)cn1)c1ccc2c(c1F)CCNC2] | ¹H-NMR (400 MHz, CD₃OD) δ 8.83 (1H, s), 7.80-7.61 (5H, m), 7.59 (1H, d, J = 1.2 Hz), 7.24 (1H, d, J = 7.6 hz), 5.52 (2H, s), 4.47 (2H, s), 3.58 (2H, t, J = 6.4 Hz), 3.15 (2H, t, J = 6.4 Hz). LC-MS, condition B: [M + 2H]²⁺/Rt (min) 210.1/0.708 |
| 45 | 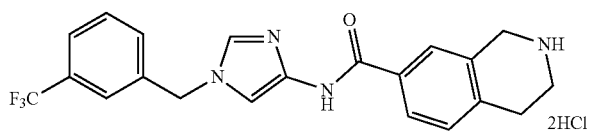 [SMILES: O=C(Nc1cn(Cc2cccc(C(F)(F)F)c2)cn1)c1ccc2c(c1)CNCC2] | LC-MS, condition B: [M + H]⁺/Rt (min) 401.3/0.588 |
| 46 | 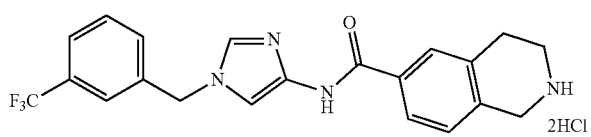 [SMILES: O=C(Nc1cn(Cc2cccc(C(F)(F)F)c2)cn1)c1ccc2c(c1)CCNC2] | LC-MS, condition B: [M + 2H]²⁺/Rt (min) 201.2/0.663 |
| 47 | 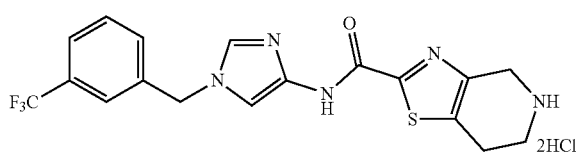 [SMILES: O=C(Nc1cn(Cc2cccc(C(F)(F)F)c2)cn1)c1nc2c(s1)CCNC2] | LC-MS, condition B: [M + H]⁺/Rt (min) 408.2/0.603 |

| Example | Chemical Structural Formula | Instrumental Analysis Data |
|---|---|---|
| 48 | (3-CF3-benzyl)-imidazole(Me)-C(O)NH-tetrahydroisoquinoline · 2HCl | $^1$H-NMR (400 MHz, CD$_3$OD) δ 8.93 (1H, s), 7.91-7.88 (2H, m), 7.78-7.60 (4H, n), 7.42 (1H, d, J = 8.0 Hz), 5.57 (2H, s), 4.47 (2H, s), 3.56 (2H, t, J = 6.4 Hz), 3.22 (2H, t, J = 6.4 Hz), 2.21 (3H, d, J = 1.2 Hz). LC-MS, condition B: [M + 2H]$^{2+}$/Rt (min) 208.2/0.668 |
| 49 | (3-CF3-benzyl)-2-Me-imidazole-C(O)NH-tetrahydroisoquinoline · 2HCl | $^1$H-NMR (400 MHz, CD$_3$OD): δ 7.88-7.85 (2H, m), 7.75-7.73 (2H, m), 7.68-7.60 (2H, m), 7.42-7.38 (2H, m), 5.49 (2H, s), 4.46 (2H, s), 3.55 (2H, t, J = 6.4 Hz), 3.21 (2H, t, J = 6.0 Hz), 2.68 (3H, d, J = 2.4 Hz). LC-MS, condition B: [M + 2H]$^{2+}$/Rt (min) 208.2/0.583 |

Example 50

N-[1-(3,4,5-Trifluorobenzyl)-1H-imidazol-4-yl]-(1,2,3,4-tetrahydroquinoline-6-carboxamide ditrifluoroacetate

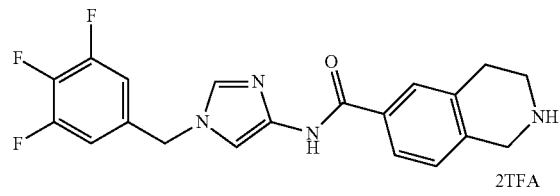 [SMILES: O=C(Nc1cn(Cc2cc(F)c(F)c(F)c2)cn1)c1ccc2c(c1)CCNC2]

According to the process of Reference Example 9, N-(1-(3,4,5-trifluorobenzyl)-1H-imidazol-4-yl)-1,2,3,4-tetrahydroquinoline-6-carboxamide was prepared from the compound of Reference Example 4 and 2-(tert-butoxycarbonyl)-1,2,3,4-tetrahydroquinoline-6-carboxylate. To a solution of said compound in chloroform was added trifluoroacetic acid, the mixture was stirred at room temperature, and then the reaction mixture was concentrated in vacuo. To the residue was added a mixture of hexane and ethyl acetate, and the resulting precipitate was collected on a filter and dried in vacuo to give the title compound.

LC-MS, condition B ([M+2H]$^{2+}$/Rt (min)): 194.1/0.580

$^1$H-NMR (400 MHz, CDCl$_3$) δ 7.94 (1H, d, J=1.6 Hz), 7.85-7.83 (2H, m), 7.47 (1H, d, J=2.0 Hz), 7.38 (1H, d, J=8.4 Hz), 7.14 (2H, dd, J=8.4, 6.8 Hz), 5.26 (2H, s), 4.44 (2H, s), 3.55 (2H, t, J=6.4 Hz), 3.20 (2H, t, J=6.4 Hz).

Examples 51-54

The compounds of Examples 51-54 were prepared from the compound of corresponding Reference Example and each corresponding starting compound according to the process of Example 50.

| Example | Chemical Structural Formula | LC-MS, condition B: [M + H]$^+$/Rt (min) |
|---|---|---|
| 51 | (3-CF3-benzyl)-imidazole-C(O)NH-tetrahydroisoquinoline · 2TFA | 401.3/0.588 |
| 52 | (3-CF3-benzyl)-imidazole-C(O)NH-tetrahydroquinoline · 2TFA | 401.3/0.899 |

| Example | Chemical Structural Formula | LC-MS, condition B: [M + H]⁺/Rt (min) |
|---|---|---|
| 53 | | 194.58 ([M + 2H]²⁺)/0.601 |
| 54 | | 429.3/0.706 |

Example 55

6-(Hydroxymethyl)-5-methyl-N-[1-(3,4,5-trifluorobenzyl)-1H-imidazol-4-yl]nicotinamide

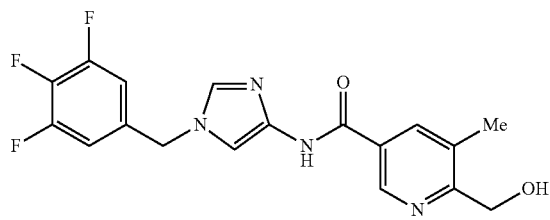 [SMILES: Cc1cc(C(=O)Nc2cn(Cc3cc(F)c(F)c(F)c3)cn2)cnc1CO]

The title compound was prepared from the compound of Reference Example 28 according to the process of Example 20.

LC-MS, condition B ([M+H]⁺/Rt (min)): 377.2/0.631

$^1$H-NMR (400 MHz, DMSO-d$_6$) δ 10.97 (1H, s), 8.87 (1H, d, J=1.8 Hz), 8.10 (1H, d, J=1.8 Hz), 7.69 (1H, d, J=1.2 Hz), 7.48 (1H, d, J=1.2 Hz), 7.38-7.31 (2H, m), 5.18 (2H, s), 5.11 (1H, t, J=5.5 Hz), 4.60 (2H, d, J=5.5 Hz), 2.35 (3H, s).

Examples 56-57

The compounds of Examples 56 and 57 were prepared from the compounds of Reference Examples 1, 4, and 29-3 according to the process of Reference Example 9.

| Example | Chemical Structural Formula | LC-MS, condition B: [M + H]⁺/Rt (min) |
|---|---|---|
| 56 | | 418.2/0.711 |
| 57 | | 404.2/0.670 |

Example 58

5-Amino-6-(hydroxymethyl)-N-{1-[3-(trifluoromethyl)benzyl]-1H-imidazol-4-yl}nicotinamide

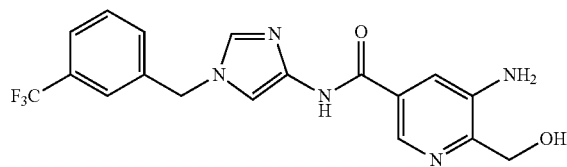 [SMILES: Nc1cc(C(=O)Nc2cn(Cc3cccc(C(F)(F)F)c3)cn2)cnc1CO]

To a suspension of the compound of Example 56 (13 mg) in THF (0.5 mL)/methanol (0.5 mL) was added 2 mol/L aqueous sodium hydroxide solution (0.031 mL), and the mixture was stirred at 60° C. for 3 hours and then at 90° C. for 6.5 hours. The reaction mixture was cooled to room temperature, and water was added thereto, and then the mixture was stirred at room temperature for 5 minutes. The resulting precipitate was collected on a filter, washed with water, and then dried in vacuo at 50° C. to give the title compound (7 mg).
LC-MS, condition B ([M+H]$^+$/Rt (min)): 392.2/0.647
$^1$H-NMR (400 MHz, DMSO-d$_6$) δ 10.79 (1H, s), 8.29 (1H, d, J=1.8 Hz), 7.72-7.68 (3H, m), 7.64-7.581 (2H, m), 7.43 (1H, d, J=1.2 Hz), 7.42 (1H, d, J=1.8 Hz), 5.36 (2H, s), 5.30 (2H, s), 5.18 (1H, t, J=5.5 Hz), 4.52 (2H, d, J=5.5 Hz)

Example 59

The compound of Example 59 was prepared from the compound of Example 57 according to the process of Example 58.

oxalyl chloride (39 μL) and DMF (2 μL), and the mixture was stirred at room temperature for 1 hour. The reaction mixture was concentrated in vacuo and dried to give acid chloride. To a solution of the compound of Reference Example 1 (70.0 mg) in dichloromethane (5 mL) triethylamine (105 μL), and the acid chloride was added dropwise thereto. The mixture was stirred overnight, and water was added thereto, and then the mixture was extracted with chloroform. The organic layer was washed with brine, dried over magnesium sulfate, filtrated, and then concentrated in vacuo. The residue was purified by silica gel column chromatography (chloroform/methanol) to give the title compound (30 mg).
LC-MS, condition B ([M+H]$^+$/Rt (min)): 460.2/10.01

Test Example 1: Test for Inhibiting Sphere-Forming Ability of Cancer Cells

The reliable methods established for measuring the self-renewal ability of cells which is one of the CSC's properties include a method for measuring the sphere-forming ability of cancer cells in non-adherent condition in the absence of serum (Cancer Res 65, 5506-5511 (2005)). HCT-116 cells were available from the American Type Culture Collection (ATCC). HCT-116 cells were cultured at 37° C. and 5% CO$_2$ using the McCoy's 5a medium containing 10% fetal bovine serum (FBS), 100 U/ml penicillin, and 100 μg/ml streptomycin. HCT-116 cells were seeded in a 384 Well Black Clear Bottom Ultra-Low Attachment Microplate (Corning Cat. No. 3827) in an amount of 350-800 cells/well using the

| Example | Chemical Structural Formula | LC-MS, condition B: [M + H]$^+$/Rt (min) |
|---|---|---|
| 59 | 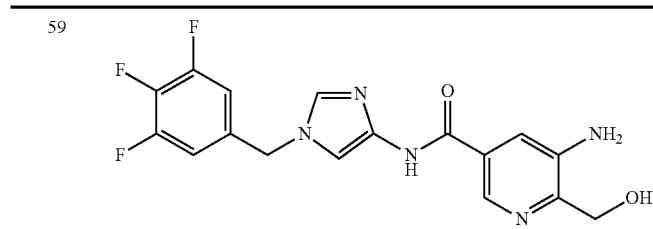 | 378.2/0.603 |

Example 60

(E)-2-Methoxy-5-(3-oxo-3-((1-(3-(trifluoromethyl)benzyl)-1H-imidazol-4-yl)amino)prop-1-en-1-yl)phenolacetate

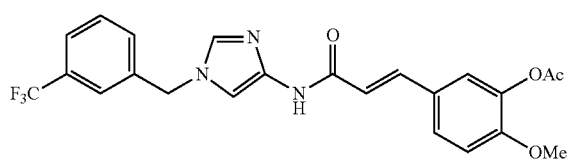 [SMILES: COc1ccc(/C=C/C(=O)Nc2cn(Cc3cccc(C(F)(F)F)c3)cn2)cc1OC(C)=O]

To a solution of (E)-3-(3-acetoxy-4-methoxyphenyl)acrylic acid (71.0 mg) in dichloroethane (2 mL) were added DMEM/F12 medium containing 2% B27 supplement (GIBCO), 20 ng/mL epidermal growth factor (EGF) (peprotech), 10 ng/mL basic fibroblast growth factor (bFGF) (peprotech), 5 μg/mL insulin (Sigma), and 1% penicillin/streptomycin. The test compounds were added into each well to adjust the final concentration of DMSO to 0.1%, and the cells were cultured for 4 days. The number of viable cells in each well was then measured with CeilTiter-Glo® Luminescent Cell Viability Assay (Promega) to calculate the concentration of each test compound for 50% inhibition of cell proliferation (Sphere IC$_{50}$ value; μmol/L).

The experiment of Test Example 1 was performed for the compound of each Example. The concentration of each test compound for 50% inhibition of cell proliferation (Sphere IC$_{50}$ value; μmol/L) is shown in the following Table. The % value shows (100%−inhibition ratio of cell proliferation) in 1 μmol/L.

| Example | IC$_{50}$ (μmol/L) |
|---|---|
| 1-2 | 0.31 |
| 2 | 0.22 |
| 3 | 0.63 |
| 4 | <0.01 |
| 5 | 0.06 |
| 6 | 0.06 |
| 7 | 0.09 |
| 8 | 0.08 |
| 9 | 0.89 |
| 10-2 | 0.63 |
| 11 | 0.35 |
| 12 | 0.09 |
| 13 | 0.06 |
| 14 | 0.21 |
| 15 | 0.030 |
| 16 | 0.629 |
| 17 | <0.01 |
| 18 | 0.024 |
| 19 | 0.077 |
| 20 | 0.007 |
| 21 | 0.056 |
| 22 | <0.01 |
| 23 | <0.01 |
| 24 | <0.01 |
| 25 | 0.070 |
| 26 | 0.053 |
| 27 | 0.653 |
| 28 | <0.01 |
| 29 | 0.079 |
| 30 | 0.08 |
| 31 | 0.66 |
| 32 | 0.06 |
| 33 | 0.66 |
| 34 | 0.07 |
| 35 | 0.06 |
| 36 | 0.39 |
| 37 | 0.09 |
| 38 | 0.07 |
| 39 | 0.04 |
| 40 | 0.05 |
| 41 | 0.07 |
| 42 | 0.03 |
| 43 | 0.43 |
| 44 | 0.36 |
| 45 | 0.67 |
| 47 | 65.15 |
| 48 | 6.20 |
| 49 | 0.20 |
| 50 | 0.06 |
| 51 | 0.08 |
| 52 | 0.69 |
| 55 | <0.01 |
| 56 | 0.52 |
| 58 | 0.029 |
| 59 | 0.01 |

Test Example 2: Evaluation of Cytotoxic Activity of the Present Compound Against iPS Cells Human iPS cells were cultured under feeder-free condition according to the method described in Scientific Reports, 4, 3594 (2014). The StemFit medium (AKO3N, Ajinomoto) was used as feeder-free medium, and Laminin511-E8 (Nippi) was used as feeder-free scaffold.

The subconfluent human iPS cells were washed with PBS and dispersed into single cells using TrypLE Select (Life Technologies). The human iPS cells were then seeded in a plastic culture dish coated with Laminin511-E8, and cultured under feeder-free conditions at 37° C. and 5% $CO_2$ using the StemFit medium in the presence of Y27632 (ROCK inhibitory compound, 10 μmol/L). A 96-well plate (BD, for cell culture, culture area 0.35 cm$^2$) was used as the plastic culture dish, and the number of plated cells for the human iPS cells dispersed into single cells was set to 0.03×10$^4$. The medium was changed to Y27632-free StemFit medium 1 day after the seeding. Thereafter, the medium was changed to the Y27632-free StemFit medium once in 1 to 2 days. The cells were then cultured until subconfluent (60% of culture area is covered with the cells). To the human iPS cells was added the Stem Fit medium (AK03; Ajinomoto) to adjust the final concentrations of the compounds of Examples 1-2, 10-2, and 22 dissolved in DMSO to 10, 1, 0.1, and 0.01 μmol/L, and the cells were cultured for 24 hours.

Also, in this test example, human cervical cancer-derived cells, HeLa cells which are differentiated cells were used as negative control. The HeLa cells were cultured at 37° C. and 5% $CO_2$ for 24 hours using the DMEM medium (Life Technologies) containing inactivated 10% fetal bovine serum (MP Biomedicals), and cultured for 24 hours the medium containing the compounds of Examples 1-2, 10-2, and 22 in a similar method to that of the above culture of human iPS cells.

After 24 hours, the medium was removed, the obtained cells were each fixed with 4% paraformaldehyde at 4° C. for 15 minutes, PBS solution containing DAPI (Sigma) was added thereto to perform nuclear staining for the cells, and then the cells were observed by inverted fluorescence microscope (Keyence, BIREVO). In addition, the DAPI positive area was calculated using the quantitative software of the microscope.

As a result, it was found that the compound of Example 1-2 had cytotoxic activity against human iPS cells in a concentration of 0.1 μmol/L or more. Also, the ratio of viable cells treated with the compound of Example 1-2 was 53% in a concentration of 0.1 μmol/L, 25% in a concentration of 1 μmol/L, and 14% in a concentration of 10 μmol/L to that of cells without treatment with the compound (FIGS. 1 and 4). In addition, the ratio of viable cells treated with the compound of Example 10-2 was 37% in a concentration of 1 μmol/L, and 17% in a concentration of 10 μmol/L (FIGS. 2 and 4). Also, the ratio of viable cells treated with the compound of Example 22 was 51% in a concentration of 0.1 μmol/L, and 31% in a concentration of 1 μmol/L (FIGS. 3 and 4)

Test Example 3: Evaluation of Effect of the Present Compound on Differentiation-Inducing Cell Aggregates Firstly, differentiation-inducing cell aggregates were prepared according to the following procedures.

According to a similar method to that of Test Example 2, the human iPS cells one day before subconfluence were cultured under feeder free conditions using the StemFit medium (AK03; Ajinomoto) in the presence of SB431542 (TGFβ signaling pathway inhibitory compound (TGFβR-i), 5 μmol/L) for 1 day. A 6-well plate (Iwaki, for cell culture, culture area 9.4 cm$^2$) was used as the plastic culture dish, and the number of plated cells for the human iPS cells dispersed into single cells was set 1.0×10$^4$. The cells were treated with cell dispersion using TrypLE Select (Life Technologies), and dispersed into single cells by pipetting operation. The cells were then suspended in 100 μl of a serum-free medium at 1.0×10$^4$ cells per well of a non-cell adhesive 96-well culture plate (PrimeSurface 96V-bottom plate, manufactured by SUMITOMO BAKELITE), and cultured in suspension at 37° C. and 5% $CO_2$. As the serum-free medium (gfCDM+KSR), a serum-free medium which is 1:1 mixture of F-12 medium and IMDM medium supplemented with 10% KSR, 450 μmol/L 1-monothioglycerol, and 1×Chemically defined lipid concentrate was used. At the time of the start of suspension culture (day 0 after the start of suspension culture), Y27632 (final concentration: 20 µmol/L) was added to the medium, and the cells was further cultured using a medium containing Wnt signaling inhibitory compound (IWR-1e, 3 µmol/L).

After culturing at 37° C. and 5% $CO_2$ for 24 hours, the medium was changed to the serum-free medium containing the present compound in a final concentration of 0.1 µmol/L or 1 µmol/L, or DMSO in a concentration equal thereto, and the cells were cultured for additional 24 hours. After 24 hours, the obtained cell aggregates were fixed with 4% paraformaldehyde to prepare frozen sections. The immunostaining of Cleaved Caspase-3 (anti Cleaved Caspase-3 antibody, Cell Signaling, Mouse) which is one of apoptosis markers and Oct3/4 (anti Oct3/4 antibody antibody, Santa Cruz, Rabbit) which is one of undifferentiated markers was performed for the frozen sections. In addition, DAPI (Sigma) nuclear staining was performed. The immunostained sections were observed by inverted fluorescence microscope (Keyence, BIREVO). In addition, the Cleaved Caspase-3 positive area was calculated using the NIH Image-J software.

As a result, it was confirmed that the differentiation-inducing cell aggregates used in this test example expressed Oct3/4 which is an undifferentiated marker, and undifferentiated iPS cells were contained in the cell aggregates. In addition, the ratio of Cleaved Caspase-3 positive area in the cell aggregates without treatment with the compounds of Examples 1-2 and 10-2 was 19%, whereas that of cell aggregates treated with the compound of Example 1-2 was 24% in 0.1 µmol/L and 27% in 1 µmol/L (FIGS. 5 and 7—the compound of Example 1-2). Also, the ratio of Cleaved Caspase-3 positive area in the cell aggregates treated with 1 µmol/L of the compound of Example 10-2 was 26% (FIGS. 6 and 7—the compound of Example 10-2).

As described above, the present compound increased the ratio of Cleaved Caspase-3 positive area in the differentiation-inducing cell aggregates. Also, it was found that the ratio of the positive area was increased inside the cell aggregates. Cell aggregates containing visual cells can be formed by culturing the differentiation-inducing cell aggregates in this test example according to the method described in WO 2016/063985.

INDUSTRIAL APPLICABILITY

The present compound has a potent inhibitory effect on sphere-forming ability of cancer cells. Also, the present compound can inhibit the proliferation of iPS cells and induce cell death, and thus is useful as an agent for removing iPS cells.

The invention claimed is:
1. A method of removing iPS cells, comprising adding a compound of formula (1):

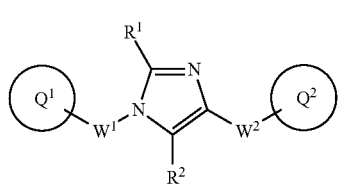

or a salt thereof, wherein $Q^1$ is optionally-substituted $C_{6-10}$ aryl, optionally-substituted $C_{6-10}$ aryloxy, optionally-substituted $C_{6-10}$ arylthio, optionally-substituted $C_{3-10}$ cycloalkyl, or optionally-substituted 5- to 10-membered heteroaryl;

$R^1$ and $R^2$ are independently hydrogen atom, halogen atom, or $C_{1-6}$ alkyl which may be optionally substituted with the same or different 1 to 3 halogen atoms;

$W^1$ is $C_{1-4}$ alkylene which may be optionally substituted with 1 to 3 fluorine atoms or $C_{3-7}$ cycloalkyl;

$W^2$-$Q^2$ is —$NR^{3a}C(O)$-$Q^2$, —$NR^{3a}C(O)OCH_2$-$Q^2$, —$NR^{3a}C(O)OCH_2$-$Q^2$, —$NR^{3a}C(O)NR^{3b}$-$Q^2$, —$NR^{3a}C(O)NR^{3b}CH_2$-$Q^2$, —$NR^{3a}C(O)CH_2O$-$Q^2$, —$NR^{3a}C(O)CH_2$-$Q^2$, —$NR^{3a}C(O)CH_2CH_2$-$Q^2$, —$C(O)NR^{3a}$-$Q^2$, —$C(O)NR^{3a}CH_2$-$Q^2$, —$C(O)NR^{3a}CH_2CH_2$-$Q^2$, or $NR^{3a}C(O)$—$CR^{3c}$=$CR^{3d}$-$Q^2$ wherein $R^{3a}$ and $R^{3b}$ are independently hydrogen atom or $C_{1-6}$ alkyl; $R^{3c}$ and $R^{3d}$ are independently hydrogen atom, fluorine atom, or $C_{1-6}$ alkyl; and ring $Q^2$ is optionally-substituted $C_{6-10}$ aryl or optionally-substituted 5- to 10-membered heteroaryl into a culture solution containing iPS cells or a culture solution containing a cell mass formed from iPS cells.

2. The method according to claim 1, wherein $Q^1$ is phenyl which may be optionally substituted with the same or different 1 to 4 groups selected from the group consisting of
(1) halogen atom,
(2) $C_{1-6}$ alkyl which may be optionally substituted with the same or different 1 to 3 groups selected from the group consisting of halogen atom, hydroxy, and $C_{1-6}$ alkoxy,
(3) $C_{1-6}$ alkoxy which may be optionally substituted with the same or different 1 to 3 groups selected from the group consisting of halogen atom, hydroxy, $C_{1-6}$ alkoxy, and phenyl,
(4) amino which may be optionally substituted with the same or different 1 to 2 $C_{1-6}$ alkyl groups,
(5) $C_{6-10}$ aryl which may be optionally substituted with the same or different 1 to 4 groups selected from the group consisting of halogen atom, $C_{1-6}$ alkyl, and $C_{1-6}$ alkoxy,
(6) $C_{6-10}$ aryloxy which may be optionally substituted with the same or different 1 to 4 groups selected from the group consisting of halogen atom, $C_{1-6}$ alkyl, and $C_{1-6}$ alkoxy,
(7) 5- to 10-membered heteroaryl which may be optionally substituted with the same or different 1 to 4 groups selected from the group consisting of halogen atom, $C_{1-6}$ alkyl, and $C_{1-6}$ alkoxy, and
(8) $C_{1-6}$ alkoxycarbonyl.

3. The method according to claim 1, wherein $Q^1$ is phenyl which may be optionally substituted with the same or different 1 to 4 groups selected from the group consisting of halogen atom, and $C_{1-6}$ alkyl which may be optionally substituted with the same or different 1 to 3 halogen atoms.

4. The method according to claim 1, wherein $W^2$-$Q^2$ is —$NHC(O)$-$Q^2$, —$NHC(O)$—$CH$=$CH$-$Q^2$, —$C(O)NH$-$Q^2$, or —$NHC(O)CH_2O$-$Q^2$.

5. The method according to claim 1, wherein $W^1$ is methylene.

6. The method according to claim 1, wherein ring $Q^2$ is
(1) phenyl which may be optionally substituted with the same or different 1 to 4 groups selected from the group consisting of (a) halogen atom,
(b) $C_{1-6}$ alkyl which may be optionally substituted with the same or different 1 to 3 groups selected from the group consisting of halogen atom, hydroxy, and $C_{1-6}$ alkoxy,
(c) $C_{1-6}$ alkoxy which may be optionally substituted with the same or different 1 to 3 groups selected from the group consisting of halogen atom, hydroxy, and $C_{1-6}$ alkoxy,
(d) $C_{3-7}$ cycloalkyl,
(e) $C_{2-6}$ alkenyl,
(f) cyano,
(g) amino which may be optionally substituted with the same or different 1 to 2 $C_{1-6}$ alkyl groups, and
(h) $C_{1-6}$ alkyl-carbonylamino,
(2) 5- to 10-membered heteroaryl which may be optionally substituted with the same or different 1 to 4 groups selected from the group consisting of (a) to (h) defined in the above (1), or
(3) a group of the following formula (11), (12), (13), (14), (15), or (16):

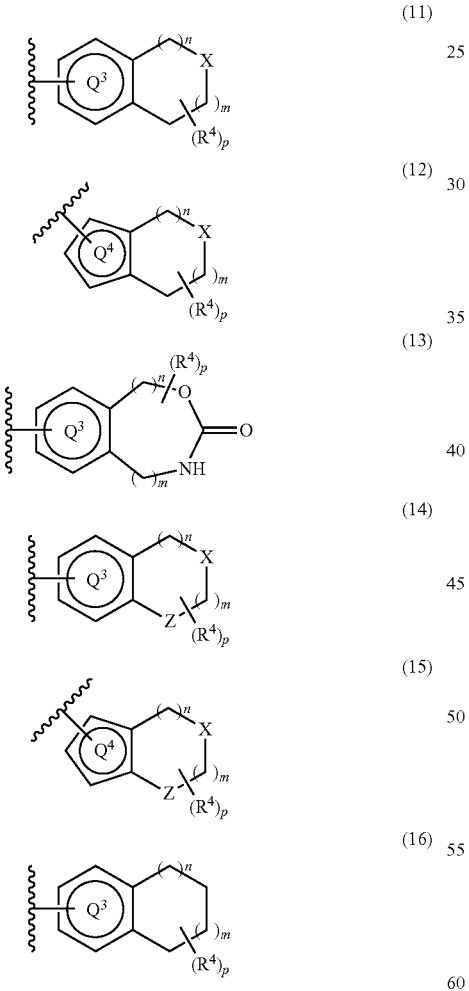

wherein ring $Q^3$ is optionally-substituted benzene ring, optionally-substituted pyridine ring, optionally-substituted pyrimidine ring, optionally-substituted pyridazine ring, or optionally-substituted pyrazine ring;
ring $Q^4$ is optionally-substituted 5-membered heteroaryl ring;

n and m are independently 0, 1, or 2, provided that n and m are not simultaneously 0;
X and Z are independently $NR^5$, $-NR^{3e}C(O)-$, $-C(O)NR^{3e}-$, or O wherein $R^5$ is hydrogen atom, $C_{1-6}$ alkyl which may be optionally substituted with the same or different 1 to 3 halogen atoms, or $C_{1-6}$ alkylcarbonyl; $R^{3e}$ is hydrogen atom or $C_{1-6}$ alkyl;
p is 1, 2, 3, 4, or 5;
$R^4$ is, independently when two or more exist, hydrogen atom, halogen atom, hydroxy, oxo, $C_{1-6}$ alkyl which may be optionally substituted with the same or different 1 to 3 halogen atoms, or $C_{1-6}$ alkoxy which may be optionally substituted with the same or different 1 to 3 halogen atoms.

7. The method according to claim 1, wherein ring $Q^2$ is
(1) phenyl which may be optionally substituted with the same or different 1 to 2 groups selected from the group consisting of $C_{1-6}$ alkoxy which may be optionally substituted with hydroxy, and $C_{1-6}$ alkyl-carbonylamino,
(2) a group of the following formula (2):

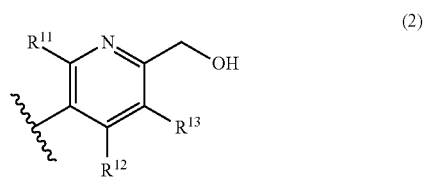

wherein $R^{11}$, $R^{12}$, and $R^{13}$ are independently
(a) hydrogen atom,
(b) halogen atom,
(c) $C_{1-6}$ alkyl which may be optionally substituted with the same or different 1 to 3 fluorine atoms, or
(d) amino which may be optionally substituted with the same or different 1 to 2 $C_{1-6}$ alkyl groups, or
(3) a group of the following formula (21):

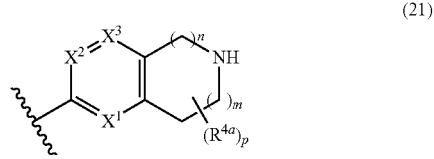

wherein $X^1$ is N or $CR^{14}$;
$X^2$ is N or $CR^{15}$;
$X^3$ is N or $CR^{16}$;
provided that $X^1$, $X^2$ and $X^3$ are not simultaneously N;
$R^{14}$, $R^{15}$ and $R^{16}$ are independently
(a) hydrogen atom,
(b) halogen atom,
(c) $C_{1-6}$ alkyl which may be optionally substituted with the same or different 1 to 3 halogen atoms, or
(d) $C_{1-6}$ alkoxy which may be optionally substituted with the same or different 1 to 3 halogen atoms;
n and m are independently 0, 1, or 2, provided that n and m are not simultaneously 0;
p is 1, 2, 3, 4, or 5;
$R^{4a}$ is independently when two or more exist, hydrogen atom, halogen atom, or $C_{1-6}$ alkyl which may be optionally substituted with the same or different 1 to 3 halogen atoms.

8. The method according to claim 7, wherein $W^2$-$Q^2$ is —NHC(O)-$Q^2$, or —C(O)NH-$Q^2$; and
ring $Q^2$ is a group of formula (2) or (21).

9. The method according to claim 7, wherein $R^{11}$ and $R^{12}$ are hydrogen atom;
$R^{13}$ is hydrogen atom, $C_{1-4}$ alkyl which may be optionally substituted with 1 to 3 fluorine atoms, or amino;
$R^{14}$, $R_{15}$ and $R^{16}$ are independently hydrogen atom or fluorine atom;
n is 1;
m is 0 or 1;
p is 1 or 2;
$R^{4a}$ is independently when two or more exist, hydrogen atom or methyl.

10. The method according to claim 1, wherein $W^2$-$Q^2$ is —NHC(O)—CH=CH-$Q^2$; and
ring $Q^2$ is phenyl which may be optionally substituted with the same or different 1 to 2 groups selected from the group consisting of $C_{1-6}$ alkoxy which may be optionally substituted with hydroxy, and $C_{1-6}$ alkyl-carbonylamino.

11. The method according to claim 1, wherein $R^1$ and $R^2$ are hydrogen atom.

12. The method according to claim 1, wherein the compound of formula (1) is selected from the following compounds:
(2E)-3-[4-(acetylamino)phenyl]-N-(1-[3-(trifluoromethyl)benzyl]-1H-imidazol-4-yl)prop-2-enamide,
N-[1-(3-chlorobenzyl)-1H-imidazol-4-yl]-3,4-dimethoxybenzamide, and
6-(hydroxymethyl)-N—{1-[3-(trifluoromethyl)benzyl]-1H-imidazol-4-yl}nicotinamide;
or a salt thereof.

13. The method of claim 1, which comprises adding the compound of formula (1), or a salt thereof, into a culture solution containing iPS cells.

14. The method of claim 1, which comprises adding the compound of formula (1), or a salt thereof, into a culture solution containing a cell mass formed from iPS cells.

15. A method of preparing an iPS cell-derived cell population free of iPS cells, which comprises contacting an iPS cell-derived cell population with the compound of formula (1):

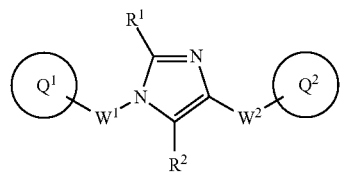

(1)

or a salt thereof, wherein:
$Q^1$ is optionally-substituted $C_{6-10}$ aryl, optionally-substituted $C_{6-10}$ aryloxy, optionally-substituted $C_{6-10}$ arylthio, optionally-substituted $C_{3-10}$ cycloalkyl, or optionally-substituted 5- to 10-membered heteroaryl;
$R^1$ and $R^2$ are independently hydrogen atom, halogen atom, or $C_{1-6}$ alkyl which may be optionally substituted with the same or different 1 to 3 halogen atoms;
$W^1$ is $C_{1-4}$ alkylene which may be optionally substituted with 1 to 3 fluorine atoms or $C_{3-7}$cycloalkyl;
$W^2$-$Q^2$ is —$NR^{3a}$C(O)-$Q^2$, —$NR^{3a}$C(O)OCH$_2$-$Q^2$, —$NR^{3a}$C(O)OCH$_2$-$Q^2$, —$NR^{3a}$C(O)$NR^{3b}$-$Q^2$, —$NR^{3a}$C(O)$NR^{3b}$CH$_2$-$Q^2$, —$NR^{3a}$C(O)CH$_2$O-$Q^2$, —$NR^{3a}$C(O)CH$_2$-$Q^2$, —$NR^{3a}$C(O)CH$_2$CH$_2$-$Q^2$, —C(O)$NR^{3a}$-$Q^2$, —C(O)$NR^{3a}$CH$_2$-$Q^2$, —C(O)$NR^{3a}$CH$_2$CH$_2$-$Q^2$, or $NR^{3a}$C(O)—$CR^{3c}$=$CR^{3d}$-$Q^2$
wherein $R^{3a}$ and $R^{3b}$ are independently hydrogen atom or $C_{1-6}$ alkyl; $R^{3c}$ and $R^{3d}$ are independently hydrogen atom, fluorine atom, or $C_{1-6}$ alkyl; and
ring $Q^2$ is optionally-substituted $C_{6-10}$ aryl or optionally-substituted 5- to 10-membered heteroaryl.

16. A method of preparing an iPS cell-derived cell population free of cells maintaining pluripotency, which comprises:
(1) inducing differentiation of a cell population containing iPS cells, and
(2) contacting the cell population obtained in step (1) with the compound of formula (1):

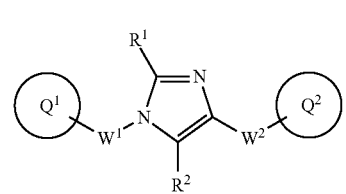

(1)

or a salt thereof, wherein:
$Q^1$ is optionally-substituted $C_{6-10}$ aryl, optionally-substituted $C_{6-10}$ aryloxy, optionally-substituted $C_{6-10}$ arylthio, optionally-substituted $C_{3-10}$ cycloalkyl, or optionally-substituted 5- to 10-membered heteroaryl;
$R^1$ and $R^2$ are independently hydrogen atom, halogen atom, or $C_{1-6}$ alkyl which may be optionally substituted with the same or different 1 to 3 halogen atoms;
$W^1$ is $C_{1-4}$ alkylene which may be optionally substituted with 1 to 3 fluorine atoms or $C_{3-7}$cycloalkyl;
$W^2$-$Q^2$ is —$NR^{3a}$C(O)-$Q^2$, —$NR^{3a}$C(O)OCH$_2$-$Q^2$, —$NR^{3a}$C(O)OCH$_2$-$Q^2$, —$NR^{3a}$C(O)$NR^{3b}$-$Q^2$, —$NR^{3a}$C(O)$NR^{3b}$CH$_2$-$Q^2$, —$NR^{3a}$C(O)CH$_2$O-$Q^2$, —$NR^{3a}$C(O)CH$_2$-$Q^2$, —$NR^{3a}$C(O)CH$_2$CH$_2$-$Q^2$, —C(O)$NR^{3a}$-$Q^2$, —C(O)$NR^{3a}$CH$_2$-$Q^2$, —C(O)$NR^{3a}$CH$_2$CH$_2$-$Q^2$, or $NR^{3a}$C(O)—$CR^{3c}$=$CR^{3d}$-$Q^2$
wherein $R^{3a}$ and $R^{3b}$ are independently hydrogen atom or $C_{1-6}$ alkyl; $R^{3c}$ and $R^{3d}$ are independently hydrogen atom, fluorine atom, or $C_{1-6}$ alkyl; and
ring $Q^2$ is optionally-substituted $C_{6-10}$ aryl or optionally-substituted 5- to 10-membered heteroaryl.

17. An iPS cell-derived cell population free of iPS cells, prepared by the method according to claim 15.

18. The cell population according to claim 17 containing cells for transplantation.

19. A pharmaceutical composition comprising cells in the cell population according to claim 17 as an active ingredient.

* * * * *